US007141659B2

(12) United States Patent
Keeling et al.

(10) Patent No.: US 7,141,659 B2
(45) Date of Patent: Nov. 28, 2006

(54) STARCH ENCAPSULATION

(75) Inventors: Peter Keeling, Ames, IA (US);
Hanping Guan, Ames, IA (US)

(73) Assignee: BASF Plant Science GmbH,
Ludwigshafen (DE)

( * ) Notice: Subject to any disclaimer, the term of this patent is extended or adjusted under 35 U.S.C. 154(b) by 164 days.

(21) Appl. No.: 10/628,525

(22) Filed: Jul. 28, 2003

(65) Prior Publication Data

US 2004/0185114 A1    Sep. 23, 2004

Related U.S. Application Data

(63) Continuation of application No. 09/625,406, filed on Jul. 25, 2000, now abandoned, which is a continuation of application No. 08/941,445, filed on Sep. 30, 1997, now Pat. No. 6,107,060.

(60) Provisional application No. 60/026,855, filed on Sep. 30, 1996.

(51) Int. Cl.
*C07H 21/04* (2006.01)
*A61K 49/14* (2006.01)
*C12P 19/14* (2006.01)

(52) U.S. Cl. .............. 536/23.1; 435/69.1; 435/320.1; 435/99; 530/350; 530/370; 424/9

(58) Field of Classification Search .............. 536/23.1; 435/69.1, 69.7, 320.1, 235, 99; 530/370, 530/350, 395; 424/9
See application file for complete search history.

(56) References Cited

U.S. PATENT DOCUMENTS

| | | | |
|---|---|---|---|
| 4,859,377 A | 8/1989 | Shasha et al. | |
| 5,137,819 A | 8/1992 | Kilburn et al. | |
| 5,202,247 A | 4/1993 | Kilburn et al. | |
| 5,302,523 A | 4/1994 | Coffee et al. | |
| 5,349,123 A | 9/1994 | Shewmaker et al. | |
| 5,512,459 A | 4/1996 | Wagner et al. | |
| 5,635,599 A | 6/1997 | Pastan et al. | |
| 5,643,756 A | 7/1997 | Kayman et al. | |
| 5,648,244 A | 7/1997 | Kuliopulos et al. | |
| 5,977,437 A * | 11/1999 | Villand et al. | 800/284 |
| 6,307,125 B1 * | 10/2001 | Block et al. | 800/284 |

OTHER PUBLICATIONS

Bruce, B. D. (2000) Chloroplast transit peptides: structure, function, and evolution. Trends Cell Biol. vol. 10, No. 10, pp. 440-447.*
Baba, T. et al., "Identification, cDNA Cloning, and Gene Expression of Soluble Starch Sythase in Rice (*Oryza sativa* L.) Immature Seeds" (1993), Plant Physiol. 103:565-573.
Baba, T. et al "Sequence Conservation of the Catalytic Regions of Amylolytic Enzymes in Maize Branching Enzyme-I" (1991) Biochem. Biophys. Res. Comm. 181(1):87-94.
Bhattacharyya, M. et al. "The Importance of Starch Biosynthesis in the Wrinkled Seed Shape Character of Peas Studied by Mendel" (1993) Plant Mol. Biol. 22:525-531.
Boyer, C. et al. "Multiple Forms of (1-4)-a-D-GLUCAN-6-Glycosyl Transferase from Development Zea Mays L. Kernels" (1978) Carbohydrate Research 61:321-334.
Broekhuijsen, M. et al. "Secretion of heterologogous proteins by *Aspergillus niger*: Production of active . . . " (1993) Journal of Biotechnology 31:135-145.
Browner, M. et al. "Human muscle glycogen synthase cDNA sequence: A negatively charged protein with an asymmetric char . . . " (Mar. 1989) Proc. Natl. Acad. Sci. USA 86:1443-1447.
Chen, L et al. "Improved Adsorption to Starch of a B-Galactosidase Fusion Protein Containing the Starch-Binding Domain from Aspergillus . . . " (1991) Biotechnol. Prog. 7:225-229.
Dang, P. et al. "Maize Leaf and Kernel Starch Synthases and Starch Branching Enzymes" (1988) Phytochemistry 27(5):1255-1259.
Denyer, K. et al. "Identification of multiple isoforms of soluble and granule-bound starch synthase in development wheat endosperm" (1995) Plant 196:256-265.
Denyer, K. et al. "The purification and characterisation of the two formsof soluble starch synthase from developing pea embryos" (1992) Planta 186:609-617.
Denyer, K. et al. "Soluble isoforms of starch synthase and starch-branching enzyme also occur within starch granules in developing . . . " (1993) The Plant Journal 4(1):191-198.
Dry, I. et al. "Characterization of cDNAs encoding two isoforms of granule-bound starch synthase which show differential expression . . . " (1992) The Plant Journal 2(2):193-202.
Edwards, A. et al. "Evidence that a 77-Kilodalton Protein from the Starch of Pea Embryos Is an Isoform of Starch Synthase That Is Both . . . " (1996) Plant Physiol. 112:89-97.
Frydman, R. et al. "Soluble Enzymes Related to Starch Synthesis" (1964) Biochem. and Biophys. Res. Comm. 17(4):407-411.
Furukawa, K. et al. "Role of the Conserved Lys-X-Gly-Gly Sequence at the ADP-glucose-binding Site in . . . " (Nov. 15, 1993) The Journal of Biological Chemistry 268(32):23837-23842.
Furukawa, K. et al. "Identification of Lysine 15 at the Active Site in *Escherichia coli* Glycogen Synthase" (Feb. 5, 1990) The Journal of Biological Chemistry 265(4):2086-2090.

(Continued)

*Primary Examiner*—Jon Weber
*Assistant Examiner*—Samuel Wei Liu
(74) *Attorney, Agent, or Firm*—Patricia A. McDaniels

(57) ABSTRACT

The present invention relates to a recombinant nucleic acid encoding a hybrid polypeptide which comprises a transit peptide for the translocation of the polypeptide into an appropriate organelles such as plastids, a starch-encapsulating region from maize starch synthase and a payload polypeptide, wherein said payload polypeptide can be either N- or C-terminal to the starch encapsulating region. The invention also relates to the expression vectors comprising said nucleic acid, and hosts comprising the said vector. Also, the invention encompasses methods of producing the hybrid polypeptide thereof from starch and particularly from starch granules, and industrial uses of the payload polypeptide recombinantly produced in said hybrid polypeptide wherein said payload polypeptide is a biologically active molecule.

6 Claims, 12 Drawing Sheets

OTHER PUBLICATIONS

Goddijin, O. et al. "Plants as bioreactors" (Sep. 1995) Trends in Biotechnology 13(9):379-387.

Hovenkamp-Hermelink, J. et al. "Isolation of an amylose-free starch mutant of the potato (*Solanum tuberosum* L.)" (1987) Theor. Appl. Genet. 75:217-221.

Jenner, C. et al. "Thermal Characteristics of Soluble Starch Synthase from Wheat Endosperm" (1995) Aust. J. Plant. Physiol. 22:703-709.

Keeling, P. et al. "Effect of Temperature on Enzymes in the Pathway of Starch Biosynthesis in Developing Wheat and Maize Grain" (1994) Aust. J. Plant. Physiol. 21:807-827.

Keeling, P. et al. "Elevated temperature reduces starch deposition in wheat endosperm by reducing the activity of soluble starch synthase" (1993) Planta 191:342-348.

Kiel, J. et al. "Molecular cloning and nucleotide sequence of the glycogen branching enzyme gene (glgB) from Bacillus . . . " (1991) Mol. Gen. Genet. 230:136-144.

Kiel, J. et al. "Cloning and expression of thebranching enzyme gene (glgB) from thecyanobacterium Synechococcus sp. PCC7942 in *Escherichia coli*" (1989) Gen. 78:9-17.

Kirihara, J. et al. "Isolation and sequence of a gene encoding a methionine-rich 10-kDa zein protein from maize" (1988) Gen. 71:359-370.

Kobmann, J. et al. "Cloning and expression analysis of a potato cDNA that encodes branching enzyme: evidence for co-expression of starch . . . " (1991) Mol. Gen. Genet. 230:39-44.

Kumar, A. et al. "Biosynthesis of Bacterial Glycogen" (Dec. 5, 1986) The Journal of Biological Chemistry, 261(34):16256-16259.

Kusnadi, A. et al. "Functional starch-binding domain of *Aspergillus glucoamylase* I in *Escherichia coli*" (1993) Gene 127:193-197.

Leung, P. et al. "Cloning and Expression of the *Escherichia coli* glgC Gene from a Mutant Containing an ADPglucose . . . " (Jul. 1986) J. of Bacteriology, 167(1):82-88.

McCormick, M. et al. "Purification and S-Tag detection of CBD fusion proteins" (1997) inNovations 7:12-15.

MacDonald, F. et al. "Partial Purification and Characterization of Granule-Bound Starch Synthases from Normal and Waxy Maize" (1985) Plant Physiol. 8:849-852.

MacDonald, F. et al. "Solubilization of the Starch-Granule-Bound Starch Synthase of Normal Maize Kernels" (1983) Plant Physiol. 73:175-178.

Marshall, J. et al. "Identification of the Major Starch Synthase in theSoluble Fraction of Potato Tubers" (Jul. 1996) the Plant Cell 8:1121-1135.

Matsumoto, A. et al. "A Kinetic Study of the Interactioin between Glycogen and *Neurospora crassa* Branching Enzyme" (1990) J. Biochem. 107:123-126.

Monsma, A. et al. "New pBAC transfer plasmids for baculovirus expression of CBD fusion proteins" (1997) InNovations 7:8-11.

Monsma, A. et al. "BacVector-3000: An engineered baculovirus designed for greater protein stability" (1997) InNovations 7:16-24.

Mu, C. et al. "Association of a 76 kDa polypeptide with soluble starch synthase I activity in maize (cv B73) endosperm" (1994) The Plant Journal 6(2):151-159.

Mu-Forster, C. et al. "Physical Association of Starch Biosynthetic Enzymes with Starch Granules of Maize Endosperm" (1996) Plant Physiol. 111:821-829.

Nakamura, Y. et al. "Nucleotide Sequence of a cDNA Encoding Starch-Branching Enzyme, or Q-Enzyme I, from Rice Endosperm" (1992) Plant Physiol 99:1265-1266.

Nakamura, Y. et al. "Purification of two forms of starch branching enzyme (Q-enzyme) from developing rice endosperm" (1992) Physiologia Plantarum 84:329-335.

Novy, R. et al. "New pET expression vectors generate fusion proteins with cellulose binding domains" (1981) inNovations 7:4-7.

Okita, T. et al. "Biosynthesis of Bacterial Glycogen" (Jul. 10, 1981) The Journal of Biological Chemistry 256(13):6944-6952.

Pollock, C. et al. "The Citrate-Stimulated Starch Synthase of Starchy Maize Kernels: Purification and Properties" (1980) Archives of Biochemistry and Biophysics 204(2):578-58.

Rowen, D. et al. "GLC3 and GHA1 of *Saccharomyces cerevisiae* Are Allelic and Encode the glycogen Branching Enzyme" (Jan. 1992) Molecular and Cellular Biology 12(1):22-29.

Salehuzzaman, S. et al. "Cloning, partial sequencing and expression of a cDNA coding for branching enzyme in cassava" (1992) Plant Molecular Biology 20:809-819.

Shimada, H. "Antisense regulation of the rice waxy gene expression using a PCR-amplified fragment of the rice genome reduces . . . " (1993) Theor. Appl. Genet. 86:665-672.

Shure, M. et al. "Molecular Identification and Isolation of the Waxy Locus in Maize" (Nov. 1983) Cell 35:225-233.

Smith, A. "Major differences in isoforms of starch-branching enzyme between developing embryos of round- and wrinkled-seeded peas (*Pisum sativum* . . . "(1988) Planta 175:270-279.

Shoseyov, O. et al. "Cellulose binding domains—A novel fusion technology for efficient, low cost purification and immobilization of . . . " (Aug. 1997) InNovations 7:1-3.

Singh, B. et al. "Starch Branching Enzymes from Maize" (1985) Plant Physiol. 79:34-40.

Svensson, B. et al. "Sequence homology between putative raw-starch binding domains from different starch-degrading enzymes" (1989) Biochem. J. 264:309-311.

Takahashi, T. et al. "Different Behavior towards Raw Starch of Three Forms of Glucoamylase from a Rhizopus Sp." (1985) J. Biochem. 98:663-671.

Tsai, C. "The Function of the Waxy Locus in Starch synthesis in Maize Endosperm" (1974) Biochemical Genetics (11(2):83-96.

Tyynela, J. et al. "An analysis of soluble starch synthase isozymes from the developing grains of normal and shx cv. Bomi Barley . . . " (1993) Physiologia Plantarum 89:835-841.

Valvekens, D. et al. "*Agrobacterium tumefaciens*-mediated transformation of *Arabidopsis thaliana* root explants by using . . . " (Aug. 1988) Proc. Natl. Acad. Sci. USA 85:5536-5540.

Van Der Leij, F. et al. "Complementation of the amylose-free starch mutant of potato (*Solanum tuberosum*.) by the gene encoding . . . " (1991) Theor. Appl. Genet. 82:289-295.

Visser, R. et al. "Inhibition of the expression fo the gene for granule-bound starch synthase in potato by antisense constructs" (1991) Mol. Gen. Genet. 225:289-296.

Visser, R. et al. "Molecular Cloning and Partial Characterization of the Gene for Granule-bound Starch Synthase from a Wildtype and an . . . "(1989) Plant Science 64:185-192.

Von Heijne, G. et al. "CHLPEP—A Database of Chloroplast Transit Peptides" (1991) Plant Molecular Biology Reporter 9(2):104-126.

Vos-Sheperkeuter, G. et al. "Immunological Comparison of the Starch Branching Enzymes from Potato Tubers and Maize Kernels" (1989) Plant Physiol 90:75-84.

Zhang, W. et al. "Primary structure of rabbit skeletal muscle glycogen synthase deduced from cDNA clones" (1989) The BASEB Journal 3:2532-2536.

* cited by examiner

STARCH ENCAPSULATION

CROSS-REFERENCE TO RELATED APPLICATIONS

This application is a continuation of U.S. patent application Ser. No. 09/625,406, filed Jul. 25, 2000, now abandoned which is a continuation of U.S. patent application Ser. No. 08/941,445, filed Sep. 30, 1997 and now U.S. Pat. No. 6,107,060, which claims priority to provisional patent application Ser. No. 60/026,855 filed Sep. 30, 1996. Said provisional application is incorporated herein by reference to the extent not inconsistent herewith.

BACKGROUND OF THE INVENTION

Polysaccharide Enzymes

Both prokaryotic and eukaryotic cells use polysaccharide enzymes as a storage reserve. In the prokaryotic cell the primary reserve polysaccharide is glycogen. Although glycogen is similar to the starch found in most vascular plants it exhibits different chain lengths and degrees of polymerization. In many plants, starch is used as the primary reserve polysaccharide. Starch is stored in the various tissues of the starch bearing plant. Starch is made of two components in most instances; one is amylose and one is amylopectin. Amylose is formed as linear glucans and amylopectin is formed as branched chains of glucans. Typical starch has a ratio of 25% amylose to 75% amylopectin. Variations in the amylose to amylopectin ratio in a plant can effect the properties of the starch. Additionally starches from different plants often have different properties. Maize starch and potato starch appear to differ due to the presence or absence of phosphate groups. Certain plants' starch properties differ because of mutations that have been introduced into the plant genome. Mutant starches are well known in maize, rice and peas and the like.

The changes in starch branching or in the ratios of the starch components result in different starch characteristic. One characteristic of starch is the formation of starch granules which are formed particularly in leaves, roots, tubers and seeds. These granules are formed during the starch synthesis process. Certain synthases of starch, particularly granule-bound starch synthase, soluble starch synthases and branching enzymes are proteins that are "encapsulated" within the starch granule when it is formed.

The use of cDNA clones of animal and bacterial glycogen synthases are described in International patent application publication number GB92/101881. The nucleotide and amino acid sequences of glycogen synthase are known from the literature. For example, the nucleotide sequence for the *E. coli* glgA gene encoding glycogen synthase can be retrieved from the GenBank/EMBL (SWISSPROT) database, accession number J02616 (Kumar et al., 1986, J. Biol. Chem., 261:16256–16259). *E. coli* glycogen biosynthetic enzyme structural genes were also cloned by Okita et al. (1981, J. Biol. Chem., 256(13):6944–6952). The glycogen synthase glgA structural gene was cloned from *Salmonella typhimurium* LT2 by Leung et al. (1987, J. Bacteriol., 169(9):4349–4354). The sequences of glycogen synthase from rabbit skeletal muscle (Zhang et al., 1989, FASEB J., 3:2532–2536) and human muscle (Browner et al., 1989, Proc. Natl. Acad. Sci., 86:1443–1447) are also known.

The use of cDNA clones of plant soluble starch synthases has been reported. The amino acid sequences of pea soluble starch synthase isoforms I and II were published by Dry et al. (1991, Plant Journal, 2:193202). The amino acid sequence of rice soluble starch synthase (SSTS) was described by Baba et al. (1993, Plant Physiology,). This last sequence (rice SSTA) incorrectly cites the N-terminal sequence and hence is misleading. Presumably this is because of some extraction error involving a protease degradation or other inherent instability in the extracted enzyme. The correct N-terminal sequence (starting with AELSR SEQ. ID NO:38) is present in what they refer to as the transit peptide sequence of the rice SSTS.

The sequence of maize branching enzyme I was investigated by Baba et al., 1991, BBRC, 181:8794. Starch branching enzyme II from maize endosperm was investigated by Fisher and Shrable (1993, Plant Physiol., 102:10451046). The use of cDNA clones of plant, bacterial and animal branching enzymes have been reported. The nucleotide and amino acid sequences for bacterial branching enzymes (BE) are known from the literature. For example, Kiel et al. cloned the branching enzyme gene glgB from *Cyanobacterium synechococcussp* PCC7942 (1989, Gene (Amst), 78(1):918) and from *Bacillus stearothermophilus* (Kiel et al., 1991, Mol. Gen. Genet., 230(12):136–144). The genes glc3 and gha1 of *S. cerevisiae* are allelic and encode the glycogen branching enzyme (Rowen et al., 1992, Mol. Cell Biol., 12(1):22–29). Matsumomoto et al. investigated glycogen branching enzyme from *Neurospora crassa* (1990, J. Biochem., 107:118–122). The GenBank/EMBL database also contains sequences for the *E. coli* glgB gene encoding branching enzyme.

Starch synthase (EC 2.4.1.11) elongates starch molecules and is thought to act on both amylose and amylopectin. Starch synthase (STS) activity can be found associated both with the granule and in the stroma of the plastid. The capacity for starch association of the bound starch synthase enzyme is well known. Various enzymes involved in starch biosynthesis are now known to have differing propensities for binding as described by Mu-Forster et al. (1996, Plant Phys. 111: 821–829). Granule-bound starch synthase (GB-STS) activity is strongly correlated with the product of the waxy gene (Shure et al., 1983, Cell 35: 225–233). The synthesis of amylose in a number of species such as maize, rice and potato has been shown to depend on the expression of this gene (Tsai, 1974, Biochem Gen 11: 83–96; Hovenkamp-Hermelink et al., 1987, Theor. Appl. Gen. 75: 217–221). Visser et al. described the molecular cloning and partial characterization of the gene for granule-bound starch synthase from potato (1989, Plant Sci. 64(2):185192). Visser et al. have also described the inhibition of the expression of the gene for granule-bound starch synthase in potato by antisense constructs (1991, Mol. Gen. Genet. 225(2):289296).

The other STS enzymes have become known as soluble starch synthases, following the pioneering work of Frydman and Cardini (Frydman and Cardini, 1964, Biochem. Biophys. Res. Communications 17: 407–411). Recently, the appropriateness of the term "soluble" has become questionable in light of discoveries that these enzymes are associated with the granule as well as being present in the soluble phase (Denyer et al., 1993, Plant J. 4: 191–198; Denyer et al., 1995, Planta 97: 57–62; Mu-Forster et al., 1996, Plant Physiol. 111: 821–829). It is generally believed that the biosynthesis of amylopectin involves the interaction of soluble starch synthases and starch branching enzymes. Different isoforms of soluble starch synthase have been identified and cloned in pea (Denyer and Smith, 1992, Planta 186: 609–617; Dry et al., 1992, Plant Journal, 2: 193–202), potato (Edwards et al., 1995, Plant Physiol. 112: 89–97;

Marshall et al., 1996, Plant Cell 8: 1121–1135) and in rice (Baba et al., 1993, Plant Physiol. 103: 565–573), while barley appears to contain multiple isoforms, some of which are associated with starch branching enzyme (Tyynela and Schulman, 1994, Physiol. Plantarum 89: 835–841). A common characteristic of STS clones is the presence of a KXGGLGDV (SEQ. ID NO:39) consensus sequence which is believed to be the ADP-Glc binding site of the enzyme (Furukawa et al., 1990, J. Biol. Chem. 265: 2086–2090; Furukawa et al., 1993, J. Biol. Chem. 268:23837–23842).

In maize, two soluble forms of STS, known as isoforms I and II, have been identified (Macdonald and Preiss, 1983, Plant Physiol. 73: 175–178; Boyer and Preiss, 1978, Carb. Res. 61: 321–334; Pollock and Preiss, 1980, Arch Biochem. Biophys. 204: 578–588; Macdonald and Preiss, 1985 Plant Physiol. 78: 849–852; Dang and Boyer, 1988, Phytochemistry 27: 1255–1259; Mu et al., 1994, Plant J. 6: 151–159), but neither of these has been cloned. STSI activity of maize endosperm was recently correlated with a 76-kDa polypeptide found in both soluble and granule-associated fractions (Mu et al., 1994, Plant J. 6: 151–159). The polypeptide identity of STSII remains unknown. STSI and II exhibit different enzymological characteristics. STSI exhibits primer-independent activity whereas STSII requires glycogen primer to catalyze glucosyl transfer. Soluble starch synthases have been reported to have a high flux control coefficient for starch deposition (Jenner et al., 1993, Aust. J. Plant Physiol. 22: 703–709; Keeling et al., 1993, Planta 191: 342–348) and to have unusual kinetic properties at elevated temperatures (Keeling et al., 1995, Aust. J. Plant Physiol. 21807–827). The respective isoforms in maize exhibit significant differences in both temperature optima and stability.

Plant starch synthase (and *E. coli* glycogen synthase) sequences include the sequence KTGGL (SEQ ID NO:40) which is known to be the adenosine diphosphate glucose (ADPG) binding domain. The genes for any such starch synthase protein may be used in constructs according to this invention.

Branching enzyme [α1,4Dglucan: α1,4Dglucan 6D(α1, 4Dglucano) transferase (E.C. 2.4.1.18)], sometimes called Q-enzyme, converts amylose to amylopectin. A segment of a α1,4Dglucan chain is transferred to a primary hydroxyl group in a similar glucan chain.

Bacterial branching enzyme genes and plant sequences have been reported (rice endosperm: Nakamura et. al., 1992, Physiologia Plantarum, 84:329–335 and Nakamura and Yamanouchi, 1992, Plant Physiol., 99:1265–1266; pea: Smith, 1988, Planta, 175:270–279 and Bhattacharyya et al., 1989, J. Cell Biochem., Suppl. 13D:331; maize endosperm: Singh and Preiss, 1985, Plant Physiology, 79:34–40; VosScherperkeuter et al., 1989, Plant Physiology, 90:75–84; potato: Kossmann et al., 1991, Mol. Gen. Genet., 230(12): 39–44; cassava: Salehuzzaman and Visser, 1992, Plant Mol Biol, 20:809–819).

In the area of polysaccharide enzymes there are reports of vectors for engineering modification in the starch pathway of plants by use of a number of starch synthesis genes in various plant species. That some of these polysaccharide enzymes bind to cellulose or starch or glycogen is well known. One specific patent example of the use of a polysaccharide enzyme shows the use of glycogen biosynthesis enzymes to modify plant starch. In U.S. Pat. No. 5,349,123 to Shewmaker a vector containing DNA to form glycogen biosynthetic enzymes within plant cells is taught. Specifically, this patent refers to the changes in potato starch due to the introduction of these enzymes. Other starch synthesis genes and their use have also been reported.

Hybrid (Fusion) Peptides

Hybrid proteins (also called "fusion proteins") are polypeptide chains that consist of two or more proteins fused together into a single polypeptide. Often one of the proteins is a ligand which binds to a specific receptor cell. Vectors encoding fusion peptides are primarily used to produce foreign proteins through fermentation of microbes. The fusion proteins produced can then be purified by affinity chromatography. The binding portion of one of the polypeptides is used to attach the hybrid polypeptide to an affinity matrix. For example, fusion proteins can be formed with beta galactosidase which can be bound to a column. This method has been used to form viral antigens.

Another use is to recover one of the polypeptides of the hybrid polypeptide. Chemical and biological methods are known for cleaving the fused peptide. Low pH can be used to cleave the peptides if an acid-labile aspartate-proline linkage is employed between the peptides and the peptides are not affected by the acid. Hormones have been cleaved with cyanobromide. Additionally, cleavage by site-specific proteolysis has been reported. Other methods of protein purification such as ion chromatography have been enhanced with the use of polyarginine tails which increase the overall basicity of the protein thus enhancing binding to ion exchange columns.

A number of patents have outlined improvements in methods of making hybrid peptides or specific hybrid peptides targeted for specific uses. U.S. Pat. No. 5,635,599 to Pastan et al. outlines an improvement of hybrid proteins. This patent reports a circularly permuted ligand as part of the hybrid peptide. This ligand possesses specificity and good binding affinity. Another improvement in hybrid proteins is reported in U.S. Pat. No. 5,648,244 to Kuliopulos. This patent describes a method for producing a hybrid peptide with a carrier peptide. This nucleic acid region, when recognized by a restriction endonuclease, creates a nonpalindromic 3-base overhang. This allows the vector to be cleaved.

An example of a specifically targeted hybrid protein is reported in U.S. Pat. No. 5,643,756. This patent reports a vector for expression of glycosylated proteins in cells. This hybrid protein is adapted for use in proper immunoreactivity of HIV gp120. The isolation of gp120 domains which are highly glycosylated is enhanced by this reported vector.

U.S. Pat. Nos. 5,202,247 and 5,137,819 discuss hybrid proteins having polysaccharide binding domains and methods and compositions for preparation of hybrid proteins which are capable of binding to a polysaccharide matrix. U.S. Pat. No. 5,202,247 specifically teaches a hybrid protein linking a cellulase binding region to a peptide of interest. The patent specifies that the hybrid protein can be purified after expression in a bacterial host by affinity chromatography on cellulose.

The development of genetic engineering techniques has made it possible to transfer genes from various organisms and plants into other organisms or plants. Although starch has been altered by transformation and mutagenesis in the past there is still a need for further starch modification. To this end vectors that provide for encapsulation of desired amino acids or peptides within the starch and specifically within the starch granule are desirable. The resultant starch is modified and the tissue from the plant carrying the vector is modified.

SUMMARY OF THE INVENTION

This invention provides a hybrid polypeptide comprising a starch-encapsulating region (SER) from a starch-binding enzyme fused to a payload polypeptide which is not endogenous to said starch-encapsulating region, i.e. does not naturally occur linked to the starch-encapsulating region. The hybrid polypeptide is useful to make modified starches comprising the payload polypeptide. Such modified starches may be used to provide grain feeds enriched in certain amino acids. Such modified starches are also useful for providing polypeptides such as hormones and other medicaments, e.g. insulin, in a starch-encapsulated form to resist degradation by stomach acids. The hybrid polypeptides are also useful for producing the payload polypeptides in easily-purified form. For example, such hybrid polypeptides produced by bacterial fermentation, or in grains or animals, may be isolated and purified from the modified starches with which they are associated by artknown techniques.

The term "polypeptide" as used herein means a plurality of identical or different amino acids, and also encompasses proteins.

The term "hybrid polypeptide" means a polypeptide composed of peptides or polypeptides from at least two different sources, e.g. a starch-encapsulating region of a starch-binding enzyme, fused to another polypeptide such as a hormone, wherein at least two component parts of the hybrid polypeptide do not occur fused together in nature.

The term "payload polypeptide" means a polypeptide not endogenous to the starch-encapsulating region whose expression is desired in association with this region to express a modified starch containing the payload polypeptide.

When the payload polypeptide is to be used to enhance the amino acid content of particular amino acids in the modified starch, it preferably consists of not more than three different types of amino acids selected from the group consisting of: Ala, Arg, Asn, Asp, Cys, Gln, Glu, Gly, His, Ile, Leu, Lys, Met, Phe, Pro, Ser, Thr, Trp, Tyr, and Val.

When the payload polypeptide is to be used to supply a biologically active polypeptide to either the host organism or another organism, the payload polypeptide may be a biologically active polypeptide such as a hormone, e.g., insulin, a growth factor, e.g. somatotropin, an antibody, enzyme, immunoglobulin, or dye, or may be a biologically active fragment thereof as is known to the art. So long as the polypeptide has biological activity, it does not need to be a naturally-occurring polypeptide, but may be mutated, truncated, or otherwise modified. Such biologically active polypeptides may be modified polypeptides, containing only biologically-active portions of biologically-active polypeptides. They may also be amino acid sequences homologous to naturally-occurring biologically-active amino acid sequences (preferably at least about 75% homologous) which retain biological activity.

The starch-encapsulating region of the hybrid polypeptide may be a starch-encapsulating region of any starch-binding enzyme known to the art, e.g. an enzyme selected from the group consisting of soluble starch synthase I, soluble starch synthase II, soluble starch synthase III, granule-bound starch synthase, branching enzyme I, branching enzyme IIa, branching enzyme IIBb and glucoamylase polypeptides.

When the hybrid polypeptide is to be used to produce payload polypeptide in pure or partially purified form, the hybrid polypeptide preferably comprises a cleavage site between the starch-encapsulating region and the payload polypeptide. The method of isolating the purified payload polypeptide then includes the step of contacting the hybrid polypeptide with a cleaving agent specific for that cleavage site.

This invention also provides recombinant nucleic acid (RNA or DNA) molecules encoding the hybrid polypeptides. Such recombinant nucleic acid molecules preferably comprise control sequences adapted for expression of the hybrid polypeptide in the selected host. The term "control sequences" includes promoters, introns, preferred codon sequences for the particular host organism, and other sequences known to the art to affect expression of DNA or RNA in particular hosts. The nucleic acid sequences encoding the starch-encapsulating region and the payload polypeptide may be naturally-occurring nucleic acid sequences, or biologically-active fragments thereof, or may be biologically-active sequences homologous to such sequences, preferably at least about 75% homologous to such sequences.

Host organisms include bacteria, plants, and animals. Preferred hosts are plants. Both monocotyledonous plants (monocots) and dicotyledonous plants (dicots) are useful hosts for expressing the hybrid polypeptides of this invention.

This invention also provides expression vectors comprising the nucleic acids encoding the hybrid proteins of this invention. These expression vectors are used for transforming the nucleic acids into host organisms and may also comprise sequences aiding in the expression of the nucleic acids in the host organism. The expression vectors may be plasmids, modified viruses, or DNA or RNA molecules, or other vectors useful in transformation systems known to the art.

By the methods of this invention, transformed cells are produced comprising the recombinant nucleic acid molecules capable of expressing the hybrid polypeptides of this invention. These may be prokaryotic or eukaryotic cells from unicellular organisms, plants or animals. They may be bacterial cells from which the hybrid polypeptide may be harvested. Or, they may be plant cells which may be regenerated into plants from which the hybrid polypeptide may be harvested, or, such plant cells may be regenerated into fertile plants with seeds containing the nucleic acids encoding the hybrid polypeptide. In a preferred embodiment, such seeds contain modified starch comprising the payload polypeptide.

The term "modified starch" means the naturally-occurring starch has been modified to comprise the payload polypeptide.

A method of targeting digestion of a payload polypeptide to a particular phase of the digestive process, e.g., preventing degradation of a payload polypeptide in the stomach of an animal, is also provided comprising feeding the animal a modified starch of this invention comprising the payload polypeptide, whereby the polypeptide is protected by the starch from degradation in the stomach of the animal. Alternatively, the starch may be one known to be digested in the stomach to release the payload polypeptide there.

Preferred recombinant nucleic acid molecules of this invention comprise DNA encoding starch-encapsulating regions selected from the starch synthesizing gene sequences set forth in the tables hereof.

Preferred plasmids of this invention are adapted for use with specific hosts. Plasmids comprising a promoter, a plastid-targeting sequence, a nucleic acid sequence encoding a starch-encapsulating region, and a terminator sequence, are provided herein. Such plasmids are suitable for insertion of DNA sequences encoding payload polypeptides and starch-encapsulating regions for expression in selected hosts.

Plasmids of this invention can optionally include a spacer or a linker unit proximate the fusion site between nucleic acids encoding the SER and the nucleic acids encoding the payload polypeptide. This invention includes plasmids comprising promoters adapted for a prokaryotic or eukaryotic hosts. Such promoters may also be specifically adapted for expression in monocots or in dicots.

A method of forming peptide-modified starch of this invention includes the steps of: supplying a plasmid having a promoter associated with a nucleic acid sequence encoding a starch-encapsulating region, the nucleic acid sequence encoding the starch-encapsulating region being connected to a nucleic acid region encoding a payload polypeptide, and transforming a host with the plasmid whereby the host expresses peptide-modified starch.

This invention furthermore comprises starch-bearing grains comprising: an embryo, nutritive tissues; and, modified starch granules having encapsulated therein a protein that is not endogenous to starch granules of said grain which are not modified. Such starch-bearing grains may be grains wherein the embryo is a maize embryo, a rice embryo, or a wheat embryo.

All publications referred to herein are incorporated by reference to the extent not inconsistent herewith.

BRIEF DESCRIPTION OF THE DRAWINGS

FIG. 7A shows pEXS adh1. FIG. 7B shows pEXS adh1-nos3'. FIG. 7C shows pEXS33. FIG. 7D shows pEXS10zp. FIG. 73 shows pEXS10zp-adh1. FIG. 7F shows pEXS10zp-adh1-nos3'.

DETAILED DESCRIPTION

Figure 1A:
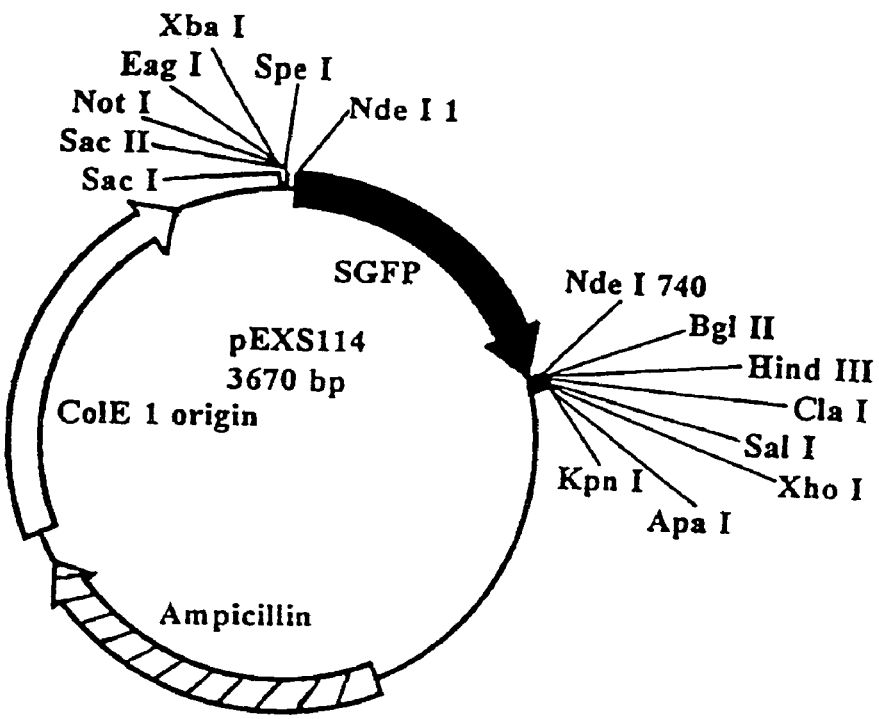
FIG. 1A shows the plasmid pEXS114 which contains the synthetic GFP (Green Fluorescent Protein) subcloned into pBSK from Stratagene.

The present invention provides, broadly, a hybrid polypeptide, a method for making a hybrid polypeptide, and nucleic acids encoding the hybrid polypeptide. A hybrid polypeptide consists of two or more subparts fused together into a single peptide chain. The subparts can be amino acids or peptides or polypeptides. One of the subparts is a starch-encapsulating region. Hybrid polypeptides may thus be targeted into starch granules produced by organisms expressing the hybrid polypeptides.

A method of making the hybrid polypeptides within cells involves the preparation of a DNA construct comprising at least a fragment of DNA encoding a sequence which functions to bind the expression product of attached DNA into a granule of starch, ligated to a DNA sequence encoding the polypeptide of interest (the payload polypeptide). This construct is expressed within a eukaryotic or prokaryotic cell. The hybrid polypeptide can be used to produce purified protein or to immobilize a protein of interest within the protection of a starch granule, or to produce grain that contains foreign amino acids or peptides.

| The hybrid polypeptide according to the present invention has three regions. | | |
|---|---|---|
| Payload Peptide (X) | Central Site (CS)* | Starch-encapsulating region (SER) |

X is any amino acid or peptide of interest.
*optional component.

The gene for X can be placed in the 5' or 3' position within the DNA construct described below.

CS is a central site which may be a leaving site, a cleavage site, or a spacer, as is known to the art. A cleavage site is recognized by a cleaving enzyme. A cleaving enzyme is an enzyme that cleaves peptides at a particular site. Examples of chemicals and enzymes that have been employed to cleave polypeptides include thrombin, trypsin, cyanobromide, formic acid, hydroxyl amine, collagenase, and ala-subtilisin. A spacer is a peptide that joins the peptides comprising the hybrid polypeptide. Usually it does not have any specific activity other than to join the peptides or to preserve some minimum distance or to influence the folding, charge or water acceptance of the protein. Spacers may be any peptide sequences not interfering with the biological activity of the hybrid polypeptide.

The starch-encapsulating region (SER) is the region of the subject polypeptide that has a binding affinity for starch. Usually the SER is selected from the group consisting of peptides comprising starch-binding regions of starch synthases and branching enzymes of plants, but can include starch binding domains from other sources such as glucoamylase and the like. In the preferred embodiments of the invention, the SER includes peptide products of genes that naturally occur in the starch synthesis pathway. This subset of preferred SERs is defined as starch-forming encapsulating regions (SFER). A further subset of SERs preferred herein is the specific starch-encapsulating regions (SSER) from the specific enzymes starch synthase (STS), granule-bound starch synthase (GBSTS) and branching enzymes (BE) of starch-bearing plants. The most preferred gene product from this set is the GBSTS. Additionally, starch synthase I and branching enzyme II are useful gene products. Preferably, the SER (and all the subsets discussed above) are truncated versions of the full length starch synthesizing enzyme gene such that the truncated portion includes the starch-encapsulating region.

The DNA construct for expressing the hybrid polypeptide within the host, broadly is as follows:

| Promoter | Intron* | Transit Peptide Coding Region* | X | SER | Terminator |
|---|---|---|---|---|---|

*optional component. Other optional components can also be used.

As is known to the art, a promoter is a region of DNA controlling transcription. Different types of promoters are selected for different hosts. Lac and T7 promoters work well in prokaryotes, the 35S CaMV promoter works well in dicots, and the polyubiquitin promoter works well in many monocots. Any number of different promoters are known to the art and can be used within the scope of this invention.

Also as is known to the art, an intron is a nucleotide sequence in a gene that does not code for the gene product. One example of an intron that often increases expression in monocots is the Adh1 intron. This component of the construct is optional.

The transit peptide coding region is a nucleotide sequence that encodes for the translocation of the protein into organelles such as plastids. It is preferred to choose a transit peptide that is recognized and compatible with the host in which the transit peptide is employed. In this invention the plastid of choice is the amyloplast.

It is preferred that the hybrid polypeptide be located within the amyloplast in cells such as plant cells which synthesize and store starch in amyloplasts. If the host is a bacterial or other cell that does not contain an amyloplast, there need not be a transit peptide coding region.

A terminator is a DNA sequence that terminates the transcription.

X is the coding region for the payload polypeptide, which may be any polypeptide of interest, or chains of amino acids. It may have up to an entire sequence of a known polypeptide or comprise a useful fragment thereof. The payload polypeptide may be a polypeptide, a fragment thereof, or biologically active protein which is an enzyme, hormone, growth factor, immunoglobulin, dye, etc. Examples of some of the payload polypeptides that can be employed in this invention include, but are not limited to, prolactin (PRL), serum albumin, growth factors and growth hormones, i.e., somatotropin. Serum albumins include bovine, ovine, equine, avian and human serum albumin. Growth factors include epidermal growth factor (EGF), insulin-like growth factor I (IGF-I), insulin-like growth factor II (IGF-II), fibroblast growth factor (FGF), transforming growth factor alpha (TGF-alpha), transforming growth factor beta (TGF-beta), nerve growth factor (NGF), platelet-derived growth factor (PDGF), and recombinant human insulin-like growth factors I (rHuIGF-I) and II (rHuIGF-II). Somatotropins which can be employed to practice this invention include, but are not limited to, bovine, porcine, ovine, equine, avian and human somatotropin. Porcine somatotropin includes delta-7 recombinant porcine somatotropin, as described and claimed in European Patent Application Publication No. 104,920 (Biogen). Preferred payload polypeptides are somatotropin, insulin A and B chains, calcitonin, beta endorphin, urogastrone, beta globin, myoglobin, human growth hormone, angiotensin, proline, proteases, beta-galactosidase, and cellulases.

The hybrid polypeptide, the SER region and the payload polypeptides may also include post-translational modifications known to the art such as glycosylation, acylation, and other modifications not interfering with the desired activity of the polypeptide.

Developing a Hybrid Polypeptide

The SER region is present in genes involved in starch synthesis. Methods for isolating such genes include screening from genomic DNA libraries and from cDNA libraries. Genes can be cut and changed by ligation, mutation agents, digestion, restriction and other such procedures, e.g., as outlined in Maniatis et al., Molecular Cloning, Cold Spring Harbor Labs, Cold Spring Harbor, N.Y. Examples of excellent starting materials for accessing the SER region include, but are not limited to, the following: starch synthases I, II, III, IV, Branching Enzvmes I, IIA and B and granule-bound starch synthase (GBSTS). These genes are present in starch-bearing plants such as rice, maize, peas, potatoes, wheat, and the like. Use of a probe of SER made from genomic DNA or cDNA or mRNA or antibodies raised against the SER allows for the isolation and identification of useful genes for cloning. The starch enzyme-encoding sequences may be modified as long as the modifications do not interfere with the ability of the SER region to encapsulate associated polypeptides.

When genes encoding proteins that are encapsulated into the starch granule are located, then several approaches to isolation of the SER can be employed, as is known to the art. One method is to cut the gene with restriction enzymes at various sites, deleting sections from the N-terminal end and allowing the resultant protein to express. The expressed truncated protein is then run on a starch gel to evaluate the association and dissociation constant of the remaining protein. Marker genes known to the art, e.g., green fluorescent protein gene, may be attached to the truncated protein and used to determine the presence of the marker gene in the starch granule.

Once the SER gene sequence region is isolated it can be used in making the gene fragment sequence that will express the payload polypeptide encapsulated in starch. The SER gene sequence and the gene sequence encoding the payload polypeptide can be ligated together. The resulting fused DNA can then be placed in a number of vector constructs for expression in a number of hosts. The preferred hosts form starch granules in plastids, but the testing of the SER can be readily performed in bacterial hosts such as *E. coli.*

The nucleic acid sequence coding for the payload polypeptide may be derived from DNA, RNA, genomic DNA, cDNA, mRNA or may be synthesized in whole or in part. The sequence of the payload polypeptide can be manipulated to contain mutations such that the protein produced is a novel, mutant protein, so long as biological function is maintained.

When the payload polypeptide-encoding nucleic acid sequence is ligated onto the SER-encoding sequence, the gene sequence for the payload polypeptide is preferably attached at the end of the SER sequence coding for the N-terminus. Although the N-terminus end is preferred, it does not appear critical to the invention whether the payload polypeptide is ligated onto the N-terminus end or the C-terminus end of the SER. Clearly, the method of forming the recombinant nucleic acid molecules of this invention, whether synthetically, or by cloning and ligation, is not critical to the present invention.

The central region of the hybrid polypeptide is optional. For some applications of the present invention it can be very useful to introduce DNA coding for a convenient protease cleavage site in this region into the recombinant nucleic acid molecule used to express the hybrid polypeptide. Alternatively, it can be useful to introduce DNA coding for an amino acid sequence that is pH-sensitive to form the central region. If the use of the present invention is to develop a pure protein that can be extracted and released from the starch granule by a protease or the like, then a protease cleavage site is useful. Additionally, if the protein is to be digested in an animal then a protease cleavage site may be useful to assist the enzymes in the digestive tract of the animal to release the protein from the starch. In other applications and in many digestive uses the cleavage site would be superfluous.

The central region site may comprise a spacer. A spacer refers to a peptide that joins the proteins comprising a hybrid polypeptide. Usually it does not have any specific activity other than to join the proteins, to preserve some minimum distance, to influence the folding, charge or hydrophobic or hydrophilic nature of the hybrid polypeptide.

Construct Development

Once the ligated DNA which encodes the hybrid polypeptide is formed, then cloning vectors or plasmids are prepared which are capable of transferring the DNA to a host for expressing the hybrid polypeptides. The recombinant nucleic acid sequence of this invention is inserted into a convenient cloning vector or plasmid. For the present invention the preferred host is a starch granule-producing host. However, bacterial hosts can also be employed. Especially useful are bacterial hosts that have been transformed to contain some or all of the starch-synthesizing genes of a plant. The ordinarily skilled person in the art understands that the plasmid is tailored to the host. For example, in a bacterial host transcriptional regulatory promoters include lac, TAC (a functional hybrid derived from the TRP and lac promoters), trp and the like. Addtionally, DNA coding for a transit peptide most likely would not be used and a secretory leader that is upstream from the structural gene may be used to get the polypeptide into the medium. Alternatively, the product is retained in the host and the host is lysed and the product isolated and purified by starch extraction methods or by binding the material to a starch matrix (or a starch-like matrix such as amylose or amylopectin, glycogen or the like) to extract the product.

The preferred host is a plant and thus the preferred plasmid is adapted to be useful in a plant. The plasmid should contain a promoter, preferably a promoter adapted to target the expression of the protein in the starch-containing tissue of the plant. The promoter may be specific for various tissues such as seeds, roots, tubers and the like; or, it can be a constitutive promoter for gene expression throughout the tissues of the plant. Well-known promoters include the 10 kD zein (maize) promoter, the CAB (chlorophyll a/b binding protein) promoter, patatin, 35S and 19S cauliflower mosaic virus promoters (very useful in dicots), the polyubiquitin promoter (useful in monocots) and enhancements and modifications thereof known to the art.

The cloning vector may contain coding sequences for a transit peptide to direct the plasmid into the correct location. Examples of transit peptide-coding sequences are shown in the sequence tables. Coding sequences for other transit peptides can be used. Transit peptides naturally occurring in the host to be used are preferred. Preferred transit peptide coding regions for maize are shown in the tables and figures hereof. The purpose of the transit peptide is to target the vector to the correct intracellular area.

Attached to the transit peptide-encoding sequence is the DNA sequence encoding the N-terminal end of the payload polypeptide. The direction of the sequence encoding the payload polypeptide is varied depending on whether sense or antisense transcription is desired. DNA constructs of this invention specifically described herein have the sequence encoding the payload polypeptide at the N-terminus end but the SER coding region can also be at the N-terminus end and the payload polypeptide sequence following. At the end of the DNA construct is the terminator sequence. Such sequences are well known in the art.

The cloning vector is transformed into a host. Introduction of the cloning vector, preferably a plasmid, into the host can be done by a number of transformation techniques known to the art. These techniques may vary by host but they include microparticle bombardment, micro injection, *Agrobacterium* transformation, "whiskers" technology (U.S. Pat. Nos. 5,302,523 and 5,464,765), electroporation and the like. If the host is a plant, the cells can be regenerated to form plants. Methods of regenerating plants are known in the art. Once the host is transformed and the proteins expressed therein, the presence of the DNA encoding the payload polypeptide in the host is confirmable. The presence of expressed proteins may be confirmed by Western Blot or ELISA or as a result of a change in the plant or the cell.

Uses of Encapsulated Protein

There are a number of applications of this invention. The hybrid polypeptide can be cleaved in a pure state from the starch (cleavage sites can be included) and pure protein can be recovered. Alternatively, the encapsulated payload polypeptide within the starch can be used in raw form to deliver protein to various parts of the digestive tract of the consuming animal ("animal" shall include mammals, birds and fish). For example if the starch in which the material is encapsulated is resistant to digestion then the protein will be released slowly into the intestine of the animal, therefore avoiding degradation of the valuable protein in the stomach. Amino acids such as methionine and lysine may be encapsulated to be incorporated directly into the grain that the animal is fed thus eliminating the need for supplementing the diet with these amino acids in other forms.

The present invention allows hormones, enzymes, proteins, proteinaceous nutrients and proteinaceous medicines to be targeted to specific digestive areas in the digestive tracts of animals. Proteins that normally are digested in the upper digestive tract encapsulated in starch are able to pass through the stomach in a nondigested manner and be absorbed intact or in part by the intestine. If capable of passing through the intestinal wall, the payload polypeptides can be used for medicating an animal, or providing hormones such as growth factors, e.g., somatotropin, for vaccination of an animal or for enhancing the nutrients available to an animal.

If the starch used is not resistant to digestion in the stomach (for example the sugary 2 starch is highly digestible), then the added protein can be targeted to be absorbed in the upper digestive tract of the animal. This would require that the host used to produce the modified starch be mutated or transformed to make sugary 2 type starch. The present invention encompasses the use of mutant organisms that form modified starch as hosts. Some examples of these mutant hosts include rice and maize and the like having sugary 1, sugary 2, brittle, shrunken, waxy, amylose extender, dull, opaque, and floury mutations, and the like. These mutant starches and starches from different plant sources have different levels of digestibility. Thus by selection of the host for expression of the DNA and of the animal to which the modified starch is fed, the hybrid polypeptide can be digested where it is targeted. Different proteins are absorbed most efficiently by different parts of the body. By encapsulating the protein in starch that has the selected digestibility, the protein can be supplied anywhere throughout the digestive tract and at specific times during the digestive process.

Another of the advantages of the present invention is the ability to inhibit or express differing levels of glycosylation of the desired polypeptide. The encapsulating procedure may allow the protein to be expressed within the granule in a different glycosylation state than if expressed by other DNA molecules. The glycosylation will depend on the amount of encapsulation, the host employed and the sequence of the polypeptide.

Improved crops having the above-described characteristics may be produced by genetic manipulation of plants known to possess other favorable characteristics. By manipulating the nucleotide sequence of a starch-synthesizing enzyme gene, it is possible to alter the amount of key amino acids, proteins or peptides produced in a plant. One or more genetically engineered gene constructs, which may be of plant, fungal, bacterial or animal origin, may be incorporated into the plant genome by sexual crossing or by transformation. Engineered genes may comprise additional copies of wildtype genes or may encode modified or allelic or alternative enzymes with new properties. Incorporation of such gene construct(s) may have varying effects depending on the amount and type of gene(s) introduced (in a sense or antisense orientation). It may increase the plant's capacity to produce a specific protein, peptide or provide an improved amino acid balance.

Cloning Enzymes Involved in Starch Biosynthesis

Known cloning techniques may be used to provide the DNA constructs of this invention. The source of the special forms of the SSTS, GBSTS, BE, glycogen synthase (GS), amylopectin, or other genes used herein may be any organism that can make starch or glycogen. Potential donor organisms are screened and identified. Thereafter there can be two approaches: (a) using enzyme purification and antibody/sequence generation following the protocols described herein; (b) using SSTS, GBSTS, BE, GS, amylopectin or other cDNAs as heterologous probes to identify the genomic DNAs for SSTS, GBSTS, BE, GS, amylopectin or other starch-encapsulating enzymes in libraries from the organism concerned. Gene transformation, plant regeneration and testing protocols are known to the art. In this instance it is necessary to make gene constructs for transformation which contain regulatory sequences that ensure expression during starch formation. These regulatory sequences are present in many small grains and in tubers and roots. For example these regulatory sequences are readily available in the maize endosperm in DNA encoding Granule Bound Starch Synthesis (GBSTS), Soluble Starch Synthases (SSTS) or Branching Enzymes (BE) or other maize endosperm starch synthesis pathway enzymes. These regulatory sequences from the endosperm ensure protein expression at the correct developmental time (e.g., ADPG pyrophosphorylase).

In this method we measure starch-binding constants of starch-binding proteins using native protein electrophoresis in the presence of suitable concentrations of carbohydrates such as glycogen or amylopectin. Starch-encapsulating regions can be elucidated using site-directed mutagenesis and other genetic engineering methods known to those skilled in the art. Novel genetically-engineered proteins carrying novel peptides or amino acid combinations can be evaluated using the methods described herein.

EXAMPLES

Example One

Method for Identification of Starch-encapsulating Proteins

Starch-Granule Protein Isolation:

Homogenize 12.5 g grain in 25 ml Extraction buffer (50 mM Tris acetate, pH 7.5, 1 mM EDTA, 1 mM DTT for 3×20 seconds in Waring blender with 1 min intervals between blending). Keep samples on ice. Filter through mira cloth and centrifuge at 6,000 rpm for 30 min. Discard supernatant and'scrape off discolored solids which overlay white starch pellet. Resuspend pellet in 25 ml buffer and recentrifuge. Repeat washes twice more. Resuspend washed pellet in −20° C. acetone, allow pellet to settle at −20° C. Repeat. Dry starch under stream of air. Store at −20° C.

Protein Extraction:

Mix 50 mg starch with 1 ml 2% SDS in eppendorf. Vortex, spin at 18,000 rpm, 5 min, 4° C. Pour off supernatant. Repeat twice. Add 1 ml sample buffer (4 ml distilled water, 1 ml 0.5 M Tris-HCl, pH 6.8, 0.8 ml glycerol, 1.6 ml 10% SDS, 0.4 ml B-mercaptoethanol, 0.2 ml 0.5% bromphenol blue). Boil eppendorf for 10 min with hole in lid. Cool, centrifuge 10,000 rpm for 10 min. Decant supernatant into new eppendorf. Boil for 4 minutes with standards. Cool.

| SDS-Page Gels: (non-denaturing) | | |
|---|---|---|
| | 10% Resolve | 4% Stack |
| Acryl/Bis 40% stock | 2.5 ml | 1.0 ml |
| 1.5 M Tris pH 8.8 | 2.5 ml | — |
| 0.5 M Tris pH 8.8 | — | 2.5 ml |
| 10% SDS | 100 µl | 100 µl |
| Water | 4.845 ml | 6.34 ml |
| Degas 15 min add fresh | | |
| 10% Ammonium Persulfate | 50 µl | 50 µl |
| TEMED | 5 µl | 10 µl |

Mini-Protean II Dual Slab Cell; 3.5 ml of Resolve buffer per gel. 4% Stack is poured on top. The gel is run at 200V constant voltage. 10×Running buffer (250 mM Tris, 1.92 M glycine, 1% SDS, pH 8.3).

| Method of Measurement of Starch-Encapsulating Regions: | |
|---|---|
| Solutions: | |
| Extraction Buffer: | 50 mM Tris-acetate pH 7.5, 10 mM EDTA, 10% sucrose, 2.5 mM DTT-fresh. |
| Stacking Buffer: | 0.5 M Tris-HCl, pH 6.8 |
| Resolve Buffer: | 1.5 M Tris-HCl, pH 8.8 |
| 10 × Lower Electrode Buffer: | 30.3 g Tris + 144 g Glycine qs to 1 L. (pH is ~8.3, no adjustment). Dilute for use. |
| Upper Electrode Buffer: | Same as Lower |
| Sucrose Solution: | 18.66 g sucrose + 100 ml dH₂O |
| 30% Acryl/Bis Stock (2.67% C): | 146 g acrylamide + 4 g bis + 350 ml dH₂O. Bring up to 500 ml. Filter and store at 4 C in the dark for up to 1 month. |
| 15% Acryl/Bis Stock (20% C): | 6 g acrylamide + 1.5 g bis + 25 ml dH₂O. Bring up to 50 ml. Filter and store at 4 C in the dark for up to 1 month. |
| Riboflavin | 1.4 g riboflavin + 100 ml dH₂O. Store in dark for up |

-continued

Method of Measurement of Starch-Encapsulating Regions:

Solutions:

| Solution: | to 1 month. |
|---|---|
| SS Assay mix: | 25 mM Sodium Citrate, 25 mM Bicine-NaO (pH 8.0), 2 mM EDTA, 1 mM DTT-fresh, 1 mM Adenosine 5' Diphosphoglucose-fresh, 10 mg/ml rabbit liver glycogen Type III-fresh. |
| Iodine Solution: | 2 g iodine + 20 g KI, 0.1 N HCl up to 1 L. |

Extract:
 4 ml extraction buffer+12 g endosperm. Homogenize.
 filter through mira cloth or 4 layers cheesecloth, spin 20,000 g (14,500 rpm, SM-24 rotor), 20 min., 4° C.
 remove supernatant using a glass pipette.
 0.85 ml extract+0.1 ml glycerol+0.05 ml 0.5% bromophenol blue.
 vortex and spin 5 min. full speed microfuge. Use directly or freeze in liquid nitrogen and store at −80° C. for up to 2 weeks.

Cast Gels:
 Attach Gel Bond PAG film (FIfC Industries, Rockland, Me.) to (inside of) outer glass plate using two-sided scotch tape, hydrophilic side up. The tape and the film is lined up as closely and evenly as possible with the bottom of the plate. The film is slightly smaller than the plate. Squirt water between the film and the plate to adhere the film. Use a tissue to push out excess water. Set up plates as usual, then seal the bottom of the plates with tacky adhesive. The cassette will fit into the casting stand if the gray rubber is removed from the casting stand. The gel polymerizes with the film, and stays attached during all subsequent manipulations.

Cast 4.5% T resolve mini-gel (0.75 mm): 2.25 ml dH$_2$O
 +3.75 ml sucrose solution
 +2.5 ml resolve buffer
 +1.5 ml 30% Acryl/Bis stock
 +various amounts of glycogen for each gel (i.e., 0–1.0%)
 DEGAS 15 NIN.
 +50 µl 10% APS
 +5 µl TEMED
 POLYMERIZE FOR 30 NIN. OR OVERNIGHT Cast 3.125% T stack: 1.59 ml dH$_2$O
 +3.75 ml sucrose solution
 +2.5 ml stack buffer
 +2.083 ml 15% Acryl/Bis stock
 DO NOT DEGAS
 15 µl 10% APS
 +35 µl riboflavin solution
 +30 µl TEMED
 POLYMERIZE FOR 2.5 HOURS CLOSE TO A LIGHT BULB cool in 4° C. before pulling out combs. Can also not use combs, and just cast a centimeter of stacker.

The Foregoing Procedure:
 Can run at different temperatures; preincubate gels and solutions.
 Pre-run for 15 min. at 200 V
 Load gel: 7 µl per well, or 115 µl if no comb.
 Run at 140 V until dye front is close to bottom. Various running temperatures are achieved by placing the whole gel rig into a water bath. Can occasionally stop the run to insert a temperature probe into the gel.

Enzyme assay: Cut gels off at dye front. Incubate in SS. Assay mix overnight at room temperature with gentle shaking. Rinse gels with water. Flood with I2/KI solution.

Take pictures of the gels on a light box, and measure the pictures. Rm=mm from top of gel to the active band/ mm from top of gel to the bottom of the gel where it was cut (where the dye front was). Plot % glycogen vs. 1/Rm. The point where the line intersects the x axis is −K (where y=0).

Testing and Evaluation Protocol for SER Region Length:
 Following the procedure above for selection of the SER region requires four basic steps. First DNA encoding a protein having a starch-encapsulation region must be selected. This can be selected from known starch-synthesizing genes or starch-binding genes such as genes for amylases, for example. The protein must be extracted. A number of protein extraction techniques are well known in the art. The protein may be treated with proteases to form protein fragments of different lengths. The preferred fragments have deletions primarily from the N-terminus region of the protein. The SER region is located nearer to the C-terminus end than the N-terminus end. The protein is run on the gels described above and affinity for the gel matrix is evaluated. Higher affinity shows more preference of that region of the protein for the matrix. This method enables comparison of different proteins to identify the starch-encapsulating regions in natural or synthetic proteins.

Example Two

Figure 1B:
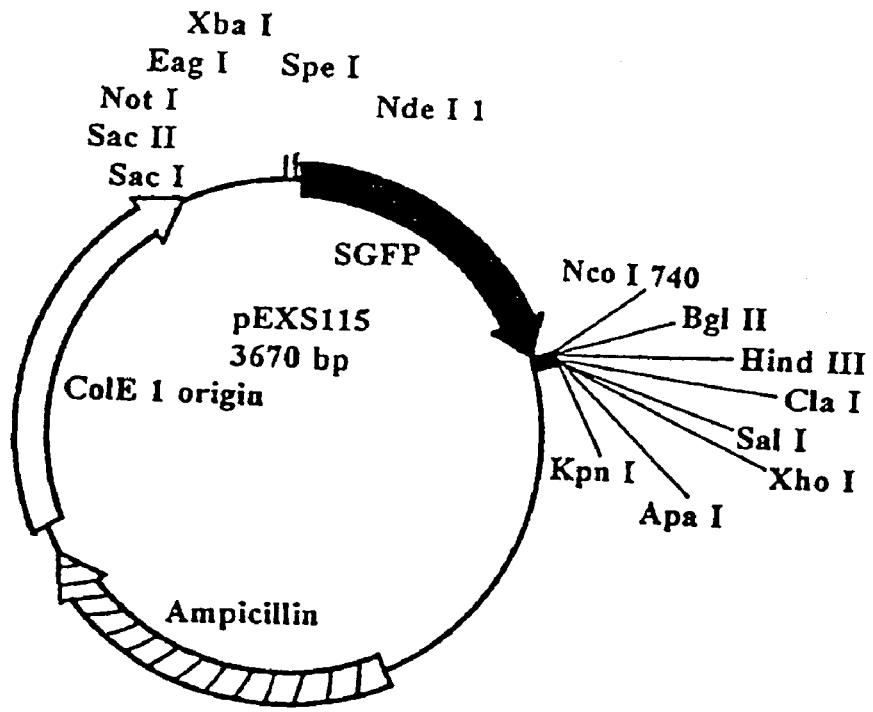
FIG. 1B shows the plasmid pEXS115.
Figure 2A:
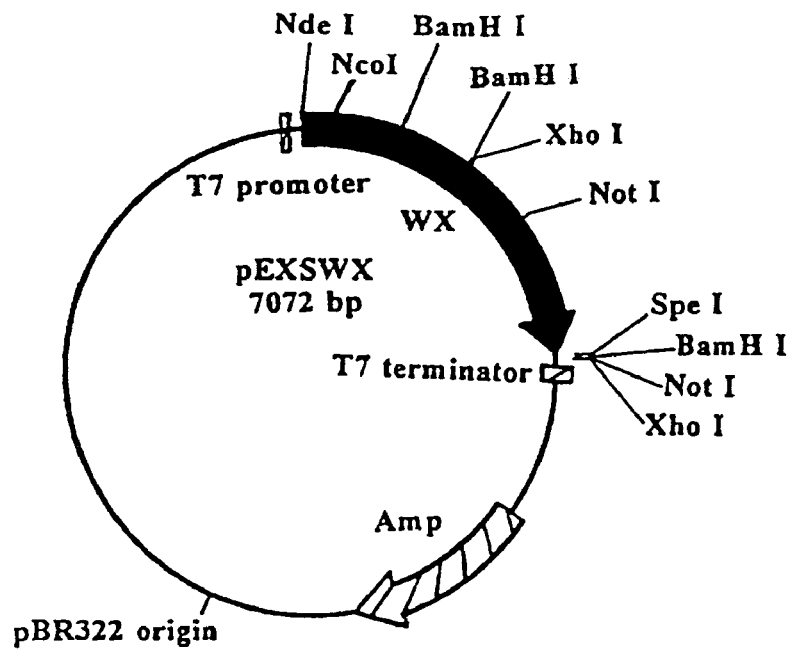
FIG. 2A shows the waxy gene with restriction sites subcloned into a commercially available plasmid.
Figure 2B:
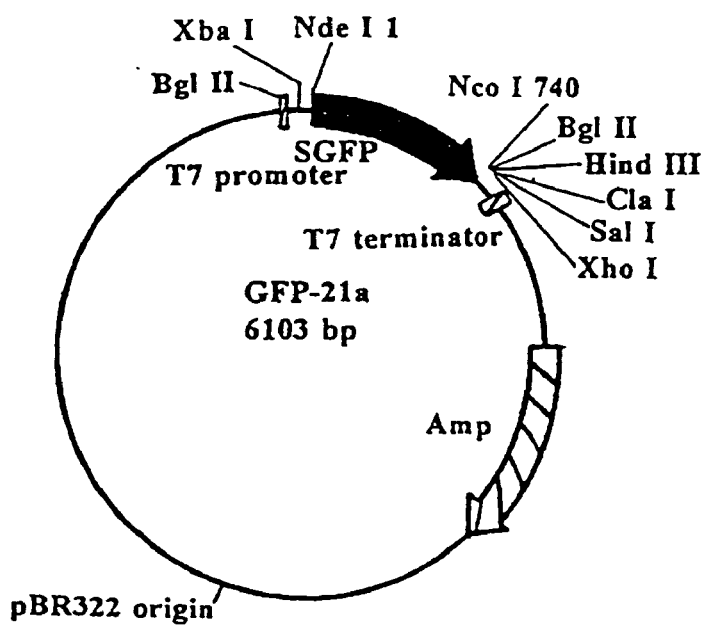
FIG. 2B shows the p ET-21A plasmid commercially available from Novagen having the GFP fragment from pEXS115 subcloned therein.

SER Fusion Vector:
 The following fusion vectors are adapted for use in *E. coli*. The fusion gene that was attached to the probable SER in these vectors encoded for the green fluorescent protein (GFP). Any number of different genes encoding for proteins and polypeptides could be ligated into the vectors. A fusion vector was constructed having the SER of waxy maize fused to a second gene or gene fragment, in this case GFP.

pEXS114 (see FIG. 1*a*): Synthetic GFP (SGFP) was PCR-amplified from the plasmid HBT-SGFP (from Jen Sheen; Dept. of Molecular Biology; Wellman 11, MGH; Boston, Mass. 02114) using the primers EXS73 (5'-GAC-TAGTCATATG GTG AGC AAG GGC GAG GAG-3') [SEQ ID NO:1] and EXS74 (5'-CTAGATCTTCATATG CTT GTA CAG CTC GTC CAT GCC-3') [SEQ ID NO:2]. The ends of the PCR product were polished off with T DNA polymerase to generate blunt ends; then the PCR product was digested with Spe I. This SGFP fragment was subcloned into the EcoRV-Spe I sites of pBSK (Stratagene at 11011 North Torrey Pines Rd. La Jolla, Calif.) to generate pEXS114.

pEXS115 [see FIG. 1*b*]: Synthetic GFP (SGFP) was PCR-amplified from the plasmid HBT-SGFP (from Jen Sheen) using the primers EXS73 (see above) and EXS75 (5'-CTAGATCTTGGCCATGGC CTT GTA CAG CTC GTC CAT GCC-3') [SEQ ID NO:3]. The ends of the PCR product were polished off with T DNA polymerase to generate blunt ends; then the PCR product was digested with Spe I. This SGFP fragment was subcloned into the EcoRV-Spe I sites of pBSK (Stratagene) generating pEXSI 115.

pEXSWX (see FIG. 2*a*): Maize WX subcloned NdeI-Not I into pET-21a (see FIG. 2*b*). The genomic DNA sequence and associated amino acids from which the mRNA sequence can be generated is shown in TABLES 1a and 1b below and alternatively the DNA listed in the following tables could be employed.

TABLE 1a

DNA Sequence and Deduced Amino Acid Sequence
of the waxy Gene in Maize
[SEQ ID NO:4 and SEQ ID NO:5]

```
LOCUS        ZMWAXY       4800 bp    DNA            PLN
DEFINITION   Zea mays waxy (wx+) locus for UDP-glucose starch glycosyl
             transferase.
ACCESSION    X03935 M24258
KEYWORDS     glycosyl transferase; transit peptide;
             UDP-glucose starch glycosy). transferase; waxy locus.
SOURCE       maize.
ORGANISM     Zea mays
             Eukaryota; Plantae; Embryobionta; Magnoliophyta; Liliopsida;
             Commelinidae; Cyperales; Poaceae.
REFERENCE    1 (bases 1 to 4800)
AUTHORS      Kloesgen, R. B., Gierl, A., Schwarz-Sommer, Z. and Saedler, H.
TITLE        Molecular analysis of the waxy locus of Zea mays
JOURNAL      Mol. Gen. Genet. 203, 227-244 (1986)
STANDARD     full automatic
COMMENT      NCBI gi: 22509
FEATURES             Location/Qualifiers
     source          1 . . . 4800
                     /organism=Zea mays"
     repeat_region   283 . . . 287
                     /note="direct repeat 1"
     repeat_region   288 . . . 292
                     /note="direct repeat 1"
     repeat_region   293 . . . 297
                     /note="direct repeat 1"
     repeat_region   298 . . . 302
                     /note="direct repeat 1"
     misc_feature    372 . . . 385
                     /note="GC stretch (pot. regulatory factor binding site)"
     misc_feature    442 . . . 468
                     /note="GC stretch (pot. regulatory factor binding site)"
     misc_feature    768 . . . 782
                     /note="GC stretch (pot. regulatory factor binding site)"
     misc_feature    810 . . . 822
                     /note="GC stretch (pot. regulatory factor binding site)"
     misc_feature    821 . . . 828
                     /note="target duplication site (Ac7)"
     CAAT_signal     821 . . . 828
     TATA_signal     867 . . . 873
     misc_feature    887 . . . 900
                     /note="GC stretch (pot. regulatory factor binding site)"
     misc_feature    901
                     /note= "transcriptional start site"
     exon            901 . . . 1080
                     /number=1
     intron          1081 . . . 1219
                     /number=1
     exon            1220 . . . 1553
                     /number=2
     transit_peptide 1233 . . . 1448
     CDS             join(1449 . . . 1553, 1685 . . . 1765, 1860 . . . 1958,
2055 . . . 2144, 2226 . . . 2289, 2413 . . . 2513, 2651 . . . 2760, 2858 . . . 3101,
3212 . . . 3394, 3490 . . . 3681, 3793 . . . 3879, 3977 . . . 4105, 4227 . . . 4343)
                     /note="NCBI gi: 22510"
                     /codon_start=1
                     /product="glucosyl transferase"
```

/translation="ASAGMNVVFVGAEMAPWSKTGGLGDVLGGLPPAMAANGHRVMVV

SPRYDQYKDAWDTSVVSEIKMGDGYETVRFFHCYKRGVDRVFVDHPLFLERVWGKTEE

KIYGPVAGTDYRDNQLRFSLLCQAALEAPRILSLNNNPYFSGPYGEDVVFVCNDWHTG

PLSCYLKSNYQSHGIYRDAKTAFCIHNISYQGRFAFSDYPELNLPERFKSSFDFIDGY

EKPVEGRKINWMKAGILEADRVLTVSPYYAEELISGIARGCELDNIMRLTGITGIVNG

MDVSEWDPSRDKYIAVKYDVSTAVEAKALNKEALQAEVGLPVDRNIPLVAFIGRLEEQ

KGPDVMAAAIPQLMEMVEDVQIVLLGTGKKKFERMLMSAEEKFPGKVRAVVKFNAALA

HHIMAGADVLAVTSRFEPCGLIQLQGMRYGTPCACASTGGLVDTIIEGKTGFHMGRLS

TABLE 1a-continued

DNA Sequence and Deduced Amino Acid Sequence
of the waxy Gene in Maize
[SEQ ID NO:4 and SEQ ID NO:5]

VDCNVVEPADVKKVATTLQRAIKVVGTPAYEEMVRNCMIQDLSWKGPAKNWENVLLSL

GVAGGEPGVEGEEIAPLAKENVAAP"

```
        intron              1554 . . . 1684
                            /number=2
        exon                1685 . . . 1765
                            /number=3
        intron              1766 . . . 1859
                            /number=3
        exon                1860 . . . 1958
                            /number=4
        intron              1959 . . . 2054
                            /number=4
        exon                2055 . . . 2144
                            /number=5
        intron              2145 . . . 2225
                            /number=5
        exon                2226 . . . 2289
                            /number=6
        intron              2290 . . . 2412
                            /number=6
        exon                2413 . . . 2513
                            /number=7
        intron              2514 . . . 2650
                            /number=7
        exon                2651 . . . 2760
                            /number=8
        intron              2761 . . . 2857
                            /number=8
        exon                2858 . . . 3101
                            /number=9
        intron              3102 . . . 3211
                            /number=9
        exon                3212 . . . 3394
                            /number=10
        misc_feature        3358 . . . 3365
                            /note="target duplication site (Ac9)"
        intron              3395 . . . 3489
                            /number=10
        exon                3490 . . . 3681
                            /number=11
        misc_feature        3570 . . . 3572
                            /note="target duplication site (Spm 18)"
        intron              3682 . . . 3792
                            /number=11
        exon                3793 . . . 3879
                            /number=12
        intron              3880 . . . 3976
                            /number=12
        exon                3977 . . . 4105
                            /number=13
        intron              4106 . . . 4226
                            /number=13
        exon                4227 . . . 4595
                            /number=14
        polyA_signal        4570 . . . 4575
        polyA_signal        4593 . . . 4598
        polyA_site          4595
        polyA_signal        4597 . . . 4602
        polyA_site          4618
        polyA_site          4625
BASE COUNT       935 A    1413 C    1447 G    1005 T
ORIGIN

1 CAGCGACCTA TTACACAGCC CGCTCGGGCC CGCGACGTCG GGACACATCT TCTTCCCCCT

61 TTTGGTGAAG CTCTGCTCGC AGCTGTCCGG CTCCTTGGAC GTTCGTGTGG CAGATTCATC

121 TGTTGTCTCG TCTCCTGTGC TTCCTGGGTA GCTTGTGTAG TGGAGCTGAC ATGGTCTGAG

181 CAGGCTTAAA ATTTGCTCGT AGACGAGGAG TACCAGCACA GCACGTTGCG GATTTCTCTG

241 CCTGTGAAGT GCAACGTCTA GGATTGTCAC ACGCCTTGGT CGCGTCGCGT CGCGTCGCGT
```

TABLE 1a-continued

DNA Sequence and Deduced Amino Acid Sequence
of the waxy Gene in Maize
[SEQ ID NO:4 and SEQ ID NO:5]

```
 301 CGATGCGGTG GTGAGCAGAG CAGCAACAGC TGGGCGGCCC AACGTTGGCT TCCGTGTCTT
 361 CGTCGTACGT ACGCGCGCGC CGGGGACACG CAGCAGAGAG CGGAGAGCGA GCCGTGCACG
 421 GGGAGGTGGT GTGGAAGTGG AGCCGCGCGC CCGGCCGCCC GCGCCCGGTG GGCAACCCAA
 481 AAGTACCCAC GACAAGCGAA GGCGCCAAAG CGATCCAAGC TCCGGAACGC AACAGCATGC
 541 GTCGCGTCGG AGAGCCAGCC ACAAGCAGCC GAGAACCGAA CCGGTGGGCG ACGCGTCATG
 601 GGACGGACGC GGGCGACGCT TCCAAACGGG CCACGTACGC CGGCGTGTGC GTGCGTGCAG
 661 ACGACAAGCC AAGGCGAGGC AGCCCCCGAT CGGGAAAGCG TTTTGGGCGC GAGCGCTGGC
 721 GTGCGGGTCA GTCGCTGGTG CGCAGTCCCG GGGGAACGG GTATCGTGGG GGGCGCGGGC
 781 GGAGGAGAGC GTGGCGAGGG CCGAGAGCAG CGCGCGGCCG GGTCACGCAA CGCGCCCCAC
 841 GTACTGCCCT CCCCCTCCGC GCGCGCTAGA AATACCGAGG CCTGGACCGG GGGGGGGCCC
 901 CGTCACATCC ATCCATCGAC CGATCGATCG CCACAGCCAA CACCACCCGC CGAGGCGACG
 961 CGACAGCCGC CAGGACGAAG GAATAAACTC ACTGCCAGCC AGTGAAGGGG GAGAAGTGTA
1021 CTGCTCCGTC GACCAGTGCG CGCACCGCCC GGCAGGGCTG CTCATCTCGT CGACGACCAG
1081 GTTCTGTTCC GTTCCGATCC GATCCGATCC TGTCCTTGAG TTTCGTCCAG ATCCTGGCGC
1141 GTATCTGCGT GTTTGATGAT CCAGGTTCTT CGAACCTAAA TCTGTCCGTG CACACGTCTT
1201 TTCTCTCTCT CCTACGCAGT GGATTAATCG GCATGGCGGC TCTGGCCACG TCGCAGCTCG
1261 TCGCAACGCG CGCCGGCCTG GGCGTCCCGG ACGCGTCCAC GTTCCGCCGC GGCGCCGCGC
1321 AGGGCCTGAG GGGGGCCCGG GCGTCGGCGG CGGCGGACAC GCTCAGCATG CGGACCAGCG
1381 CGCGCGCGGC GCCCAGGCAC CAGCAGCAGG CGCGCCGCGG GGGCAGGTTC CCGTCGCTCG
1441 TCGTGTGGGC CAGCGCCGGC ATGAACGTCG TCTTCGTCGG CGCCGAGATG GCGCCGTGGA
1501 GCAAGACCGG CGGCCTCGGC GACGTCCTCG GCGGCCTGCC GCCGGCCATG GCCGTAAGCG
1561 CGCGCACCGA GACATGCATC CGTTGGATCG CGTCTTCTTC GTGCTCTTGC CGCGTGCATG
1621 ATGCATGTGT TTCCTCCTGG CTTGTGTTCG TGTATGTGAC GTGTTTGTTC GGGCATGCAT
1681 GCAGGCGAAC GGGCACCGTG TCATGGTCGT CTCTCCCCGC TACGACCAGT ACAAGGACGC
1741 CTGGGACACC AGCGTCGTGT CCGAGGTACG GCCACCGAGA CCAGATTCAG ATCACAGTCA
1801 CACACACCGT CATATGAACC TTTCTCTGCT CTGATGCCTG CAACTGCAAA TGCATGCAGA
1861 TCAAGATGGG AGACGGGTAC GAGACGGTCA GGTTCTTCCA CTGCTACAAG CGCGGAGTGG
1921 ACCGCGTGTT CGTTGACCAC CCACTGTTCC TGGAGAGGGT GAGACGAGAT CTGATCACTC
1981 GATACGCAAT TACCACCCCA TTGTAAGCAG TTACAGTGAG CTTTTTTTCC CCCCGGCCTG
2041 GTCGCTGGTT TCAGGTTTGG GGAAAGACCG AGGAGAAGAT CTACGGGCCT GTCGCTGGAA
2101 CGGACTACAG GGACAACCAG CTGCGGTTCA GCCTGCTATG CCAGGTCAGG ATGGCTTGGT
2161 ACTACAACTT CATATCATCT GTATGCAGCA GTATACACTG ATGAGAAATG CATGCTGTTC
2221 TGCAGGCAGC ACTTGAAGCT CCAAGGATCC TGAGCCTCAA CAACAACCCA TACTTCTCCG
2281 GACCATACGG TAAGAGTTGC AGTCTTCGTA TATATATCTG TTGAGCTCGA GAATCTTCAC
2341 AGGAAGCGGC CCATCAGACG GACTGTCATT TTACACTGAC TACTGCTGCT GCTCTTCGTC
2401 CATCCATACA AGGGGAGGAC GTCGTGTTCG TCTGCAACGA CTGGCACACC GGCCCTCTCT
2461 CGTGCTACCT CAAGAGCAAC TACCAGTCCC ACGGCATCTA CAGGGACGCA AAGGTTGCCT
```

TABLE 1a-continued

DNA Sequence and Deduced Amino Acid Sequence
of the waxy Gene in Maize
[SEQ ID NO:4 and SEQ ID NO:5]

```
2521 TCTCTGAACT GAACAACGCC GTTTTCGTTC TCCATGCTCG TATATACCTC GTCTGGTAGT

2581 GGTGGTGCTT CTCTGAGAAA CTAACTGAAA CTGACTGCAT GTCTGTCTGA CCATCTTCAC

2641 GTACTACCAG ACCGCTTTCT GCATCCACAA CATCTCCTAC CAGGGCCGGT TCGCCTTCTC

2701 CGACTACCCG GAGCTGAACC TCCCGGAGAG ATTCAAGTCG TCCTTCGATT TCATCGACGG

2761 GTCTGTTTTC CTGCGTGCAT GTGAACATTC ATGAATGGTA ACCCACAACT GTTCGCGTCC

2821 TGCTGGTTCA TTATCTGACC TGATTGCATT ATTGCAGCTA CGAGAAGCCC GTGGAAGGCC

2881 GGAAGATCAA CTGGATGAAG GCCGGGATCC TCGAGGCCGA CAGGGTCCTC ACCGTCAGCC

2941 CCTACTACGC CGAGGAGCTC ATCTCCGGCA TCGCCAGGGG CTGCGAGCTC GACAACATCA

3001 TGCGCCTCAC CGGCATCACC GGCATCGTCA ACGGCATGGA CGTCAGCGAG TGGGACCCCA

3061 GCAGGGACAA GTACATCGCC GTGAAGTACG ACGTGTCGAC GGTGAGCTGG CTAGCTCTGA

3121 TTCTGCTGCC TGGTCCTCCT GCTCATCATG CTGGTTCGGT ACTGACGCGG CAAGTGTACG

3181 TACGTGCGTG CGACGGTGGT GTCCGGTTCA GGCCGTGGAG GCCAAGGCGC TGAACAAGGA

3241 GGCGCTGCAG GCGGAGGTCG GGCTCCCGGT GGACCGGAAC ATCCCGCTGG TGGCGTTCAT

3301 CGGCAGGCTG GAAGAGCAGA AGGGCCCCGA CGTCATGGCG GCCGCCATCC CGCAGCTCAT

3361 GGAGATGGTG GAGGACGTGC AGATCGTTCT GCTGGTACGT GTGCGCCGGC CGCCACCCGG

3421 CTACTACATG CGTGTATCGT TCGTTCTACT GGAACATGCC TGTGAGCAAC GCGATGGATA

3481 ATGCTGCAGG GCACGGGCAA GAAGAAGTTC GAGCGCATGC TCATGAGCGC CGAGGAGAAG

3541 TTCCCAGGCA AGGTGCGCGC CGTGGTCAAG TTCAACGCGG CGCTGGCGCA CCACATCATG

3601 GCCGGCGCCG ACGTGCTCGC CGTCACCAGC CGCTTCGAGC CCTGCGGCCT CATCCAGCTG

3661 CAGGGGATGC GATACGGAAC GGTACGAGAG AAAAAAAAAA TCCTGAATCC TGACGAGAGG

3721 GACAGAGACA GATTATGAAT GCTTCATCGA TTTGAATTGA TTGATCGATG TCTCCCGCTG

3781 CGACTCTTGC AGCCCTGCGC CTGCGCGTCC ACCGGTGGAC TCGTCGACAC CATCATCGAA

3841 GGCAAGACCG GGTTCCACAT GGGCCGCCTC AGCGTCGACG TAAGCCTAGC TCTGCCATGT

3901 TCTTTCTTCT TTCTTTCTGT ATGTATGTAT GAATCAGCAC CGCCGTTCTT GTTTCGTCGT

3961 CGTCCTCTCT TCCCAGTGTA ACGTCGTGGA GCCGGCGGAC GTCAAGAAGG TGGCCACCAC

4021 ATTGCAGCGC GCCATCAAGG TGGTCGGCAC GCCGGCGTAC GAGGAGATGG TGAGGAACTG

4081 CATGATCCAG GATCTCTCCT GGAAGGTACG TACGCCCGCC CCGCCCCGCC CCGCCAGAGC

4141 AGAGCGCCAA GATCGACCGA TCGACCGACC ACACGTACGC GCCTCGCTCC TGTCGCTGAC

4201 CGTGGTTTAA TTTGCGAAAT GCGCAGGGCC CTGCCAAGAA CTGGGAGAAC GTGCTGCTCA

4261 GCCTCGGGGT CGCCGGCGGC GAGCCAGCGG TCGAAGGCGA GGAGATCGCG CCGCTCGCCA

4321 AGGAGAACGT GGCCGCGCCC TGAAGAGTTC GGCCTGCAGG GCCCCTGATC TCGCGCGTGG

4381 TGCAAAGATG TTGGGACATC TTCTTATATA TGCTGTTTCG TTTATGTGAT ATGGACAAGT

4441 ATGTGTAGCT GCTTGCTTGT GCTAGTGTAA TGTAGTGTAG TGGTGGCCAG TGGCACAACC

4501 TAATAAGCGC ATGAACTAAT TGCTTGCGTG TGTAGTTAAG TACCGATCGG TAATTTTATA

4561 TTGCGAGTAA ATAAATGGAC CTGTAGTGGT GGAGTAAATA ATCCCTGCTG TTCGGTGTTC

4621 TTATCGCTCC TCGTATAGAT ATTATATAGA GTACATTTTT CTCTCTCTGA ATCCTACGTT
```

TABLE 1a-continued

DNA Sequence and Deduced Amino Acid Sequence
of the waxy Gene in Maize
[SEQ ID NO:4 and SEQ ID NO:5]

```
4681 TGTGAAATTT CTATATCATT ACTGTAAAAT TTCTGCGTTC CAAAAGAGAC CATAGCCTAT

4741 CTTTGGCCCT GTTTGTTTCG GCTTCTGGCA GCTTCTGGCC ACCAAAAGCT GCTGCGGACT
//
```

TABLE 1b

DNA Seciuence and Deduced Amino Acid Sequence in waxy Gene in Rice
[SEO ID NO:6 and SEO ID NO:7]

```
LOCUS         OSWX            2542 bp    RNA             PLN
DEFINITION    O. sativa Waxy mRNA.
ACCESSION     X62134 S39554
KEYWORDS      glucosyltransferase; starch biosynthesis; waxy gene.
SOURCE        rice.
  ORGANISM    Oryza sativa
              Eukaryota; Plantae; Embryobionta; Magnoliophyta; Liliopsida;
              Commelinidae; Cyperales; Poaceae.
REFERENCE     1  (bases 1 to 2542)
  AUTHORS     Okayaki, R. J.
  TITLE       Direct Submission
  JOURNAL     Submitted (12-SEP-1991) to the EMBL/GenBank/DDBJ databases.
R.J.
              Okayaki, University of Florida, Dep of Vegetable Crops, 1255
              Fifield Hall, 514 IFAS, Gainesville, Florida 32611-0514, USA
  STANDARD    full automatic
REFERENCE     2  (bases 1 to 2542)
  AUTHORS     Okagaki, R. J.
  TITLE       Nucleotide sequence of a long cONA from the rice waxy gene
  JOURNAL     Plant Mol. Biol. 19, 513-516 (1992)
  STANDARD    full automatic
COMMENT       NCBI gi: 20402
FEATURES             Location/Qualifiers
     source          1 . . . 2542
                     /organism="Oryza sativa"
                     /dev stage="immature seed"
                     /tissue type="seed"
     CDS             453 . . . 2282
                     /gene="Wx"
                     /standard_name="Waxy gene"
                     /EC_number="2.4.1.21"
                     /note="NCBI gi: 20403"
                     /codon_start=1
                     /function="starch biosynthesis"
                     /product="starch (bacterial glycogen) synthase"

/translation="MSALTTSQLATSATGFGIADRSAPSSLLRNGFQGLKPRSPAGGD

ATSLSVTTSARATPKQQRSVQRGSRRFPSVVVATGAGMNVVFVGAEMAPWSKTGGLG

DVLGGLPPAMAANGHRVMVISPRYDQYKDAWDTSVVAEIKVADRYERVRFFHCYKRGV

DRVFIDHPSFLEKVWGKTGEKIYGPDTGVDYKDNQMRFSLLCQAALEAPRILNLNNNP

YFKGTYGEDVVFVCNDWHTGPLASYLKNNYQPNGIYRNAKVAFCIHNISYQGRFAFED

YPELNLSERFRSSFDFIDGYDTPVEGRKINWMKAGILEADRVLTVSPYYAELISGIA

RGCELDNIMRLTGITGIVNGMDVSEWDPSKDKYITAXYDATTAIEAKALNKEALQAEA

GLPVDRKIPLIAFIGRLEEQKGPDVMAAAIPELMQEDVQIVLLGTGKKXFEKLLKSME

EKYPGKVRAVVKFNAPLAHLIMAGADVLAVPSRFEPCGLIQLQGMRYGTPCACASTGG

LVDTVIEGKTGFHMGRLSVDCKVVEPSDVKKVAATLKRAIKVVGTPAYEEMVRNCMNQ

DLSWKGPAKNWENVLLGLGVAGSAPGIEGDEIAPLAKENVAAP"
     3'UTR           2283 . . . 2535
     polyA_site      2535
```

TABLE 1b-continued

DNA Sequence and Deduced Amino Acid Sequence in waxy Gene in Rice
[SEQ ID NO:6 and SEQ ID NO:7]

BASE COUNT    610 A    665 C    693 G    574 T
ORIGIN

```
   1 GAATTCAGTG TGAAGGAATA GATTCTCTTC AAAACARTTT AATCATTCAT CTGATCTGCT
  61 CAAAGCTCTG TGCATCTCCG GGTGCAACGG CCAGGATATT TATTGTGCAG TAAAAAAATG
 121 TCATATCCCC TAGCCACCCA AGAAACTGCT CCTTAAGTCC TTATAAGCAC ATATGGCATT
 181 GTAATATATA TGTTTGAGTT TTAGCGACAA TTTTTTTAAA AACTTTTGGT CCTTTTTATG
 241 AACGTTTTAA GTTTCACTGT CTTTTTTTTT CGAATTTTAA ATGTAGCTTC AAATTCTAAT
 301 CCCCAATCCA AATTGTAATA AACTTCAATT CTCCTAATTA ACATCTTAAT TCATTTATTT
 361 GAAAACCAGT TCAAATTCTT TTTAGGCTCA CCAAACCTTA AACAATTCAA TTCAGTGCAG
 421 AOATCTTCCA CAGCAACAGC TAGACAACCA CCATGTCGGC TCTCACCACG TCCCAGCTCG
 481 CCACCTCGGC CACCGGCTTC GGCATCGCCG ACAGGTCGGC GCCGTCGTCG CTGCTCCGCC
 541 ACGGGTTCCA GGGCCTCAAG CCCCGCAGCC CCGCCGGCGG CGACGCGACG TCGCTCAGCG
 601 TGACGACCAG CGCGCGCGCG ACGCCCAAGC AGCAGCGGTC GGTGCAGCGT GGCAGCCGGA
 661 GGTTCCCCTC CGTCGTCGTG TACGCCACCG GCGCCGGCAT GAACGTCGTG TTCGTCGGCG
 721 CCGAGATGGC CCCCTGOAGC AAGACCGGCG GCCTCGGTGA CGTCCTCGGT GGCCTCCCCC
 781 CTGCCATGGC TGCGAATGGC CACAGGGTCA TGGTGATCTC TCCTCGGTAC GACCAGTACA
 841 AGGACGCTTG GGATACCAGC GTTGTGGCTG AGATCAAGGT TGCAGACAGG TACGAGAGGG
 901 TGAGGTTTTT CCATTGCTAC AAGCGTGGAG TCGACCGTGT GTTCATCGAC CATCCGTCAT
 961 TCCTGGAGAA GGTTTGGGGA AGACCGGTG AGAAGATCTA CGGACCTGAC ACTGGAGTTG
1021 ATTACAAAGA CAACCAGATG CGTTTCAGCC TTCTTTGCCA GGCAGCACTC GAGGCTCCTA
1081 GGATCCTAAA CCTCAACAAC AACCCATACT TCAAAGGAAC TTATGGTGAG GATGTTGTGT
1141 TCGTCTGCAA CGACTGGCAC ACTGGCCCAC TGGCGAGCTA CCTGAAGAAC AACTACCAGC
1201 CCAATGGCAT CTACAGGAAT GCAXAGGTTG CTTTCTGCAT CCACAACATC TCCTACCAGG
1261 GCCGTTTCGC TTTCGAGGAT TACCCTGAGC TGAACCTCTC CGAGAGGTTC AGGTCATCCT
1321 TCGATTTCAT CGACGGGTAT GACACGCCGG TGGAGGGCAG GAAGATCAAC TGGATGAAGG
1381 CCGGAATCCT GGAAGCCGAC AGOGTGCTCA CCGTGAGCCC GTACTACGCC GAGGAGCTCA
1441 TCTCCGGCAT CGCCAGGGGA TGCGAGCTCG ACAACATCAT GCGGCTCACC GGCATCACCG
1501 GCATCGTCAA CGGCATGGAC GTCAGCGAGT GGGATCCTAG CAAGGACAAG TACATCACCG
1561 CCAAGTACGA CGCAACCACG GCAATCGAGG CGAAGGCGCT GAACAAGGAG GCGTTGCAGG
1621 CGGAGGCGGG TCTTCCGGTC GACAGGAAAA TCCCACTGAT CGCGTTCATC GGCAGGCTGG
1681 AGGAACAGAA GGGCCCTGAC GTCATGGCCG CCGCCATCCC GGAGCTCATG CAGGAGGACG
1741 TCCAGATCGT TCTTCTGGGT ACTGGAAAGA AGAAGTTCGA AAGCTGCTC AAGAGCATGG
1801 AOGAGAAGTA TCCGGGCAAG GTGAGGGCGG TGGTGAAGTT CAACGCGCCG CTTGCTCATC
1861 TCATCATGGC CGGAGCCGAC GTGCTCGCCG TCCCCAGCCG CTTCGAGCCC TGTGGACTCA
1921 TCCAGCTGCA GGOGATGAGA TACGGAACGC CCTGTGCTTG CGCGTCCACC GGTGGGCTCG
1981 TGGACACGGT CATCGAAGGC AAGACTGGTT TCCACATGGG CCGTCTCAGC GTCGACTGCA
2041 AGGTGGTGGA GCCAAGCGAC GTGAAOAAGG TGGCGGCCAC CCTGAAGCGC GCCATCAAGG
2101 TCGTCGGCAC GCCGGCGTAC GAGGAGATGG TCAGGAACTG CATGAACCAG GACCTCTCCT
2161 GGAAGGGGCC TGCGAAGAAC TGGGAGAATG TOCTCCTGGG CCTGGGCGTC GCCGGCAGCG
```

TABLE 1b-continued

DNA Sequence and Deduced Amino Acid Sequence in waxy Gene in Rice
[SEQ ID NO:6 and SEQ ID NO:7]

```
2221 CGCCGGGGAT CGAAGGCGAC GAGATCGCGC CGCTCGCCAA GGAGAACGTG GCTGCTCCTT

2281 GAAGAGCCTG AGATCTACAT ATGGAGTGAT TAATTAATAT AGCAGTATAT GGATGAGAGA

2341 CGAATGAACC AGTGGTTTGT TTGTTGTAGT GAATTTGTAG CTATAGCCAA TTATATAGGC

2401 TAATAAGTTT GATGTTGTAC TCTTCTGGGT GTGCTTAAGT ATCTTATCGG ACCCTGAATT

2461 TATGTGTGTG GCTTATTGCC AATAATATTA AGTAATAAAG GGTTTATTAT ATTATTATAT

2521 ATGTTATATT ATACTAAAAA AA
//
```

TABLE 2

DNA Sequence and Deduced Amino Acid Sequence of
the Soluble Starch Synthase IIa Gene in Maize
[SEQ ID NO:8 and SEQ ID NO:9]

```
      FILE NAME:     MSS2C.SEQ     SEQUENCE: NORMAL   2007 BP
      CODON TABLE:   UNIV.TCN
      SEQUENCE REGION:  1-2007
      TRANSLATION REGION 1-2007
*** DNA TRANSLATION ***

1 GCT GAG GCT GAG GCC GGG GGC AAG GAC GCG CCG CCG GAG AGG AGC GGC    48
  1  A   E   A   E   A   G   G   K   D   A   P   P   E   R   S   G    16

49 GAC GCC GCC AGG TTG CCC CGC GCT CGG CGC AAT GCG GTC TCC AAA CGG    96
 17  D   A   A   R   L   P   R   A   R   R   N   A   V   S   K   R    32

97 AGG GAT CCT CTT CAG CCG GTC GGC CGG TAC GGC TCC GCG ACG GGA AAC   144
 33  R   D   P   L   Q   P   V   G   R   Y   G   S   A   T   G   N    48

145 ACG GCC AGG ACC GGC GCC GCG TCC TGC CAG AAC GCC GCA TTG GCG GAC   192
 49  T   A   R   T   G   A   A   S   C   Q   N   A   A   L   A   D    64

193 GTT GAG ATC GTT GAG ATC AAG TCC ATC GTC GCC GCG CCG CCG ACG AGC   240
 65  V   E   I   V   E   I   K   S   I   V   A   A   P   P   T   S    80

241 ATA GTG AAG TTC CCA GGG CGC GGG CTA CAG GAT GAT CCT TCC CTC TGG   288
 81  I   V   K   F   P   G   R   G   L   Q   D   D   P   S   L   W    96

289 GAC ATA GCA CCG GAG ACT GTC CTC CCA GCC CCG AAG CCA CTG CAT GAA   336
 97  D   I   A   P   E   T   V   L   P   A   P   K   P   L   H   E   112

337 TCG CCT GCG GTT GAC GGA GAT TCA AAT GGA ATT GCA CCT CCT ACA GTT   384
113  S   P   A   V   D   G   D   S   N   G   I   A   P   P   T   V   128

385 GAG CCA TTA GTA CAG GAG GCC ACT TGG GAT TTC AAG AAA TAC ATC GGT   432
129  E   P   L   V   Q   E   A   T   W   D   F   K   K   Y   I   G   144

433 TTT GAC GAG CCT GAC GAA GCG AAG GAT GAT TCC AGG GTT GGT GCA GAT   480
145  F   D   E   P   D   E   A   K   D   D   S   R   V   G   A   D   160

481 GAT GCT GGT TCT TTT GAA CAT TAT GGG ACA ATG ATT CTG GGC CTT TGT   528
161  D   A   G   S   F   E   H   Y   G   T   M   I   L   G   L   C   176

529 GGG GAG AAT GTT ATG AAC GTG ATC GTG GTG GCT GCT GAA TCT TCT CCA   576
177  G   E   N   V   M   N   V   I   V   V   A   A   E   S   S   P   192

577 TGG TGC AAA ACA GGT GGT CTT GGA GAT GTT GTG GGA GCT TTA CCC AAG   624
193  W   C   K   T   G   G   L   G   D   V   V   G   A   L   P   K   208

625 GCT TTA GCG AGA AGA GGA CAT CGT GTT ATG GTT GTG TA CCA AGC TAT   672
209  A   L   A   R   R   G   H   R   V   M   V   V   P   R   Y   224

673 GGG GAC TAT GTG GAA GCC TTT GAT ATG GGA ATC CGG AAA TAC TAC AAA   720
225  G   D   Y   V   E   A   F   D   M   G   I   R   K   Y   Y   K   240

721 GCT GCA GGA CAG GAC CTA GAA GTG AAC TAT TTC CAT GCA TTT ATT GAT   768
241  A   A   G   Q   D   L   E   V   N   Y   F   H   A   F   I   D   256
```

TABLE 2-continued

DNA Sequence and Deduced Amino Acid Sequence of
the Soluble Starch Synthase IIa Gene in Maize
[SEQ ID NO:8 and SEQ ID NO:9]

```
 769 GGA GTC GAC TTT GTG TTC ATT GAT GCC TCT TTC CGG CAC CGT CAA GAT  816
 257  G   V   D   F   V   F   I   D   A   S   F   R   H   R   Q   D   272

817 GAC ATA TAT GGG GGA AGT AGG CAG GAA ATC ATG AAG CGC ATG ATT TTG  864
 273  D   I   Y   G   G   S   R   Q   E   I   M   K   R   M   I   L   288

865 TTT TGC AAG GTT GCT GTT GAG GTT CCT TGG CAC CTT CCA TGC GGT GGT  912
 289  F   C   K   V   A   V   E   V   P   W   H   V   P   C   G   G   304

913 GTG TGC TAC GGA GAT GGA AAT TTG GTG TTC ATT GCC ATG AAT TGG CAC  960
 305  V   C   Y   G   D   G   N   L   V   F   I   A   M   N   W   H   320

961 ACT GCA CTC CTG CCT GTT TAT CTG AAG GCA TAT TAC AGA GAC CAT GGG 1008
 321  T   A   L   L   P   V   Y   L   K   A   Y   Y   R   D   H   G   336

1009 TTA ATG CAG TAC ACT CGC TCC GTC CTC GTC ATA CAT AAC ATC GGC CAC 1056
 337  L   M   Q   Y   T   R   S   V   L   V   I   H   N   I   G   H   352

1057 CAG GGC CGT GGT CCT GTA CAT GAA TTC CCG TAC ATG GAC TTG CTG AAC 1104
 353  Q   G   R   G   P   V   H   E   F   P   Y   M   D   L   L   N   368

1105 ACT AAC CTT CAA CAT TTC GAG CTG TAC GAT CCC GTC GGT GGC GAG CAC 1152
 369  T   N   L   Q   H   F   E   L   Y   D   P   V   G   G   E   H   384

1153 GCC AAC ATC TTT GCC GCG TGT GTT CTG AAG ATG GCA GAC CGG GTG GTG 1200
 385  A   N   I   F   A   A   C   V   L   K   M   A   D   R   V   V   400

1201 ACT GTC AGC CGC GGC TAC CTG TGG GAG CTG AAG ACA GTG GAA GGC GGC 1248
 401  T   V   S   R   G   Y   L   W   E   L   K   T   V   E   G   G   416

1249 TGG GGC CTC CAC GAC ATC ATC CGT TCT AAC GAC TGG AAG ATC AAT GGC 1296
 417  W   G   L   H   D   I   I   R   S   N   D   W   K   I   N   G   432

1297 ATT CGT GAA CGC ATC GAC CAC CAG GAG TGG AAC CCC AAC GTG GAC GTG 1344
 433  I   R   E   R   I   D   H   Q   E   W   N   P   N   V   D   V   448

1345 CAC CTG CGG TCG GAC GGC TAC ACC AAC TAC TCC CTC GAG ACA CTC GAC 1392
 449  H   L   R   S   D   G   Y   T   N   Y   S   L   E   T   L   D   464

1393 CCT GGA PAG CGG GAG TGC AAG GCG GCC CTG CAG CGG CAC GTC CGC CTG 1440
 465  A   G   K   R   Q   C   K   A   A   L   Q   R   D   V   G   L   480

1441 GAA GTG CGC GAC GAC GTG CCG CTG CTC GGC TTC ATC GGG CGT CTG GAT 1488
 481  E   V   R   D   D   V   P   L   L   G   F   I   G   R   L   D   496

1489 GGA CAG AAG GGC GTC GAC ATC ATC GGG GAC GCG ATG CCG TGG ATC GCG 1536
 497  G   Q   K   C   V   D   I   I   G   D   A   M   P   W   I   A   512

1537 GGG CAG GAC GTG CAG CTG GTG ATG CTG GGC ACC GGC CCA CCT GAC CTG 1584
 513  G   Q   D   V   Q   L   V   M   L   G   T   G   P   P   D   L   528

1585 GAA CGA ATG CTG CAG CAC TTG GAG CGG GAG CAT CCC AAG AAG GTG CGC 1632
 529  E   R   M   L   Q   H   L   E   R   E   H   P   N   K   V   R   544

1633 GGG TGG GTC GGG TTC TCG GTC CTA ATG GTG CAT CGC ATC ACG CCG GGC 1680
 545  G   W   V   G   F   S   V   L   M   V   H   R   I   T   P   G   560

1681 GCC AGC GTG CTG GTG ATG CCC TCC CGC TTC GCC GGC GGG CTG AAC CAG 1728
 561  A   S   V   L   V   M   P   S   R   F   A   G   G   L   N   Q   576

1729 CTC TAC GCG ATG GCA TAC GGC ACC GTC CCT GTG GTG CAC GCC GTG GGC 1776
 577  L   Y   A   M   A   Y   G   T   V   P   V   V   H   A   V   G   592

1777 GGG CTC AGG GAC ACC GTG GCG CCG TTC GAC CCG TTC GGC GAC GCC GGG 1824
 593  G   L   R   D   T   V   A   P   F   D   P   F   G   D   A   G   608

1825 CTC GGG TGG ACT TTT GAC CGC GCC GAG GCC AAC AAG CTG ATC GAG GTG 1872
 609  L   G   W   T   F   D   R   A   E   A   N   K   L   I   E   V   624

1873 CTC AGC CAC TGC CTC GAC ACG TAC CGA AAC TAC GAG GAG AGC TCC AAG 1920
 625  L   S   H   C   L   D   T   Y   R   N   Y   E   E   S   W   K   640

1921 AGT CTC CAG GCG CGC GGC ATG TCG CAG AAC CTC AGC TGC GAC CAC GCC 1968
 641  S   L   Q   A   R   G   M   S   Q   N   L   S   W   D   H   A   656
```

TABLE 2-continued

DNA Sequence and Deduced Amino Acid Sequence of
the Soluble Starch Synthase IIa Gene in Maize
[SEQ ID NO:8 and SEQ ID NO:9]

```
1969 GCT GAG CTC TAC GAG GAC GTC CTT GTC AAC TAC CAG TGG         2007
 657  A   E   L   Y   E   D   V   L   V   K   Y   Q   W           669
```

TABLE 3

DNA Sequence and Deduced Amino Acid Sequence of
The Soluble Starch Synthase IIb Gene in Maize
[SEQ ID NO:10 and SEQ ID NO: 11]

```
    FILE NAME:         MSS3FULL.DNA    SEQUENCE: NORMAL    2097 BP
    CODON TABLE:       UNIV.TCN
    SEQUENCE REGION:   1-2097
    TRANSLATION        1-2097
    REGION:
*** DNA TRANSLATION ***
  1 ATG CCG GGG GCA ATC TCT TCC TCG TCG TCG GCT TTT CTC CTC CCC GTC    48
  1  M   P   G   A   I   S   S   S   S   S   A   F   L   L   P   V    16

49 GCG TCC TCC TCG CCG CGG CGC AGG CGG GGC AGT GTG GGT GCT GCT CTG    96
 17  A   S   S   S   P   R   R   R   R   G   S   V   G   A   A   L    32

97 CGC TCG TAC GGC TAC AGC GGC GCG GAG CTG CGG TTG CAT TGG GCG CGG   144
 33  R   S   Y   G   Y   S   G   A   E   L   R   L   H   W   A   R    48

145 CGG GGC CCG CCT CAG GAT GGA GCG GCG TCG GTA CGC GCC GCA GCG GCA   192
 49  R   G   P   P   Q   D   G   A   A   S   V   R   A   A   A   A    64

193 CCG GCC GGG GGC GAA AGC GAG GAG GCA GCG AAG AGC TCC TCC TCG TCC   240
 65  P   A   G   G   E   S   E   E   A   A   K   S   S   S   S   S    80

241 CAG GCG GGC GCT GTT CAG GGC AGC ACG GCC AAG GCT GTG GAT TCT GCT   288
 81  Q   A   G   A   V   Q   G   S   T   A   K   A   V   D   S   A    96

289 TCA CCT CCC AAT CCT TTG ACA TCT GCT CCG AAG CAA AGT CAG AGC GCT   336
 97  S   P   P   N   P   L   T   S   A   P   K   Q   S   Q   S   A   112

337 GCA ATG CAA AAC GGA ACG AGT GGG GGC AGC AGC GCG AGC ACC GCC GCG   384
113  A   M   Q   N   G   T   S   G   G   S   S   A   S   T   A   A   128

385 CCG GTG TCC GGA CCC AAA GCT GAT CAT CCA TCA GCT CCT GTC ACC AAG   432
129  P   V   S   G   P   K   A   D   H   P   S   A   P   V   TK      144

433 AGA GAA ATC GAT GCC AGT GCG GTG AAG CCA GAG CCC GCA GGT GAT GAT   480
145  R   E   I   D   A   S   A   V   K   P   E   P   A   G   D   D   160

481 GCT AGA CCG GTG GAA AGC ATA GGC ATC GCT GAA CCG GTG GAT GCT AAG   528
161  A   R   P   V   E   S   I   G   I   A   E   P   V   D   A   K   176

529 GCT GAT GCA GCT CCG GCT ACA GAT GCG GCG GCG AGT GCT CCT TAT GAC   576
177  A   D   A   A   P   A   T   D   A   A   A   S   A   P   Y   D   192

577 AGG GAG GAT AAT GAA CCT GGC CCT TTG GCT GGG CCT AAT GTG ATG AAC   624
193  R   E   D   N   E   P   G   P   L   A   G   P   N   V   M   N   208

625 GTC GTC GTG GTG GCT TCT GAA TGT GCT CCT TTC TGC AAG ACA GGT GGC   672
209  V   V   V   V   A   S   E   C   A   P   F   C   K   T   G   G   224

673 CTT GGA GAT GTC GTG GGT GCT TTG CCT AAG GCT CTG GCG AGG AGA GGA   720
225  L   G   D   V   V   G   A   L   P   K   A   L   A   R   R   G   240

721 CAC CGT GTT ATG GTC GTG ATA CCA AGA TAT GGA GAG TAT GCC GAA GCC   768
241  H   R   V   M   V   V   I   P   R   Y   G   E   Y   A   E   A   256

769 CGG GAT TTA GGT GTA AGG AGA CGT TAC AAG GTA GCT GGA CAG GAT TCA   816
257  R   D   L   G   V   R   R   R   Y   K   V   A   G   Q   D   S   272

817 GAA GTT ACT TAT TTT CAC TCT TAC ATT GAT GGA GTT GAT TTT GTA TTC   864
273  E   V   T   Y   F   H   S   Y   I   D   G   V   B   F   V   F   288

865 GTA GAA GCC CCT CCC TTC CGG CAC CGG CAC AAT AAT ATT TAT GGG GGA   912
289  V   E   A   P   P   F   R   H   R   H   N   N   I   Y   G   G   304
```

TABLE 3-continued

DNA Sequence and Deduced Amino Acid Sequence of
The Soluble Starch Synthase IIb Gene in Maize
[SEQ ID NO:10 and SEQ ID NO: 11]

```
 913 GAA AGA TTG GAT ATT TTG AAG CGC ATG ATT TTG TTC TGC AAG GCC GCT  960
 305  E   R   L   D   I   L   K   R   M   I   L   F   C   K   A   A   320

961 GTT GAG GTT CCA TGG TAT GCT CCA TGT GGC GGT ACT GTC TAT GGT GAT 1008
 321  V   E   V   P   W   Y   A   P   C   G   G   T   V   Y   G   D   336

1009 GGC AAC TTA GTT TTC ATT GCT AAT GAT TGG CAT ACC GCA CTT CTG CCT 1056
 337  G   N   L   V   F   I   A   N   D   W   H   T   A   L   L   P   352

1057 GTC TAT CTA AAG GCC TAT TAC CGG GAC AAT GGT TTG ATG CAG TAT GCT 1104
 353  V   Y   L   K   A   Y   Y   R   D   N   G   L   M   Q   Y   A   368

1105 CGC TCT GTG CTT GTG ATA CAC AAC ATT GCT CAT CAG GGT CGT GGC CCT 1152
 369  R   S   V   L   V   I   H   N   I   A   H   Q   C   R   G   P   384

1153 GTA GAC GAC TTC GTC AAT TTT GAC TTG CCT GAA CAC TAC ATC GAC CAC 1200
 385  V   D   D   F   V   N   F   D   L   P   E   H   Y   I   D   H   400

1201 TTC AAA CTG TAT GAC AAC ATT GGT GGG GAT CAC AGC AAC GTT TTT GCT 1248
 401  F   K   L   Y   D   N   I   G   G   D   H   S   N   V   F   A   416

1249 GCG GGG CTG AAG ACG GCA GAC CGG GTG GTG ACC GTT AGC AAT GGC TAC 1296
 417  A   G   L   K   T   A   D   R   V   V   T   V   S   N   G   Y   432

1297 ATG TGG GAG CTG AAG ACT TCG GAA GGC GGG TGG GGC CTC CAC GAC ATC 1344
 433  M   W   E   L   K   T   S   E   G   G   W   G   L   H   D   I   448

1345 ATA AAC CAG AAC GAC TGG AAG CTG CAG GGC ATC GTG AAC GGC ATC GAC 1392
 449  I   N   Q   N   D   W   K   L   Q   G   I   V   N   G   I   D   464

1393 ATG AGC GAG TGG AAC CCC GCT GTG GAC GTG CAC CTC CAC TCC GAC GAC 1440
 465  M   S   E   W   N   P   A   V   D   V   H   L   H   S   D   D   480

1441 TAC ACC AAC TAC ACG TTC GAG ACG CTG GAC ACC GGC AAG CGG CAG TGC 1488
 481  Y   T   N   Y   T   F   E   T   L   D   T   G   K   R   Q   C   496

1489 AAG GCC GCC CTG CAG CGG CAG CTG GGC CTG CAG GTC CGC GAC GAC GTG 1536
 497  K   A   A   L   Q   R   Q   L   G   L   Q   V   R   D   D   V   512

1537 CCA CTG ATC GGG TTC ATC GGG CGG CTG GAC CAC CAG AAG GGC GTG GAC 1584
 513  P   L   I   G   F   I   G   R   L   D   H   Q   K   G   V   D   528

1585 ATC ATC GCC GAC GCG ATC CAC TGG ATC GCG GGG CAG GAC GTG CAG CTC  632
 529  I   I   A   D   A   I   H   W   I   A   G   Q   D   V   Q   L   544

1633 GTG ATG CTG GGC ACC GGG CGG GCC GAC CTG GAG GAC ATG CTG CGG CGG 1680
 545  V   M   L   G   T   G   R   A   D   L   E   D   M   L   R   R   560

1681 TTC GAG TCG GAG CAC AGC GAC AAG GTG CGC GCG TGG GTG GGG TTC TCG 1728
 561  F   E   S   E   H   S   D   K   V   R   A   W   V   G   F   S   576

1729 GTG CCC CTG GCG CAC CGC ATC ACG GCG GGC GCG GAC ATC CTG CTG ATG 1776
 577  V   P   L   A   H   R   I   T   A   G   A   D   I   L   L   M   592

1777 CCG TCG CGG TTC GAG CCG TGC GGG CTG AAC CAG CTC TAC GCC ATG GCG 1824
 593  P   S   R   F   E   P   C   G   L   N   Q   L   Y   A   M   A   608

1825 TAC GGG ACC GTG CCC GTG GTG CAC GCC GTG GGG GGC CTC CCC GAC ACG 1872
 609  Y   G   T   V   P   V   V   H   A   V   G   G   L   P   D   T   624

1873 GTG GCG CCG TTC GAC CCG TTC AAC GAC ACC GGG CTC GGG TGG ACG TTC 1920
 625  V   A   P   F   D   P   F   N   D   T   G   L   G   W   T   F   640

1921 GAC CGC GCG GAG GCG AAC CCG ATG ATC GAC GCG CTC TCG CAC TGC CTC 1968
 641  D   R   A   E   A   N   P   M   I   D   A   L   S   H   C   L   656

1969 ACC ACG TAC CGG AAC TAC AAG GAG AGC TGG CGC GCC TGC AGG GCG CGC 2016
 657  T   T   Y   R   N   Y   K   E   S   W   R   A   C   R   A   R   672

2017 GGC ATG GCC GAG GAC CTC AGC TGG GAC CAC GCC GCC GTG CTG TAT GAG 2064
 673  G   M   A   E   D   L   S   W   D   H   A   A   V   L   Y   E   688
```

TABLE 3-continued

DNA Sequence and Deduced Amino Acid Sequence of
The Soluble Starch Synthase IIb Gene in Maize
[SEQ ID NO:10 and SEQ ID NO: 11]

```
2065 GAC GTG CTC GTC AAG GCG AAG TAC CAG TGG TGA              2097
 689  D   V   L   V   K   A   K   Y   Q   W*                  699
```

TABLE 4

DNA and Deduced Amino Acid Sequence of
The Soluble Starch Synthase I Gene in Maize
[SEQ ID NO: 12; SEQ ID NO: 13]

```
FILE NAME           MSS1FULL.DNA SEQUENCE: NORMAL   1752 BP
CODON TABLE:        UNIV.TCN
SEQUENCE REGION:    1-1752
TRANSLATION REGION: 1-1752

TGC GTC GCG GAG CTG AGC AGG GAG GGG CCC CCC CCG CGC CCG CTG CCA      48
Cys Val Ala Glu Leu Ser Arg Glu Gly Pro Ala Pro Arg Pro Leu Pro
700             705             710             715

CCC GCG CTG CTG GCG CCC CCG CTC CTG CCC GCC TTC CTC GCG CCG CCG      96
Pro Ala Leu Leu Ala Pro Pro Leu Val Pro Gly Phe Leu Ala Pro Pro
                720             725             730

GCC GAG CCC ACG GGT GAG CCG GCA TCG ACG CCG CCG CCC GTG CCC GAC      144
Ala Glu Pro Thr Gly Glu Pro Ala Ser Thr Pro Pro Pro Val Pro Asp
            735             740             745

GCC GGC CTG GGG GAC CTC GGT CTC GAA CCT GAA GGG ATT GCT GAA GGT      192
Ala Gly Leu Gly Asp Leu Gly Leu Glu Pro Glu Gly Ile Ala Glu Gly
            750             755             760

TCC ATC GAT AAC ACA GTA GTT GTG GCA AGT GAG CAA GAT TCT GAG ATT      240
Ser Ile Asp Asn Thr Val Val Val Ala Ser Glu Gln Asp Ser Glu Ile
            765             770             775

GTG GTT GGA AAG GAG CAA GCT CGA GCT AAA GTA AGA CAA AGC ATT GTC      288
Val Val Gly Lys Glu Gln Ala Arg Ala Lys Val Arg Gln Ser Ile Val
780             785             790             795

TTT GTA ACC GGC GAA GCT TCT CCT TAT GCA AAG TCT GGG GGT CTA GGA      336
Phe Val Thr Gly Glu Ala Ser Pro Tyr Ala Lys Ser Gly Gly Leu Gly
                800             805             810

GAT GTT TGT GGT TCA TTG CCA GTT GCT CTT GCT GCT CGT GGT CAC CGT      384
Asp Val Gys Gly Ser Leu Pro Val Ala Leu Ala Ala Arg Gly His Arg
            815             820             825

GTG ATG GTT GTA ATG CCC AGA TAT TTA AAT GGT ACC TCC GAT AAG AAT      432
Val Met Val Val Met Pro Arg Tyr Leu Asn Gly Thr Ser Asp Lys Asn
            830             835             840

TAT GCA AAT GCA TTT TAC ACA GAA AAA CAC ATT CGG ATT CCA TGC TTT      480
Tyr Ala Asn Ala Phe Tyr Thr Glu Lys His Ile Arg Ile Pro Cys Phe
            845             850             855

GGC GGT GAA CAT GAA GTT ACC TTC TTC CAT GAG TAT AGA GAT TCA GTT      528
Gly Gly Glu His Glu Val Thr Phe Phe His Glu Tyr Arg Asp Ser Val
860             865             870             875

GAC TGG GTG TTT GTT GAT CAT CCC TCA TAT CAC AGA CCT GGA AAT TTA      576
Asp Trp Val Phe Val Asp His Pro Ser Tyr His Arg Pro Gly Asn Leu
                880             885             890

TAT GGA GAT AAG TTT GGT GCT TTT GGT GAT AAT CAG TTC AGA TAC ACA      624
Tyr Gly Asp Lys Phe Gly Ala Phe Gly Asp Asn Gln Phe Arg Tyr Thr
            895             900             905

CTC CTT TGC TAT GCT GCA TGT GAG GCT CCT TTG ATC CTT GAA TTG GGA      672
Leu Leu Cys Tyr Ala Ala Cys Glu Ala Pro Leu Ile Leu Glu Leu Gly
            910             915             920

GGA TAT ATT TAT GGA CAG AAT TGC ATG TTT GTT GTC AAT GAT TGG CAT      720
```

TABLE 4-continued

DNA and Deduced Amino Acid Sequence of
The Soluble Starch Synthase I Gene in Maize
[SEQ ID NO: 12; SEQ ID NO: 13]

| | | |
|---|---|---|
| Gly Tyr Ile Tyr Gly Gln Asn Cys Met Phe Val Val Asn Asp Trp His<br>925                 930                 935 | |
| GCC AGT CTA GTG CCA GTC GTT CTT GCT GCA AAA TAT AGA CCA TAT GGT<br>Ala Ser Leu Val Pro Val Leu Leu Ala Ala Lys Tyr Arg Pro Tyr Gly<br>940                 945                 950                955 | 768 |
| GTT TAT AAA GAC TCC CGC AGC ATT CTT GTA ATA CAT AAT TTA GCA CAT<br>Val Tyr Lys Asp Ser Arg Ser Ile Leu Val Ile His Asn Leu Ala His<br>                 960                 965                970 | 816 |
| CAG GGT GTA GAG CCT GCA AGC ACA TAT CCT GAC CTT GGG TTG CCA CCT<br>Gln Gly Val Glu Pro Ala Ser Thr Tyr Pro Asp Leu Gly Leu Pro Pro<br>             975                 980                985 | 864 |
| GAA TGG TAT GGA GCT CTG GAG TGG GTA TTC CCT GAA TGG GCG AGG AGG<br>Glu Trp Tyr Gly Ala Leu Glu Trp Val Phe Pro Glu Trp Ala Arg Arg<br>             990                 995               1000 | 912 |
| CAT GCC CTT GAC AAG GGT GAG GCA GTT AAT TTT TTG AAA GGT GCA GTT<br>His Ala Leu Asp Lys Gly Glu Ala Val Asn Phe Leu Lys Gly Ala Val<br>      1005               1010              1015 | 960 |
| GTG ACA GCA GAT CGA ATC GTG ACT GTC AGT AAG GGT TAT TCG TGG GAG<br>Val Thr Ala Asp Arg Ile Val Thr Val Ser Lys Gly Tyr Ser Trp Glu<br>1020                1025              1030              1035 | 1008 |
| GTC ACA ACT GCT GAA GGT GGA CAG GGC CTC AAT GAG CTC TTA AGC TCC<br>Val Thr Thr Ala Glu Gly Gly Gln Gly Leu Asn Glu Leu Leu Ser Ser<br>             1040              1045              1050 | 1056 |
| AGA AAG AGT GTA TTA AAC GGA ATT GTA AAT GGA ATT GAC ATT AAT GAT<br>Arg Lys Ser Val Leu Asn Gly Ile Val Asn Gly Ile Asp Ile Asn Asp<br>                1055              1060              1065 | 1104 |
| TGG AAC CCT GCC ACA GAC AAA TGT ATC CCC TGT CAT TAT TCT GTT GAT<br>Trp Asn Pro Ala Thr Asp Lys Cys Ile Pro Cys His Tyr Ser Val Asp<br>          1070              1075              1080 | 1152 |
| GAC CTC TCT GGA AAG GCC AAA TGT AAA GGT GCA TTG CAG AAG GAG CTG<br>Asp Leu Ser Gly Lys Ala Lys Cys Lys Gly Ala Leu Gln Lys Glu Leu<br>      1085               1090              1095 | 1200 |
| GGT TTA CCT ATA AGG CCT GAT GTT CCT CTG ATT GGC TTT ATT GGA AGG<br>Gly Leu Pro Ile Arg Pro Asp Val Pro Leu Ile Gly Phe Ile Gly Arg<br>1100              1105              1110              1115 | 1248 |
| TTG GAT TAT CAG AAA GGC ATT GAT CTC ATT CAA CTT ATC ATA CCA GAT<br>Leu Asp Tyr Gln Lys Gly Ile Asp Leu Ile Gln Leu Ile Ile Pro Asp<br>             1120              1125              1130 | 1296 |
| CTC ATG CGG GAA GAT GTT CAA TTT GTC ATG CTT GGA TCT GGT GAC CCA<br>Leu Met Arg Glu Asp Val Gln Phe Val Met Leu Gly Ser Gly Asp Pro<br>          1135              1140              1145 | 1344 |
| GAG CTT GAA GAT TGG ATG AGA TCT ACA GAG TCG ATC TTC AAG GAT AAA<br>Glu Leu Glu Asp Trp Met Arg Ser Thr Glu Ser Ile Phe Lys Asp Lys<br>      1150               1155              1160 | 1392 |
| TTT CGT GGA TGG GTT GGA TTT AGT GTT CCA GTT TCC CAC GGA ATA ACT<br>Phe Arg Gly Trp Val Gly Phe Ser Val Pro Val Ser His Arg Ile Thr<br>1165              1170              1175 | 1440 |
| GCC GGC TGC GAT ATA TTG TTA ATG CCA TCC AGA TTC GAA CCT TGT GGT<br>Ala Gly Cys Asp Ile Leu Leu Met Pro Ser Arg Phe Glu Pro Cys Gly<br>1180              1185              1190              1195 | 1488 |
| CTC AAT CAG CTA TAT GCT ATG CAG TAT GGC ACA GTT CCT GTT GTG CAT<br>Leu Asn Gln Leu Tyr Ala Met Gln Tyr Gly Thr Val Pro Val Val His<br>             1200              1205              1210 | 1536 |
| GCA ACT GGG GGC CTT AGA GAT ACC GTG GAG AAC TTC AAC CCT TTC GGT<br>Ala Thr Gly Gly Leu Arg Asp Thr Val Glu Asn Phe Asn Pro Phe Gly<br>          1215              1220              1225 | 1584 |

TABLE 4-continued

DNA and Deduced Amino Acid Sequence of
The Soluble Starch Synthase I Gene in Maize
[SEQ ID NO: 12; SEQ ID NO: 13]

```
GAG AAT GGA GAG CAG GGT ACA GGG TGG GCA TTC GCA CCC CTA ACG ACA    1632
Glu Asn Gly Glu Gln Gly Thr Gly Trp Ala Phe Ala Pro Leu Thr Thr
        1230                1235                1240

GAA AAC ATG TTT GTG GAC ATT GCG AAC TGC AAT ATC TAC ATA CAG GGA    1680
Glu Asn Met Phe Val Asp Ile Ala Asn Cys Asn Ile Tyr Ile Gln Gly
1245                1250                1255

ACA CAA GTC CTC CTG GGA AGG GCT AAT GAA GCG AGG CAT GTC AAA AGA    1728
Thr Gln Val Leu Leu Gly Arg Ala Asn Glu Ala Arg His Val Lys Arg
1260                1265                1270                1275

CTT CAC GTG GGA CCA TGC CGC TGA                                    1752
Leu His Val Gly Pro Cys Arg *
                1280
```

(2) INFORMATION FOR SEQ ID NO:13:
    (i)    SEQUENCE CHARACTERISTICS:
        (A) LENGTH: 584 amino acids
        (B) TYPE: amino acid
        (D) TOPOLOGY: linear
    (ii)   MOLECULE TYPE: protein
    (xi)   SEQUENCE DESCRIPTION: SEQ ID NO:13:

```
Cys Val Ala Glu Leu Ser Arg Glu Gly Pro Ala Arg Pro Leu Pro
 1               5                  10                  15

Pro Ala Leu Leu Ala Pro Pro Leu Val Pro Gly Phe Leu Ala Pro Pro
                20                  25                  30

Ala Glu Pro Thr Gly Glu Pro Ala Ser Thr Pro Pro Val Pro Asp
            35                  40                  45

Ala Gly Leu Gly Asp Leu Gly Leu Glu Pro Glu Gly Ile Ala Glu Gly
     50                  55                  60

Ser Ile Asp Asn Thr Val Val Ala Ser Glu Gln Asp Ser Glu Ile
65                  70                  75                  80

Val Val Gly Lys Glu Gln Ala Arg Ala Lys Val Thr Gln Ser Ile Val
                85                  90                  95

Phe Val Thr Gly Glu Ala Ser Pro Tyr Ala Lys Ser Gly Gly Leu Gly
                100                 105                 110

Asp Val Cys Gly Ser Leu Pro Val Ala Leu Ala Ala Arg Gly His Arg
            115                 120                 125

Val Met Val Met Pro Arg Tyr Leu Asn Gly Thr Ser Asp Lys Asn
        130                 135                 140

Tyr Ala Asn Ala Phe Tyr Thr Glu Lys His Ile Arg Ile Pro Cys Phe
145                 150                 155                 160

Gly Gly Glu His Glu Val Thr Phe Phe His Glu Tyr Arg Asp Ser Val
                165                 170                 175

Asp Trp Val Phe Val Asp His Pro Ser Tyr His Arg Pro Gly Asn Leu
            180                 185                 190

Tyr Gly Asp Lys Phe Gly Ala Phe Gly Asp Asn Gln Phe Arg Tyr Thr
            195                 200                 205

Leu Leu Cys Tyr Ala Ala Cys Glu Ala Pro Leu Ile Leu Glu Leu Gly
        210                 215                 220

Gly Tyr Ile Tyr Gly Gln Asn Cys Met Phe Val Val Asn Asp Trp His
225                 230                 235                 240

Ala Ser Leu Val Pro Val Leu Leu Ala Ala Lys Tyr Arg Pro Tyr Gly
                245                 250                 255

Val Tyr Lys Asp Ser Arg Ser Ile Leu Val Ile His Asn Leu Ala His
            260                 265                 270
```

TABLE 4-continued

DNA and Deduced Amino Acid Sequence of
The Soluble Starch Synthase I Gene in Maize
[SEQ ID NO: 12; SEQ ID NO: 13]

Gln Gly Val Glu Pro Ala Ser Thr Tyr Pro Asp Leu Gly Leu Pro Pro
        275                 280                 285

Glu Trp Tyr Gly Ala Leu Glu Trp Val Phe Pro Glu Trp Ala Arg Arg
    290                 295                 300

His Ala Leu Asp Lys Gly Glu Ala Val Asn Phe Leu Lys Gly Ala Val
305                 310                 315                 320

Val Thr Ala Asp Arg Ile Val Thr Val Ser Lys Gly Tyr Ser Trp Glu
                325                 330                 335

Val Thr Thr Ala Glu Gly Gly Gln Gly Leu Asn Glu Leu Leu Ser Ser
                340                 345                 350

Arg Lys Ser Val Leu Asn Gly Ile Val Asn Gly Ile Asp Ile Asn Asp
            355                 360                 365

Trp Asn Pro Ala Thr Asp Lys Cys Ile Pro Cys His Tyr Ser Val Asp
    370                 375                 380

Asp Leu Ser Gly Lys Ala Lys Cys Lys Gly Ala Leu Gln Lys Glu Leu
385                 390                 395                 400

Gly Leu Pro Ile Arg Pro Asp Val Pro Leu Ile Gly Phe Ile Gly Arg
                405                 410                 415

Leu Asp Tyr Gln Lys Gly Ile Asp Leu Ile Gln Leu Ile Ile Pro Asp
            420                 425                 430

Leu Met Arg Glu Asp Val Gln Phe Val Met Leu Gly Ser Gly Asp Pro
        435                 440                 445

Glu Leu Glu Asp Trp Met Arg Ser Thr Glu Ser Ile Phe Lys Asp Lys
    450                 455                 460

Phe Arg Gly Trp Val Gly Phe Ser Val Pro Val Ser His Arg Ile Thr
465                 470                 475                 480

Ala Gly Cys Asp Ile Leu Leu Met Pro Ser Arg Phe Glu Pro Cys Gly
                485                 490                 495

Leu Asn Gln Leu Tyr Ala Met Gln Tyr Gly Thr Val Pro Val Val His
            500                 505                 510

Ala Thr Gly Gly Leu Arg Asp Thr Val Glu Asn Phe Asn Pro Phe Gly
        515                 520                 525

Glu Asn Gly Glu Gln Gly Thr Gly Trp Ala Phe Ala Pro Leu Thr Thr
    530                 535                 540

Glu Asn Met Phe Val Asp Ile Ala Asn Cys Asn Ile Tyr Ile Gln Gly
545                 550                 555                 560

Thr Gln Val Leu Leu Gly Arg Ala Asn Glu Ala Arg His Val Lys Arg
                565                 570                 575

Leu His Val Gly Pro Cys Arg *
            580

TABLE 5 mRNA Sequence and Deduced Amino Acid Sequence of
The Maize Branching Enzyme II Gene and the Transit Peptide
[SEQ ID NO:14 and SEQ ID NO: 15]

| | |
|---|---|
| LOCUS | MZEGLUCTRN 2725 bp ss-mRNA PLN |
| DEFINITION | Corn starch branching enzyme II mRNA, complete cds. |
| ACCESSION | L08065 |
| KEYWORDS | 1,4-alpha-glucan branching enzyme; ainylo-transglycosylase; glucanotransferase; starch branching enzyme II. |
| SOURCE | Zea mays cDNA to mRNA. |

TABLE 5-continued mRNA Sequence and Deduced Amino Acid Sequence of The Maize Branching Enzyme II Gene and the Transit Peptide
[SEQ ID NO:14 and SEQ ID NO: 15]

```
ORGANISM    Zea mays
            Eukaryota; Plantae; Embryobionta; Magnoliophyta; Liliopsida;
            Commelinidae; Cyperales; Poaceae.
REFERENCE   1 (bases 1 to 2725)
AUTHORS     Fisher, D. K., Boyer, C. D. and Hannah, L. C.
TITLE       Starch branching enzyme II from maize endosperm
JOURNAL     Plant Physiol. 102, 1045-1046 (1993)
STANDARD    full automatic
COMMENT     NCBI gi: 168482
    FEATURES        Location/Qualifiers
    source          1 . . . 2725
                    /cultivar="W64Ax182E"
                    /dev_stage="29 days post pollenation"
                    /tissue_type="endosperm"
                    /organism="Zea mays"
    sig_peptide     91 . . . 264
                    /codon start=1
    CDS             91 . . . 2490
                    /EC_number="2.4.1.18"
                    /note="NCBI gi: 168483"
                    /codon_start=1
                    /product="starch branching enzyme II"
```

/translation="MAFRVSGAVLGGAVRAPRLTGGGEGSLVFRHTGLFLTRGARVGC

SGTHGAMRAAAAARKAVMVPEGENDGLASRADSAQFQSDELEVPDISEETTCGAGVAD

AQALNRVRVVPPPSDGQKIFQIDPMLQGYKYHLEYRYSLYRRIRSDIDEHEGGLEAFS

RSYEKFGFNASAEGITYREWAPGAFSAALVGDVNNWDPNADRMSKNEFGVWEIFLPNN

ADGTSPIPHGSRVKVRMDTPSGIKDSIPAWIKYSVQAPGEIPYDGIYYDPPEEVXYVF

RHAQPKRPKSLRIYETHVGMSSPEPKINTYVNFRDEVLPRIKKLGYNAVQIMAIQEHS

YYGSFGYHVTNFFAPSSRFGTPEDLKSLIDRAHELGLLVLMDVVHSHASSNTLDGLNG

FDGTDTHYFHSGPRGHHWMWDSPLFNYGNWEVLRFLLSNARWWLEEYKFDGFRFDGVT

SMMYTHHGLQVTFTGNFNEYFGFATDVDAVVYLMLVNDLIHGLYPEAVTIGEDVSGMP

TFALPVHDGGVGFDYRMHMAVADKWIDLLKQSDETWKMGDIVHTLTNRRWLEKCVTYA

ESHDQALVGDKTIAFWLMDKDMYDFMALDRPSTPTIDRGIALHKMIRLITMGLGGEGY

LNFMGNEFGHPEWIDFPRGPQRLPSGKFIPGNNNSYDKCRRRFDLGDADYLRYHGMQE

FDQAMQHLEQKYEFMTSDHQYISRKHEEDKVIVFEKGDLVFVFNFHCNNSYFDYRIGC

RKPGVYKVVLDSDACLFGGFSRIHHAAEHFTADCSHDNRPYSFSVYTPSRTCVVYAPV

E",

```
    mat_peptide     265 . . . 2487
                    /codon start=1
                    /product="starch branching enzyme II"
BASE COUNT   727 A    534 C    715 G    749 T
ORIGIN
           GGCCCAGAGC AGACCCGGAT TCGCTCTTG CGGTCGCTGG GGTTTTAGCA TTGGCTGATC
       61  AGTTCGATCC GATCCGGCTG CGAAGGCGAG ATGGCGTTCC GGGTTTCTGG GGCGGTGCTC
      121  GGTGGGGCCG TAAGGGCTCC CCGACTCACC GGCGGCGGGG AGGGTAGTCT AGTCTTCCGG
      181  CACACCGGCC TCTTCTTAAC TCGGGGTGCT CGAGTTGGAT GTTCGGGGAC GCACGGGGCC
      241  ATGCGCGCGG CGGCCGCGGC CAGGAAGGCG GTCATGGTTC CTGAGGGCGA GAATGATGGC
      301  CTCGCATCAA GGGCTGACTC GGCTCAATTC CAGTCGGATG AACTGGAGGT ACCAGACATT
      361  TCTGAAGAGA CAACGTGCGG TGCTGGTGTG GCTGATGCTC AAGCCTTGAA CAGAGTTCGA
      421  GTGGTCCCCC CACCAAGCGA TGGACAAAAA ATATTCCAGA TTGACCCCAT GTTGCAAGGC
      481  TATAAGTACC ATCTTGAGTA TCGGTACAGC CTCTATAGAA GAATCCGTTC AGACATTGAT
```

TABLE 5-continued mRNA Sequence and Deduced Amino Acid Sequence of
The Maize Branching Enzyme II Gene and the Transit Peptide
[SEQ ID NO:14 and SEQ ID NO: 15]

```
 541 GAACATGAAG GAGGCTTGGA AGCCTTCTCC CGTAGTTATG AGAAGTTTGG ATTTAATGCC

601 AGCGCGGAAG GTATCACATA TCGAGAATGG GCTCCTGGAG CATTTTCTGC AGCATTGGTG

661 GGTGACGTCA ACAACTGGGA TCCAAATGCA GATCGTATGA GCAAAAATGA GTTTGGTGTT

721 TGGGAAATTT TTCTGCCTAA CAATGCAGAT GGTACATCAC CTATTCCTCA TGGATCTCGT

781 GTAAAGGTGA GAATGGATAC TCCATCAGGG ATAAAGGATT CAATTCCAGC CTGGATCAAG

841 TACTCAGTGC AGGCCCCAGG AGAAATACCA TATGATGGGA TTTATTATGA TCCTCCTGAA

901 GAGGTAAAGT ATGTGTTCAG GCATGCGCAA CCTAAACGAC CAAAATCATT GCGGATATAT

961 GAAACACATG TCGGAATGAG TAGCCCGGAA CCGAAGATAA ACACATATGT AAACTTTAGG

1021 GATGAAGTCC TCCCAAGAAT AAAAAAACTT GGATACAATG CAGTGCAAAT AATGGCAATC

1081 CAAGAGCACT CATATTATGG AAGCTTTGGA TACCATGTAA CTAATTTTTT TGCGCCAAGT

1141 AGTCGTTTTG GTACCCCAGA AGATTTGAAG TCTTTGATTG ATAGAGCACA TGAGCTTGGT

1201 TTGCTAGTTC TCATGGATGT GGTTCATAGT CATGCGTCAA GTAATACTCT GGATGGGTTG

1261 AATGGTTTTG ATGGTACAGA TACACATTAC TTTCACAGTG GTCCACGTGG CCATCACTGG

1321 ATGTGGGATT CTCGCCTATT TAACTATGGG AACTGGGAAG TTTTAAGATT TCTTCTCTCC

1381 AATGCTAGAT GGTGGCTCGA GGAATATAAG TTTGATGGTT TCCGTTTTGA TGGTGTGACC

1441 TCCATGATGT ACACTCACCA CGGATTACAA GTAACATTTA CGGGGAACTT CAATGAGTAT

1501 TTTGGCTTTG CCACCGATGT AGATGCAGTG GTTTACTTGA TGCTGGTAAA TGATCTAATT

1561 CATGGACTTT ATCCTGAGGC TGTAACCATT GGTGAAGATG TTAGTGGAAT GCCTACATTT

1621 GCCCTTCCTG TTCACGATGG TGCGGTAGGT TTTGACTATC GGATGCATAT GGCTGTGGCT

1681 GACAAATGGA TTGACCTTCT CAAGCAAAGT GATGAAACTT GGAAGATGGG TGATATTGTG

1741 CACACACTGA CAAATAGGAG GTGGTTAGAG AAGTGTGTAA CTTATGCTGA AAGTCATGAT

1801 CAAGCATTAG TCGGCGACAA GACTATTGCG TTTTGGTTGA TGGACAAGGA TATGTATGAT

1861 TTCATGGCCC TCGATAGACC TTCAACTCCT ACCATTGATC GTGGGATAGC ATTACATAAG

1921 ATGATTAGAC TTATCACAAT GGGTTTAGGA GGACAGGGCT ATCTTAATTT CATGGGAAAT

1981 GAGTTTGGAC ATCCTGAATG GATAGATTTT CCAAGAGGTC CGCAAAGACT TCCAAGTGGT

2041 AAGTTTATTC CAGGGAATAA CAACAGTTAT GACAAATGTC GTCGAAGATT TGACCTGGGT

2101 GATGCAGACT ATCTTAGGTA TCATGGTATG CAAGAGTTTG ATCAGGCAAT GCAACATCTT

2161 GAGCAAAAAT ATGAATTCAT GACATCTGAT CACCAGTATA TTTCCCGGAA ACATGAGGAG

2221 GATAAGGTGA TTGTGTTCGA AAAGGGAGAT TTGGTATTTG TGTTCAACTT CCACTGCAAC

2281 AACAGCTATT TTGACTACCG TATTGGTTGT CGAAAGCCTG GGGTGTATAA GGTGGTCTTG

2341 GACTCCGACG CTGGACTATT TGGTGGATTT AGCAGGATCC ATCACGCAGC CGAGCACTTC

2401 ACCGCCGACT GTTCGCATGA TAATAGGCCA TATTCATTCT CGGTTTATAC ACCAAGCAGA

2461 ACATGTGTCG TCTATGCTCC AGTGGAGTGA TAGCGGGGTA CTCGTTGCTG CGCGGCATGT

2521 GTGGGGCTGT CGATGTGAGG AAAAACCTTC TTCCAAAACC GGCAGATGCA TGCATGCATG

2581 CTACAATAAG GTTCTGATAC TTTAATCGAT GCTGGAAAGC CCATGCATCT CGCTGCGTTG
```

TABLE 5-continued mRNA Sequence and Deduced Amino Acid Sequence of
The Maize Branching Enzyme II Gene and the Transit Peptide
[SEQ ID NO:14 and SEQ ID NO: 15]

```
2641 TCCTCTCTAT ATATATAAGA CCTTCAAGGT GTCAATTAAA CATAGAGTTT TCGTTTTTCG

2701 CTTTCCTAAA AAAAAAAAAA AAAAA
//
```

TABLE 6 mRNA Sequence and Deduced Amino Acid Sequence of the
Maize Branching Enzyme I and the Transit Peptide
[SEQ ID NO:16 and SEQ ID NO:17]

```
LOCUS       MZEBEI     2763 bp ss-mRNA      PLN
DEFINITION  Maize mRNA for branching enzyme-I (BE-I).
ACCESSION   D11081
KEYWORDS    branching enzyme-I.
SOURCE      Zea mays L. (inbred Oh43), cDNA to mRNA.
ORGANISM    Zea mays
            Eukaryota; Plantae; Embryobionta; Magnoliophyta;
            Liliopsida; Commelinidae; Liliopsida.
REFERENCE   1 (bases 1 to 2763)
AUTHORS     Baba, T., Kimura, K., Mizuno, K., Etoh, H., Ishida, Y.,
            Shida, O. and Arai,Y.
TITLE       Sequence conservation of the catalytic regions of
            Amylolytic. enzymes in maize branching enzyme-I
JOURNAL     Biochem. Biophys. Res. Cominun. 181, 87–94 (1991)
STANDARD    full automatic
COMMENT     Submitted (30-APR-1992) to DDBJ by: Tadashi Baba
            Institute of Applied Biochemistry
            University of Tsukuba
            Tsukuba, Ibaraki 305
            Japan
            Phone: 0298-53-6632
            Fax: 0298-53-6632.
            NCBI gi: 217959
FEATURES            Location/Qualifiers
     source         1 . . . 2763
                    /organism="Zea mays"
     CDS            <1 . . . 2470
                    /note="NCBI gi:. 217960"
                    /codon_start=2
                    /product="branching enzyme-I precursor"
```

/translation="LCLVSPSSSPTPLPPPRRSRSHADRAAPPGIAGGGNVRLSVLSV

QCKARRSGVRKVKSKFATAATVQEDKTMATAKGDVDHLPIYDLDPKLEIFKDHFRYRM

KRFLEQKGSIEENEGSLESFSKGYLKFGINTNEDGTVYREWAPAAQEAELIGDFNDWN

GANHKMEKDKFGVWSIKIDHVKGKPAIPHNSKVKFRFLHGGVWVDRIPALIRYATVDA

SKFGAPYDGVHWDPPASERYTFKHPRPSKPAAPRIYEAHVGMSGEKPAVSTYREFADN

VLPRIRANNYNTVQLMAVMEHSYYASFGYHVTNFFAYSSRSGTPEDLKYLVDKAHSLG

LRVLMDVVHSHASNNVTDGLNGYDVGQSTQESYFHAGDRGYHKLWDSRLFNYANWEVL

RFLLSNLRYWLDEFMFDGFRFDGVTSMLYHHHGINVGFTGNYQEYFSLDTAVDAVVYM

MLANHLMHKLLPEATVVAEDVSGMPVLCRPVDEGGVGFDYRLAMAIPDRWIDYLKNKD

DSEWSMGEIAHTLTNRRYTEKCIAYAESHDQSIVGDKTIAFLLMDKEMYTGMSDLQPA

SPTIDRGIALQKMIHFITMALGGDGYLNFMGNEFGHPEWIDFPREGNNWSYDKCRRQW

SLVDTDHLRYXYMNAFDQAMNALDERFSFLSSSXQIVSDMNDEEKVIVFERGDLVFVF

NFHPKKTYEGYKVGCDLPGKYRVALDSDALVFGGHGRVGHDVDHFTSPEGVPGVPETN

FNNRPNSFKVLSPPRTCVAYYRVDEAGAGRRLHAKAETGKTSPAESIDVKASRASSKE

DKEATAGGKKGWKFARQPSDQDTK"

TABLE 6-continued mRNA Sequence and Deduced Amino Acid Sequence of the
Maize Branching Enzyme I and the Transit Peptide
[SEQ ID NO:16 and SEQ ID NO:17]

```
    transit_peptide  2 . . . 190
    mat_peptide      191 . . . 2467
                     /EC number="2.4.1.18"
                     /codon_start=1
                     /product="branching enzyme-I precursor"
    polyA_signal     2734 . . . 2739
BASE COUNT  719 A    585 C    737 G    722 T
ORIGIN
        1 GCTGTGCCTC GTGTCGCCCT CTTCCTCGCC GACTCCGCTT CCGCCGCCGC GGCGCTCTCG
       61 CTCGCATGCT GATCGGGCGG CACCGCCGGG GATCGCGGGT GGCGGCAATG TGCGCCTGAG
      121 TGTGTTGTCT GTCCAGTGCA AGGCTCGCCG GTCAGGGGTG CGGAAGGTCA AGAGCAAATT
      181 CGCCACTGCA GCTACTGTGC AAGAAGATAA AACTATGGCA ACTGCCAAAG GCGATGTCGA
      241 CCATCTCCCC ATATACGACC TGGACCCCAA GCTGGAGATA TTCAAGGACC ATTTCAGGTA
      301 CCGGATGAAA AGATTCCTAG AGCAGAAAGG ATCAATTGAA GAAAATGAGG GAAGTCTTGA
      361 ATCTTTTTCT AAAGGCTATT TGAAATTTGG GATTAATACA AATGAGGATG GAACTGTATA
      421 TCGTGAATGG GCACCTGCTG CGCAGGAGGC AGAGCTTATT GGTGACTTCA ATGACTGGAA
      481 TGGTGCAAAC CATAAGATGG ACAAGGATAA ATTTCGTGTT TGGTCGATCA AAATTGACCA
      541 TGTCAAAGGG AAACCTGCCA TCCCTCACAA TTCCAAGGTT AAATTTCGCT TTCTACATGG
      601 TGGAGTATGG GTTGATCGTA TTCCAGCATT GATTCGTTAT GCGACTGTTG ATGCCTCTAA
      661 ATTTGGAGCT CCCTATGATG GTGTTCATTG GGATCCTCCT GCTTCTGAAA GGTACACATT
      721 TAAGCATCCT CGGCCTTCAA AGCCTGCTGC TCCACGTATC TATGAAGCCC ATGTAGGTAT
      782 GAGTGGTGAA AAGCCAGCAG TAAGCACATA TAGGGAATTT GCAGACAATG TGTTGCCACG
      841 CATACGAGCA AATAACTACA ACACAGTTCA GTTGATGGCA GTTATGGAGC ATTCGTACTA
      901 TGCTTCTTTC GGGTACCATG TGACAAATTT CTTTGCGGTT AGCAGCAGAT CAGGCACACC
      961 AGAGGACCTC AAATATCTTG TTGATAAGGC ACACAGTTTG GGTTTGCGAG TTCTGATGGA
     1021 TGTTGTCCAT AGCCATGCAA GTAATAATGT CACAGATGGT TTAAATGGCT ATGATGTTGG
     1081 ACAAAGCACC CAAGAGTCCT ATTTTCATGC GGGAGATAGA GGTTATCATA AACTTTGGGA
     1141 TAGTCGGCTG TTCAACTATG CTAACTGGGA GGTATTAAGG TTTCTTCTTT CTAACCTGAG
     1201 ATATTGGTTG GATGAATTCA TGTTTGATGG CTTCCGATTT GATGGAGTTA CATCAATGCT
     1261 GTATCATCAC CATGGTATCA ATGTGGGGTT TACTGGAAAC TACCAGGAAT ATTTCAGTTT
     1321 GGACACAGCT GTGGATGCAG TTGTTTACAT GATGCTTGCA AACCATTTAA TGCACAAACT
     1381 CTTGCCAGAA GCAACTGTTG TTGCTGAAGA TGTTTCAGGC ATGCCGGTCC TTTGCCGGCC
     1441 AGTTGATGAA GGTGGGGTTG GGTTTGACTA TCGCCTGGCA ATGGCTATCC CTGATAGATG
     1501 GATTGACTAC CTGAAGAATA AAGATGACTC TGAGTGGTCG ATGGGTGAAA TAGCGCATAC
     1561 TTTGACTAAC AGGAGATATA CTGAAAAATG CATCGCATAT GCTGAGAGCC ATGATCAGTC
     1621 TATTGTTGGC GACAAAACTA TTGCATTTCT CCTGATGGAC AAGGAAATGT ACACTGGCAT
     1681 GTCAGACTTG CAGCCTGCTT CACCTACAAT TGATCGAGGG ATTGCACTCC AAAAGATGAT
     1741 TCACTTCATC ACAATGGCCC TTGGAGGTGA TGGCTACTTG AATTTTATGG GAAATGAGTT
     1801 TGGTCACCCA GAATGGATTG ACTTTCCAAG AGAAGGGAAC AACTGGAGCT ATGATAAATG
     1861 CAGACGACAG TGGAGCCTTG TGGACACTGA TCACTTGCGG TACAAGTACA TGAATGCGTT
     1921 TGACCAAGCG ATGAATGCGC TCGATGAGAG ATTTTCCTTC CTTTCGTCGT CAAAGCAGAT
```

TABLE 6-continued mRNA Sequence and Deduced Amino Acid Sequence of the
Maize Branching Enzyme I and the Transit Peptide
[SEQ ID NO:16 and SEQ ID NO:17]

```
1981 CGTCAGCGAC ATGAACGATG AGGAAAAGGT TATTGTCTTT GAACGTGGAG ATTTAGTTTT

2041 TGTTTTCAAT TTCCATCCCA AGAAAACTTA CGAGGGCTAC AAAGTGGGAT GCGATTTGCC

2101 TGGGAAATAC AGAGTAGCCC TGGACTCTGA TGCTCTGGTC TTCGGTGGAC ATGGAAGAGT

2161 TGGCCACGAC GTGGATCACT TCACGTCGCC TGAAGGGGTG CCAGGGGTGC CCGAAACGAA

2221 CTTCAACAAC CGGCCGAACT CGTTCAAAGT CCTTTCTCCG CCCCGCACCT GTGTGGCTTA

2281 TTACCGTGTA GACGAAGCAG GGGCTGGACG ACGTCTTCAC GCGAAAGCAG AGACAGGAAA

2341 GACGTCTCCA GCAGAGAGCA TCGACGTCAA AGCTTCCAGA GCTAGTAGCA AAGAAGACAA

2401 GGAGGCAACG GCTGGTGGCA AGAAGGGATG GAAGTTTGCG CGGCAGCCAT CCGATCAAGA

2461 TACCAAATGA AGCCACGAGT CCTTGGTGAG GACTGGACTG GCTGCCGGCG CCCTGTTAGT

2521 AGTCCTGCTC TACTGGACTA GCCGCCGCTG GCGCCCTTGG AACGGTCCTT TCCTGTAGCT

2581 TGCAGGCGAC TGGTGTCTCA TCACCGAGCA GGCAGGCACT GCTTGTATAG CTTTTCTAGA

2641 ATAATAATCA GGGATGGATG GATGGTGTGT ATTGGCTATC TGGCTAGACG TGCATGTGCC

2701 CAGTTTGTAT GTACAGGAGC AGTTCCCGTC CAGAATAAAA AAAAACTTGT TGGGGGGTTT

2761 TTC
//
```

TABLE 7

Coding Sequence and Deduced Amino Acid Sequence for
Transit Peptide Region of the
Soluble Starch Synthase I Maize Gene (153 bp)
[SEQ ID NO:18 and SEQ ID NO: 19]

```
FILE NAME          MSS1TRPT.DNA SEQUENCE NORMAL    153 BP
CODON TABLE        UNIV.TCN
SEQUENCE REGION    1–153
TRANSLATION REGION 1–153
   *** DNA TRANSLATION ***

1  ATG GCG ACG CCC TCG GCC GTG GGC GCC GCG TGC CTC CTC CTC GCG CGG  48
  1   M   A   T   P   S   A   V   G   A   A   C   L   L   L   A   R  16

49  GCC GCC TGG CCG GCC GCC GTC GGC GAC CGG GCG CGC CCG CGG AGG CTC  96
 17   A   A   W   P   A   A   V   G   D   R   A   R   P   R   R   L  32

97  CAG CGC GTG CTG CGC CGC CGG TGC GTC GCG GAG CTG AGC AGG GAG GGG 144
 33   Q   R   V   L   R   R   R   C   V   A   E   L   S   R   E   G  48

145  CCC CAT ATG                                                      153
 49   P   H   M                                                        51
```

GFP constructs:

1. GFP only in pET-21a:

pEXS115 is digested with Nde I and Xho I and the 740 bp fragment containing the SGFP coding sequence is subcloned into the Nde I and Xho I sites of pET-21a (Novagen 601 Science Dr. Madison Wis.). (See FIG. 2b GFP-21a map.)

Figure 3A:
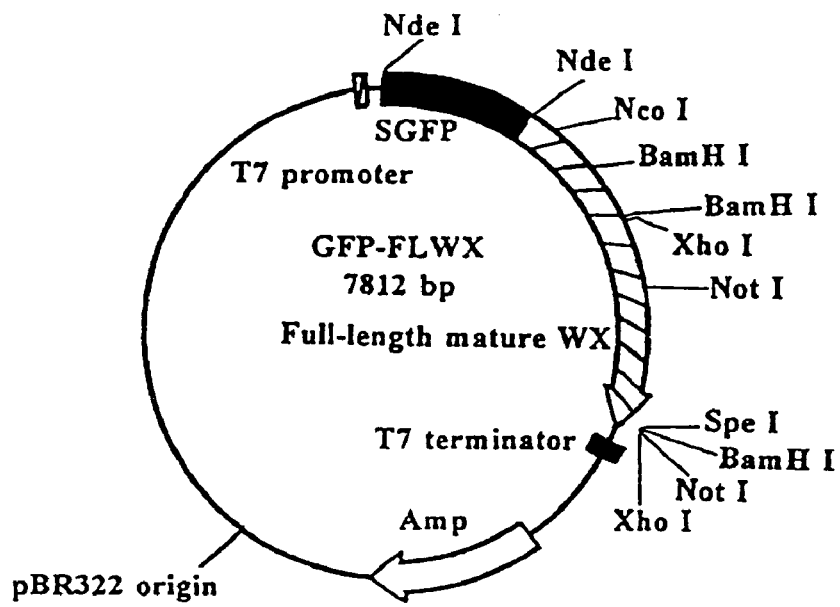
FIG. 3A shows pEXS114 subcloned into pEXSWX, and the GFP-FLWX map.

2. GFP subcloned in-frame at the 5' end of full-length mature WX:

The 740 bp Nde I fragment containing SGFP from pEXS114 is subcloned into the Nde I site of pEXSWX. (See FIG. 3a GFP-FLWX map.)

3. GFP subcloned in-frame at the 5' end of N-terminally truncated WX:

WX truncated by 700 bp at N-terminus.

Figure 3B:
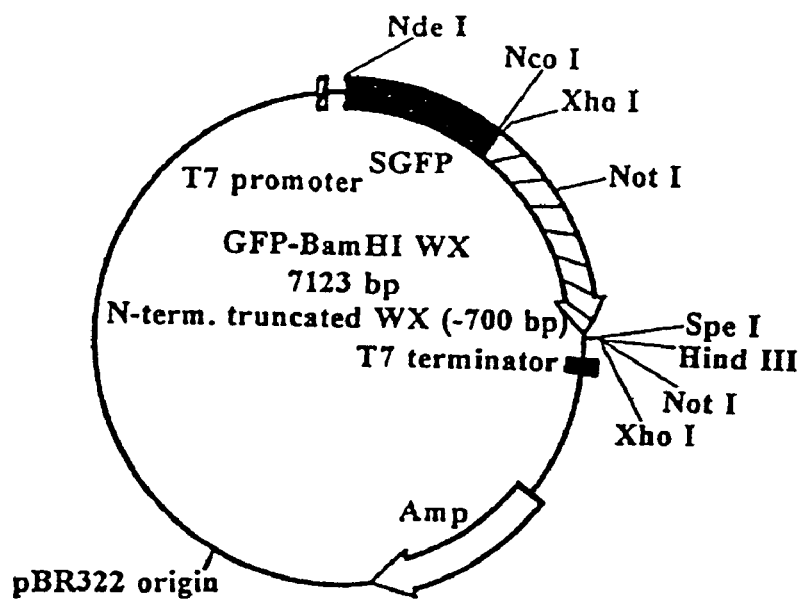
FIG. 3B shows the GFP-Bam HIWX plasmid.

The 1 kb BamH I fragment encoding the C-terminus of WX from pEXSWX is subcloned into the Bgl II site of pEXS 115. Then the entire SGFP-truncated WX fragment is subcloned into pET21a as a Nde I-HindIII fragment. (See FIG. 3b GFP-BamHIWX map.)

4. GFP subcloned in-frame at the 5' end of truncated WX:

WX truncated by 100 bp at N-terminus.

Figure 4:
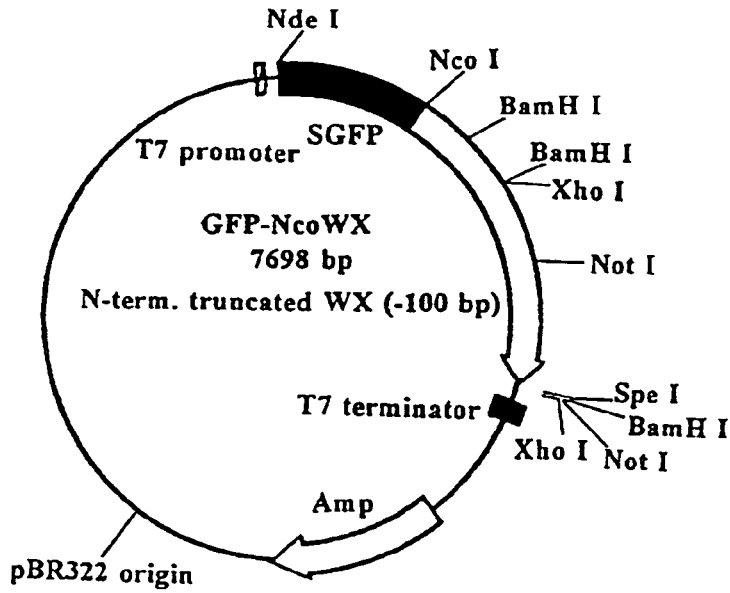
FIG. 4 shows the SGFP fragment of pEXS115 subcloned into pEXSWX, and the GFP-NcoWX map.
Figure 5:
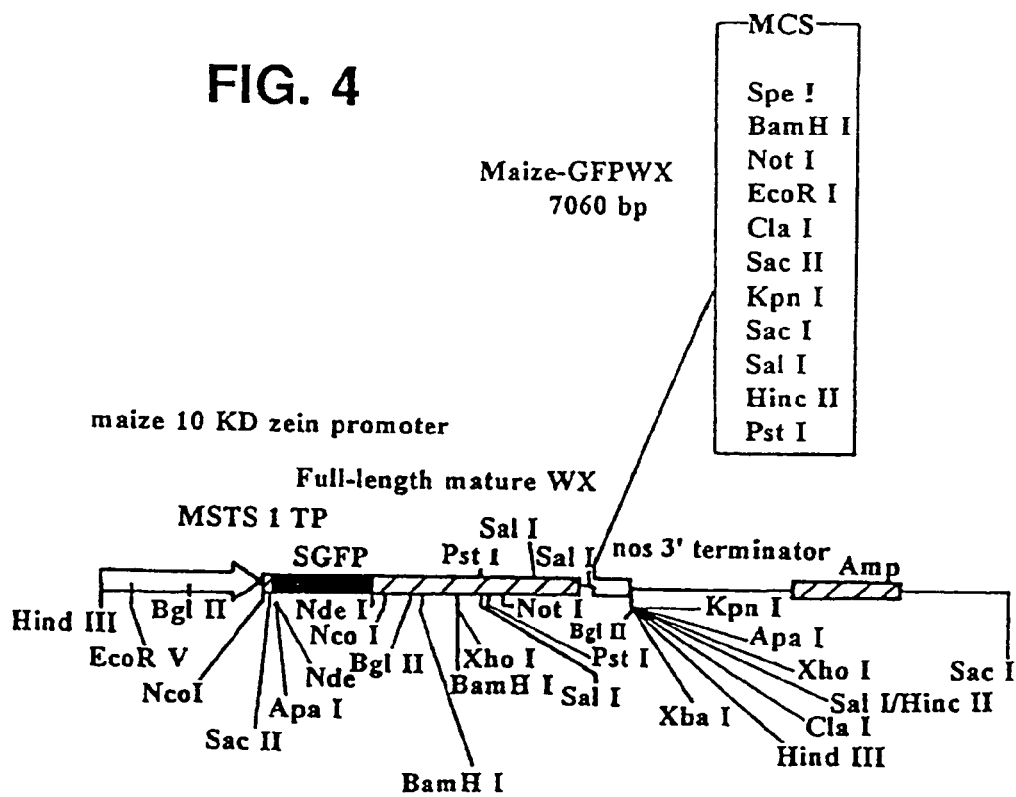
FIG. 5 shows a linear depiction of a plasmid that is adapted for use in monocots.

The 740 bp Nde I-Nco I fragment containing SGFP from pEXS115 is subcloned into pEXSWX at the Nde I and Nco I sites. (See FIG. 4 GFP-NcoWX map.)

Example Three

Plasmid Transformation into Bacteria:

*Escherichia coli* competent cell preparation:
1. Inoculate 2.5 ml LB media with a single colony of desired *E. coli* strain: selected strain was XLIBLUE DL2IDE3 from (Stratagene); included appropriate antibiotics. Grow at 37° C., 250 rpm overnight.
2. Inoculate 100 ml of LB media with a 1:50 dilution of the overnight culture, including appropriate antibiotics. Grow at 37° C., 250 rpm until $OD_{600}$=0.3–0.5.
3. Transfer culture to sterile centrifuge bottle and chill on ice for 15 minutes.
4. Centrifuge 5 minutes at 3,000×g (4° C.).
5. Resuspend pellet in 8 ml ice-cold Transformation buffer. Incubate on ice for 15 minutes.
6. Centrifuge 5 minutes at 3,000×g (4° C.).
7. Resuspend pellet in 8 ml ice-cold Transformation buffer 2. Aliquot, flash-freeze in liquid nitrogen, and stored at −70° C.

| Transformation Buffer 1 | | Transformation Buffer 2 | |
|---|---|---|---|
| RbCl | 1.2 g | MOPS (10 mM) | 0.209 g |
| $MnCl_2$ $4H_2O$ | 0.99 g | RbCl | 0.12 g |
| K-Acetate | 0.294 g | $CaCl_2$ $2H_2O$ | 1.1 g |
| $CaCl_2$ $2H_2O$ | 0.15 g | Glycerol | 15 g |
| Glycerol | 15 g | $dH_2O$ | 100 ml |
| $dH_2O$ | 100 ml | pH to 6.8 with NaOH | |
| pH to 5.8 with 0.2 M acetic acid | | Filter sterilize | |
| Filter sterilize | | | |

*Escherichia coli* transformation by rubidium chloride heat shock method: Hanahan, D. (1985) in DNA cloning: a practical approach (Glover, D. M. ed.), pp. 109–135, IRL Press.

1. Incubate 1–5 μl of DNA on ice with 150 μl *E. coli* competent cells for 30 minutes.
2. Heat shock at 42° C. for 45 seconds.
3. Immediately place on ice for 2 minutes.
4. Add 600 μl LB media and incubate at 37° C. for 1 hour.
5. Plate on LB agar including the appropriate antibiotics.

This plasmid will express the hybrid polypeptide containing the green fluorescent protein within the bacteria.

Example Four

Expression of Construct in *E. coli*:
1. Inoculate 3 ml LB with *E. coli* containing plasmid of interest. Include appropriate antibiotics. 37° C., 250 rpm, overnight.
2. Inoculate 100 ml LB with 2 ml of overnight culture. Include appropriate antibiotics. Grow at 37° C., 250 rpm.
3. At $OD_{600}$ about 0.4–0.5, place at room temperature, 200 rpm.
4. At $OD_{600}$ about 0.6–0.8, induce with 100 μl 1M 1PTG. Final 1PTG concentration is 1 mM.
5. Grow at room temperature, 200 rpm, 4–5 hours.
6. Collect cells by centrifugation.
7. Flash freeze in liquid nitrogen and store at −70° C. until use.

Cells can be resuspended in $dH_2O$ and viewed under UV light ($\lambda_{max}$=395 nm) for intrinsic fluorescence. Alternatively, the cells can be sonicated and an aliquot of the cell extract can be separated by SDS-PAGE and viewed under UV light to detect GFP fluorescence. When the protein employed is a green fluorescent protein, the presence of the protein in the lysed material can be evaluated under UV at 395 nm in a light box and the signature green glow can be identified.

Example Five

Plasmid Extraction from Bacteria:

The following is one of many common alkaline lysis plasmid purification protocols useful in practicing this invention.
1. Inoculate 100–200 ml LB media with a single colony of *E. coli* transformed with the one of the plasmids described above. Include appropriate antibiotics. Grow at 37° C., 250 rpm overnight.
2. Centrifuge 10 minutes at 5,000×g (4° C.).
3. Resuspend cells in 10 ml water, transfer to a 15 ml centrifuge tube, and repeat centrifugation.
4. Resuspend pellet in 5 ml 0.1 M NaOH, 0.5% SDS. Incubate on ice for 10 minutes.
5. Add 2.5 ml of 3 M sodium acetate (pH 5.2), invert gently, and incubate 10 minutes on ice.
6. Centrifuge 5 minutes at 15,000–20,000×g (4° C.).
7. Extract supernatant with an equal volume of phenol:chloroform:isoamyl alcohol (25:24:1).
8. Centrifuge 10 minutes at 6,000–10,000×g (4° C.).
9. Transfer aqueous phase to clean tube and precipitate with I volume of isopropanol.
10. Centrifuge 15 minutes at 12,000×g (4° C.).
11. Dissolve pellet in 0.5 ml TE, add 20 μl of 10 mg/ml Rnase, and incubate 1 hour at 37° C.
12. Extract twice with phenol:chloroform:isoamyl alcohol (25:24:1).
13. Extract once with chloroform.
14. Precipitate aqueous phase with 1 volume of isopropanol and 0.1 volume of 3 M sodium acetate.
15. Wash pellet once with 70% ethanol.
16. Dry pellet in SpeedVac and resuspend pellet in TE.

This plasmid can then be inserted into other hosts.

TABLE 8

DNA Sequence and Deduced Amino Acid Sequence of Starch Synthase Coding Region from pEXS52 [SEQ ID NO:20; SEQ ID NO:21]

```
FILE NAME         MSS1DELN.DNA SEQUENCE NORMAL   1626 BP
CODON TABLE       UNIV.TCN
SEQUENCE REGION   1-1626
TRANSLATION REGION 1-1626
(xi) SEQUENCE DESCRIPTION: SEQ ID NO:20:

TGC GTC GCG GAG CTG AGC AGG GAG GAC CTC GGT CTC GAA CCT GAA GGG   48
Cys Val Ala Glu Leu Ser Arg Glu Asp Leu Gly Leu Glu Pro Glu Gly
```

TABLE 8-continued

DNA Sequence and Deduced Amino Acid Sequence of Starch Synthase Coding Region from pEXS52 [SEQ ID NO:20; SEQ ID NO:21]

```
                    55                      60                      65
ATT GCT GAA GGT TCC ATC GAT AAC ACA GTA GTT GTG GCA AGT GAG CAA    96
Ile Ala Glu Gly Ser Ile Asp Asn Thr Val Val Val Ala Ser Glu Gln
            70                      75                      80

GAT TCT GAG ATT GTG GTT GGA AAG GAG CAA GCT CGA GCT AAA GTA ACA   144
Asp Ser Glu Ile Val Val Gly Lys Glu Gln Ala Arg Ala Lys Val Thr
        85                      90                      95

CAA AGC ATT GTC TTT GTA ACC GGC GAA GCT TCT CCT TAT GCA AAG TCT   192
Gln Ser Ile Val Phe Val Thr Gly Glu Ala Ser Pro Tyr Ala Lys Ser
100                     105                     110                     115

GGG GGT CTA GGA GAT GTT TGT GGT TCA TTG CCA GTT GCT CTT GCT GCT   240
Gly Gly Leu Gly Asp Val Cys Gly Ser Leu Pro Val Ala Leu Ala Ala
                120                     125                     130

CGT GGT CAC CGT GTG ATG GTT GTA ATG CCC AGA TAT TTA AAT GGT ACC   288
Arg Gly His Arg Val Met Val Val Met Pro Arg Tyr Leu Asn Gly Thr
            135                     140                     145

TCC GAT AAG AAT TAT GCA AAT GCA TTT TAC ACA GAA AAA CAC ATT CGG   336
Ser Asp Lys Asn Tyr Ala Asn Ala Phe Tyr Thr Glu Lys His Ile Arg
        150                     155                     160

ATT CCA TGC TTT GGC GGT GAA CAT GAA GTT ACC TTC TTC CAT GAG TAT   384
Ile Pro Cys Phe Gly Gly Glu His Glu Val Thr Phe Phe His Glu Tyr
165                     170                     175

AGA GAT TCA GTT GAC TGG GTG TTT GTT GAT CAT CCC TCA TAT CAC AGA   432
Arg Asp Ser Val Asp Trp Val Phe Val Asp His Pro Ser Tyr His Arg
180                     185                     190                     195

CCT GGA AAT TTA TAT GGA GAT AAG TTT GGT GCT TTT GGT GAT AAT CAG   480
Pro Gly Asn Leu Tyr Gly Asp Lys Phe Gly Ala Phe Gly Asp Asn Gln
                200                     205                     210

TTC AGA TAC ACA CTC CTT TGC TAT GCT GCA TGT GAG GCT CCT TTG ATC   528
Phe Arg Tyr Thr Leu Leu Cys Tyr Ala Ala Cys Glu Ala Pro Leu Ile
            215                     220                     225

CTT GAA TTG GGA GGA TAT ATT TAT GGA CAG AAT TGC ATG TTT GTT GTC   576
Leu Glu Leu Gly Gly Tyr Ile Tyr Gly Gln Asn Cys Met Phe Val Val
        230                     235                     240

AAT CAT TGG CAT GCC AGT CTA GTG CCA GTC CTT CTT GCT GCA AAA TAT   624
Asn Asp Trp His Ala Ser Leu Val Pro Val Leu Leu Ala Ala Lys Tyr
245                     250                     255

AGA CCA TAT GGT GTT TAT AAA GAC TCC CGC AGC ATT CTT GTA ATA CAT   672
Arg Pro Tyr Gly Val Tyr Lys Asp Ser Arg Ser Ile Leu Val Ile His
260                     265                     270                     275

AAT TTA GCA CAT CAG GGT GTA GAG CCT GCA AGC ACA TAT CCT GAG CTT   720
Asn Leu Ala His Gln Gly Val Glu Pro Ala Ser Thr Tyr Pro Asp Leu
                280                     285                     290

GGG TTG CCA CCT GAA TGG TAT GGA GCT CTG GAG TGG GTA TTC CCT GAA   768
Gly Leu Pro Pro Glu Trp Tyr Gly Ala Leu Glu Trp Val Phe Pro Glu
            295                     300                     305

TGG GCG AGG AGG CAT GCC CTT GAC AAG GGT GAG GCA GTT AAT TTT TTG   816
Trp Ala Arg Arg His Ala Leu Asp Lys Gly Glu Ala Val Asn Phe Leu
        310                     315                     320

AAA GGT GCA GTT GTG ACA GCA GAT CGA ATC GTG ACT GTC AGT AAG GGT   864
Lys Gly Ala Val Val Thr Ala Asp Arg Ile Val Thr Val Ser Lys Gly
325                     330                     335

TAT TCG TGG GAG GTC ACA ACT GCT GAA GGT GGA CAG GGG CTC AAT GAG   912
Tyr Ser Trp Glu Val Thr Thr Ala Glu Gly Gly Gln Gly Leu Asn Glu
340                     345                     350                     355

CTC TTA AGC TCC AGA AAG AGT GTA TTA AAC GGA ATT GTA AAT GGA ATT   960
Leu Leu Ser Ser Arg Lys Ser Val Leu Asn Gly Ile Val Asn Gly Ile
```

TABLE 8-continued

DNA Sequence and Deduced Amino Acid Sequence of Starch
Synthase Coding Region from pEXS52 [SEQ ID NO:20; SEQ ID NO:21]

```
                         360                 365                 370
GAC ATT AAT GAT TGG AAC CCT GCC ACA GAC AAA TGT ATC CCC TGT CAT       1008
Asp Ile Asn Asp Trp Asn Pro Ala Thr Asp Lys Cys Ile Pro Cys His
                375                 380                 385

TAT TCT GTT GAT GAC CTC TCT GGA AAG GCC AAA TGT AAA GGT GCA TTG       1056
Tyr Ser Val Asp Asp Leu Ser Gly Lys Ala Lys Cys Lys Gly Ala Leu
                390                 395                 400

CAG AAG GAG CTG GGT TTA CCT ATA AGG CCT GAT GTT CCT CTG ATT GGC       1104
Gln Lys Glu Leu Gly Leu Pro Ile Arg Pro Asp Val Pro Leu Ile Gly
        405                 410                 415

TTT ATT GGA AGG TTG GAT TAT CAG AAA GGC ATT GAT CTC ATT CAA CTT       1152
Phe Ile Gly Arg Leu Asp Tyr Gln Lys Gly Ile Asp Leu Ile Gln Leu
420                 425                 430                 435

ATC ATA CCA GAT CTC ATG CGG GAA GAT GTT CAA TTT GTC ATG CTT GGA       1200
Ile Ile Pro Asp Leu Met Arg Glu Asp Val Gln Phe Val Met Leu Gly
                440                 445                 450

TCT GGT GAC CCA GAG CTT GAA GAT TGG ATG AGA TCT ACA GAG TCG ATC       1248
Ser Gly Asp Pro Glu Leu Glu Asp Trp Met Arg Ser Thr Glu Ser Ile
                455                 460                 465

TTC AAG GAT AAA TTT GGT GGA TGG GTT GGA TTT AGT GTT CCA GTT TCC       1296
Phe Lys Asp Lys Phe Gly Gly Trp Val Gly Phe Ser Val Pro Val Ser
                470                 475                 480

CAC GGA ATA ACT GCC GGC TGC GAT ATA TTG TTA ATG CCA TCC AGA TTC       1344
His Gly Ile Thr Ala Gly Cys Asp Ile Leu Leu Met Pro Ser Arg Phe
            485                 490                 495

GAA CCT TGT GGT CTC AAT CAG CTA TAT GCT ATG CAG TAT GGC ACA GTT       1392
Glu Pro Cys Gly Leu Asn Gln Leu Tyr Ala Met Gln Tyr Gly Thr Val
500                 505                 510                 515

CCT GTT GTC CAT GCA ACT GGG GGG GTT AGA GAT ACC GTG GAG AAC TTG       1440
Pro Val Val His Ala Thr Gly Gly Val Arg Asp Thr Val Glu Asn Phe
                520                 525                 530

AAC CCT TTC GGT GAG AAT GGA GAG CAG GGT ACA GGG TGG GCA TTG GCA       1488
Asn Pro Phe Gly Glu Asn Gly Glu Gln Gly Thr Gly Trp Ala Leu Ala
                535                 540                 545

CCC CTA ACC ACA GAA AAC ATG TTT GTG GAC ATT GCG AAC TGC AAT ATC       1536
Pro Leu Thr Thr Glu Asn Met Phe Val Asp Ile Ala Asn Cys Asn Ile
                550                 555                 560

TAC ATA CAG GGA ACA CAA GTC CTC CTG GGA AGG GCT AAT GAA GCG AGG       1584
Tyr Ile Gln Gly Thr Gln Val Leu Leu Gly Arg Ala Asn Glu Ala Arg
                565                 570                 575

CAT GTC AAA AGA CTT CAC GTG GGA CCA TGC CGC TGA                       1620
His Val Lys Arg Leu His Val Gly Pro Cys Arg *
580                 585                 590
```

(2) INFORMATION FOR SEQ ID NO:21:
    (i) SEQUENCE CHARACTERISTICS:
        (A) LENGTH: 540 amino acids
        (B) TYPE: amino acid
        (D) TOPOLOGY: linear
    (ii) MOLECULE TYPE: protein
    (xi) SEQUENCE DESCRIPTION: SEQ ID NO:21:

```
Cys Val Ala Glu Leu Ser Arg Glu Asp Leu Gly Leu Glu Pro Glu Gly
  1               5                  10                  15

Ile Ala Glu Gly Ser Ile Asp Asn Thr Val Val Ala Ser Glu Gln
            20                  25                  30

Asp Ser Glu Ile Val Val Gly Lys Glu Gln Ala Arg Ala Lys Val Thr
        35                  40                  45

Gln Ser Ile Val Phe Val Thr Gly Glu Ala Ser Pro Tyr Ala Lys Ser
```

TABLE 8-continued

DNA Sequence and Deduced Amino Acid Sequence of Starch
Synthase Coding Region from pEXS52 [SEQ ID NO:20; SEQ ID NO:21]

```
             50                  55                  60
Gly Gly Leu Gly Asp Val Cys Gly Ser Leu Pro Val Ala Leu Ala Ala
 65                  70                  75                  80

Arg Gly His Arg Val Met Val Met Pro Arg Tyr Leu Asn Gly Thr
                 85                  90                  95

Ser Asp Lys Asn Tyr Ala Asn Ala Phe Tyr Thr Glu Lys His Ile Arg
                100                 105                 110

Ile Pro Cys Phe Gly Gly Glu His Glu Val Thr Phe Phe His Glu Tyr
                115                 120                 125

Arg Asp Ser Val Asp Trp Val Phe Val Asp His Pro Ser Tyr His Arg
130                 135                 140

Pro Gly Asn Leu Tyr Gly Asp Lys Phe Gly Ala Phe Gly Asp Asn Gln
145                 150                 155                 160

Phe Arg Tyr Thr Leu Leu Cys Tyr Ala Ala Cys Glu Ala Pro Leu Ile
                165                 170                 175

Leu Glu Leu Gly Gly Tyr Ile Tyr Gly Gln Asn Cys Met Phe Val Val
                180                 185                 190

Asn Asp Trp His Ala Ser Leu Val Pro Val Leu Leu Ala Ala Lys Tyr
                195                 200                 205

Arg Pro Tyr Gly Val Tyr Lys Asp Ser Arg Ser Ile Leu Val Ile His
        210                 215                 220

Asn Leu Ala His Gln Gly Val Glu Pro Ala Ser Thr Tyr Pro Asp Leu
225                 230                 235                 240

Gly Leu Pro Pro Glu Trp Tyr Gly Ala Leu Glu Trp Val Phe Pro Glu
                245                 250                 255

Trp Ala Arg Arg His Ala Leu Asp Lys Gly Glu Ala Val Asn Phe Leu
                260                 265                 270

Lys Gly Ala Val Val Thr Ala Asp Arg Ile Val Thr Val Ser Lys Gly
                275                 280                 285

Tyr Ser Trp Glu Val Thr Thr Ala Glu Gly Gly Gln Gly Leu Asn Glu
        290                 295                 300

Leu Leu Ser Ser Arg Lys Ser Val Leu Asn Gly Ile Val Asn Gly Ile
305                 310                 315                 320

Asp Ile Asn Asp Trp Asn Pro Ala Thr Asp Lys Cys Ile Pro Cys His
                325                 330                 335

Tyr Ser Val Asp Asp Leu Ser Gly Lys Ala Lys Cys Lys Gly Ala Leu
                340                 345                 350

Gln Lys Glu Leu Gly Leu Pro Ile Arg Pro Asp Val Pro Leu Ile Gly
                355                 360                 365

Phe Ile Gly Arg Leu Asp Tyr Gln Lys Gly Ile Asp Leu Ile Gln Leu
370                 375                 380

Ile Ile Pro Asp Leu Met Arg Glu Asp Val Gln Phe Val Met Leu Gly
385                 390                 395                 400

Ser Gly Asp Pro Glu Leu Glu Asp Trp Met Arg Ser Thr Glu Ser Ile
                405                 410                 415

Phe Lys Asp Lys Phe Arg Gly Trp Val Gly Phe Ser Val Pro Val Ser
                420                 425                 430

His Arg Ile Thr Ala Gly Cys Asp Ile Leu Leu Met Pro Ser Arg Phe
                435                 440                 445

Glu Pro Cys Gly Leu Asn Gln Leu Tyr Ala Met Gln Tyr Gly Thr Val
```

TABLE 8-continued

DNA Sequence and Deduced Amino Acid Sequence of Starch
Synthase Coding Region from pEXS52 [SEQ ID NO:20; SEQ ID NO:21]

```
              450                 455                 460
Pro Val Val His Ala Thr Gly Gly Leu Arg Asp Thr Val Glu Asn Phe
465                 470                 475                 480

Asn Pro Phe Gly Glu Asn Gly Glu Gln Gly Thr Gly Trp Ala Phe Ala
                485                 490                 495

Pro Leu Thr Thr Glu Asn Met Phe Val Asp Ile Ala Asn Cys Asn Ile
                500                 505                 510

Tyr Ile Gln Gly Thr Gln Val Leu Leu Gly Arg Ala Asn Glu Ala Arg
            515                 520                 525

His Val Lys Arg Leu His Val Gly Pro Cys Arg  *
        530                 535                 540
```

Example Six

This experiment employs a plasmid having a maize promoter, a maize transit peptide, a starch-encapsulating region from the starch synthase I gene, and a ligated gene fragment attached thereto. The plasmid shown in FIG. 6 contains the DNA sequence listed in Table 8.

Figure 8A:
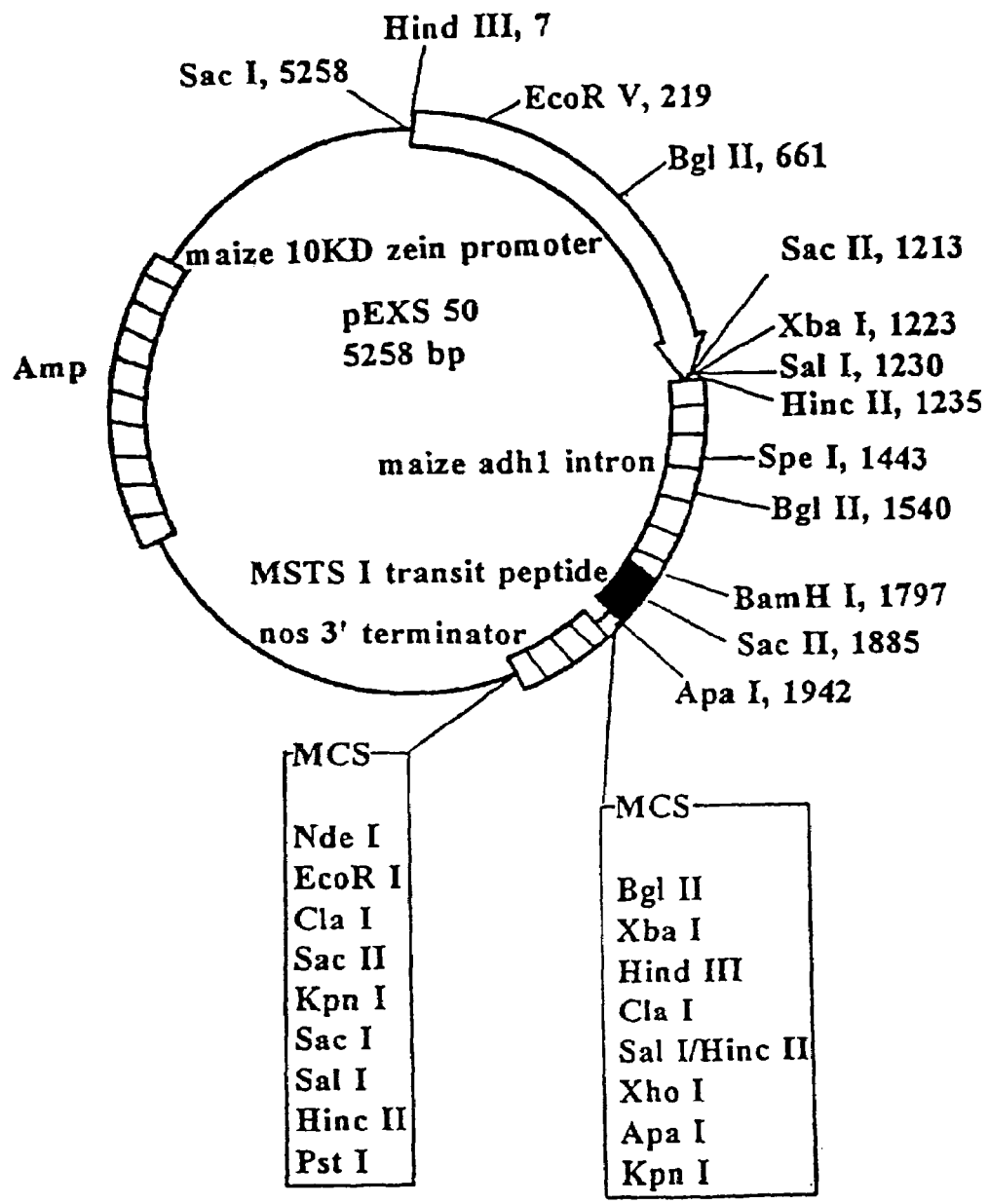
FIGS. 8a and 8b show the plasmids pEXS50 and pEXS51, respectively, containing the MS-SIII gene which is a starch-soluble synthase gene.
Figure 8B:
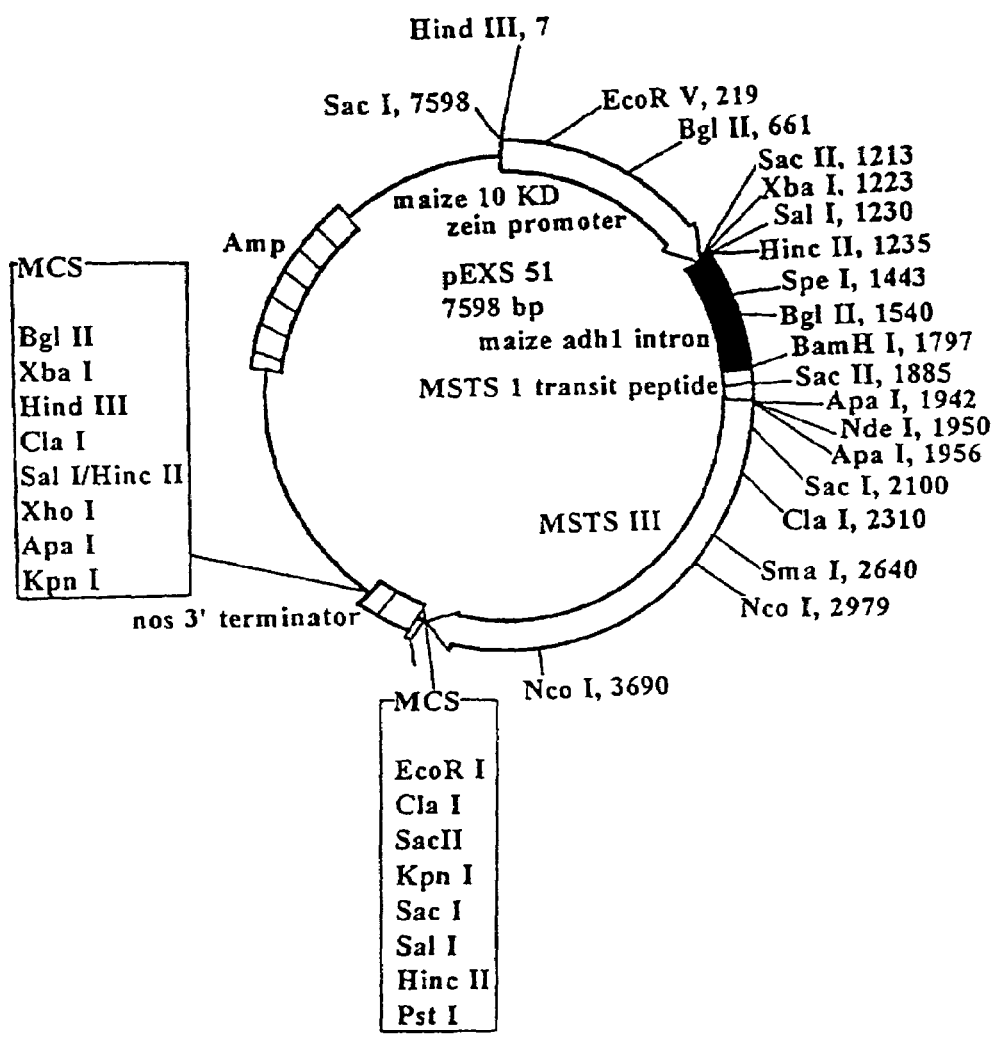
Figure 9A:
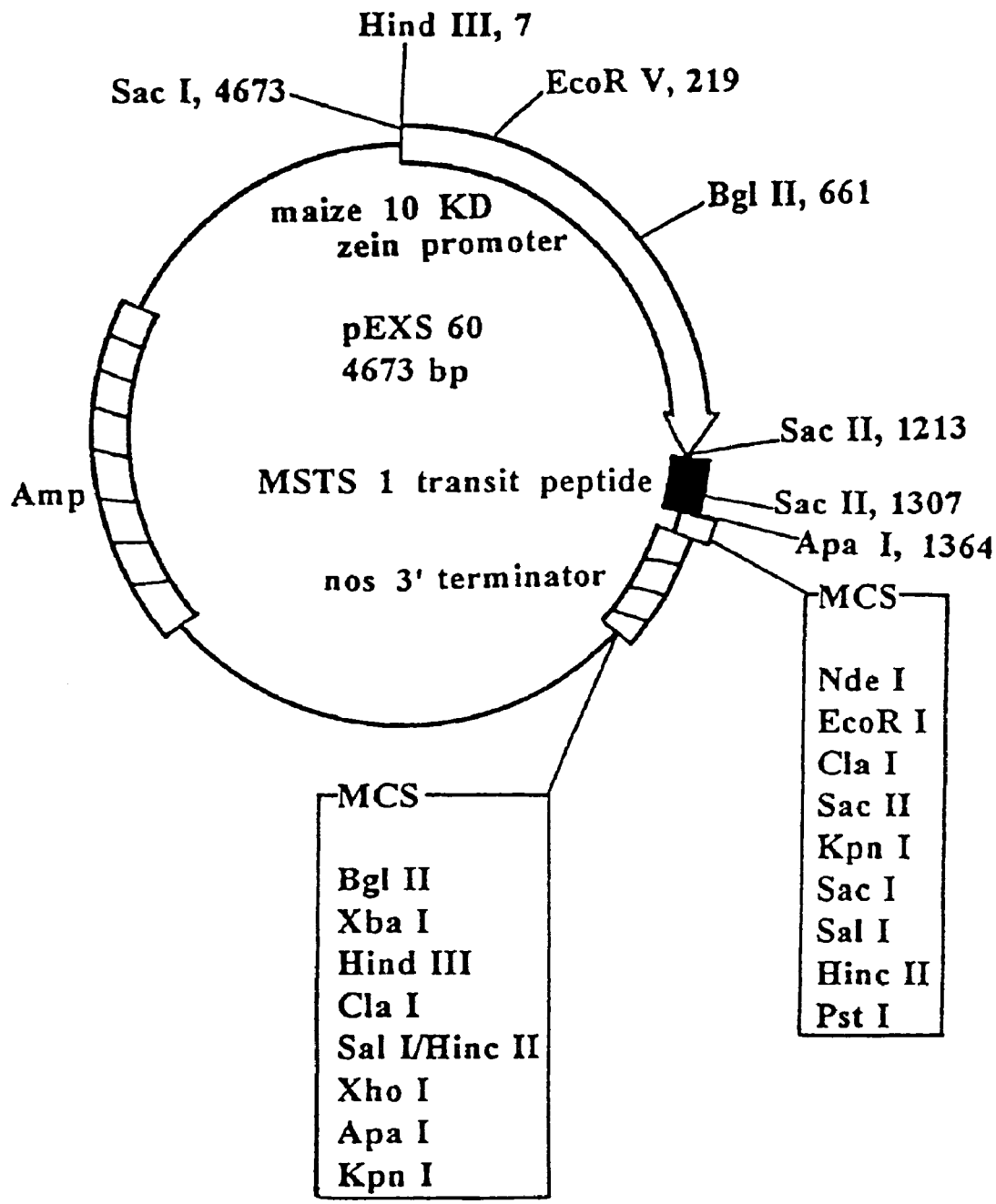
FIG. 9a shows the plasmid pEXS60 which excludes the intron shown in pEXS50.
Figure 9B:
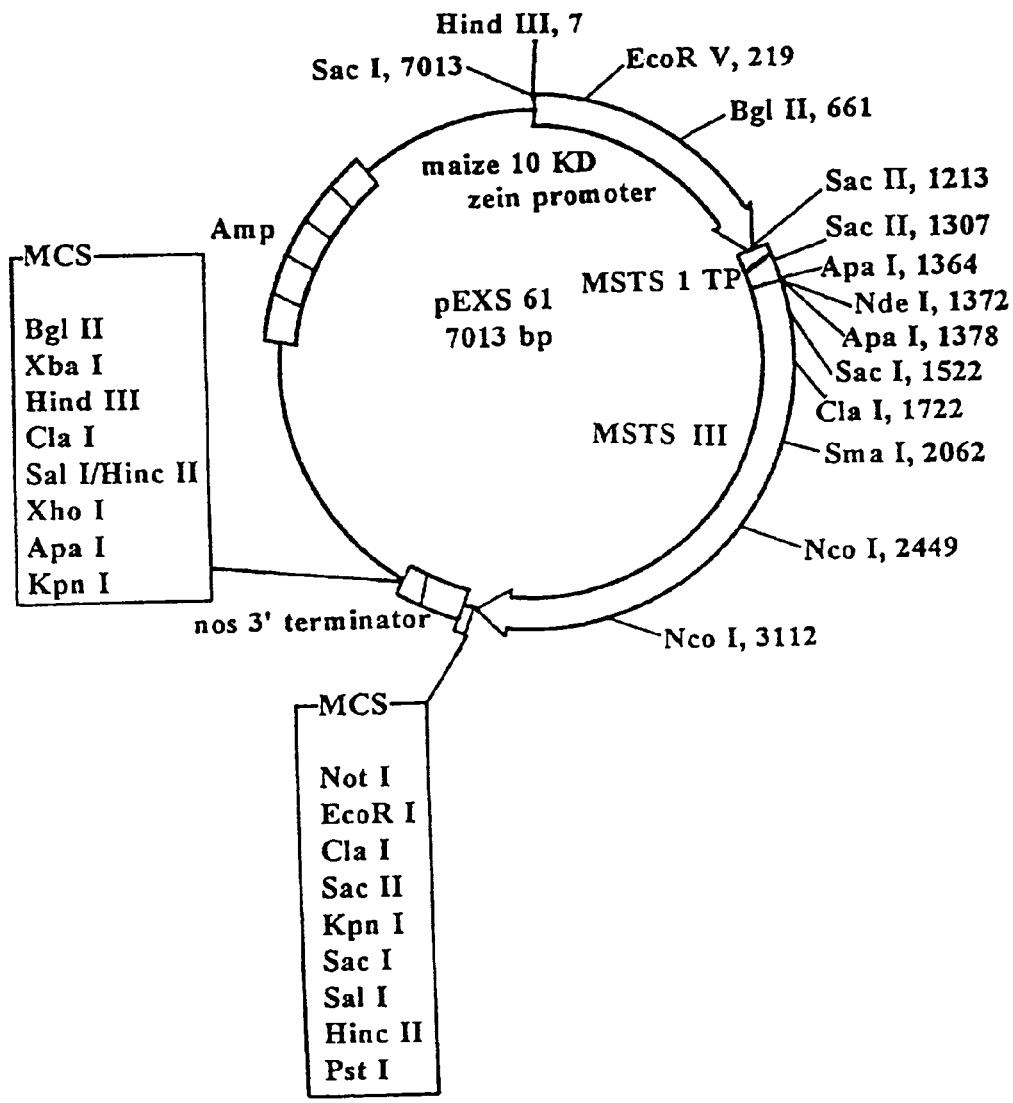
FIG. 9b shows the plasmid pEXS61 which excludes the intron shown in pEXS60.

Plasmid pEXS52 was constructed according to the following protocol:

Materials Used to Construct Transgenic Plasmids are as Follows:
Plasmid pBluescript SK-
plasmid pMF6 (contain nos3' terminator)
Plasmid pHKH1 (contain maize adh1 intron)
Plasmid MstsI(6-4) (contain maize stsI transit peptide, use as a template for PCT stsI transit peptide out)
Plasmid MstsIII in pBluescript SK-
Primers EXS29 (GTGGATCCATGGCGACGCCCTCGGC-CGTGG) [SEQ ID NO:22] EXS35 (CTGAATTC-CATATGGGGCCCCTCCCTGCTCAGCTC) [SEQ ID NO:23] both used for PCT stsI transit peptide
Primers EXS31 (CTCTGAGCTCAAGCTTGCTACMT-TCTTTCCTTAATG) [SEQ ID NO:24] EXS32 (GTCTC-CGCGGTGGTGTCCTTGCTTCCTAG) [SEQ ID NO:25] both used for PCR maize 10KD zein promoter (Journal: Gene 71:359–370 [1988])
Maize A632 genomic DNA (used as a template for PCR maize 10KD zein promoter).
Step 1: Clone maize 10KD zein promoter in pBluescriptSK- (named as pEXS10zp).
  1. PCR 1.1Kb maize 10KD zein promoter
     primers: EXS31, EXS32
     template: maize A632 genomic DNA
  2. Clone 1.1Kb maize, 10KD zein promoter PCR product into pBluescript SK-plasmid at SacI and SacII site (See FIG. 7).
Step 2: Delete NdeI site in pEXS10zp (named as pEXS10zp-NdeI).
  NdeI is removed by fill in and blunt end ligation from maize 10KD zein promoter in pBluescriptSK.
Step 3: Clone maize adh1 intron in pBluescriptSK-(named as pEXSadh1).
  Maize adh1 intron is released from plasmid pHKH1 at XbaI and BamHI sites. Maize adh1 intron (XbaI/BamHI fragment) is cloned into pBluescriptSK- at XbaI and BamHI sites (see FIG. 7).
Step 4: Clone maize 10KD zein promoter and maize adh1 intron into pBluescriptSK-(named as pEXS 10zp-adh 1).
  Maize 10KD zein promoter is released from plasmid pEXS 10zp-NdeI at SacI and SacII sites. Maize 10KD zein promoter (SacI/SacII fragment) is cloned into plasmid pEXSadh1 (contain maize adh1 intron) at SacI and SacII sites (see FIG. 7).
Step 5: Clone maize nos3' terminator into plasmid pEXSadh1 (named as pEXSadh1 nos3').
  Maize nos3' terminator is released from plasmid pMF6 at EcoRI and HindIII sites.
  Maize nos3' terminator (EcoRI/HindIII fragment) is cloned into plasmid pEXSadh1 at EcoRI and HindIII sites (see FIG. 7).
Step 6: Clone maize nos3' terminator into plasmid pEXS10zp-adh1 (named as pEXS10zp-adh1-nos3').
  Maize nos3' terminator is released from plasmid pEX-Sadh1-nos3' at EcoRI and ApaI sites. Maize nos3' terminator (EcoRI/ApaI fragment) is cloned into plasmid pEXS10zp-adh1 at EcoRI and ApaI sites (see FIG. 7).
Step 7: Clone maize STSI transit peptide into plasmid pEXS10zp-adh1-nos3' (named as pEXS33).
  1. PCR 150bp maize STSI transit peptide
     primer: EXS29, EXS35
     template: MSTSI(6-4) plasmid
  2. Clone 150bp maize STSI transit peptide PCR product into plasmid pEXS10zpadh1-nos3' at EcoRI and BamHI sites (see FIG. 7).
Step 8: Site-directed mutagenesis on maize STSI transit peptide in pEXS33 (named as pEXS33(m)).
  There is a mutation (stop codon) on maize STSI transit peptide in plasmid pEXS33. Site-directed mutagenesis is carried out to change stop codon to non-stop codon. New plasmid (containing maize 10KD zein promoter, maize STSI transit peptide, maize adh1 intron, maize nos3' terminator) is named as pEXS33(m).
Step 9: NotI site in pEXS33(m) deleted (named as pEXS50).
  NotI site is removed from pEXS33 by NotI fillin, blunt end ligation to form pEXS50 (see FIG. 8).
Step 10: Maize adh1 intron deleted in pEXS33(m) (named as pEXS60).
  Maize adh1 intron is removed by NotI/BamHI digestion, filled in with Klenow fragment, blunt end ligation to form pEXS60 (see FIG. 9).

Step 11: Clone maize STSIII into pEXS50, pEXS60.

Maize STSIII is released from plasmid maize STSIII in pBluescript SK- at NdeI and EcoRI sites. Maize STSIII (NdeI-EcoRI fragment) is cloned into pEXS50, pEXS60 separately, named as pEXS51, pEXS61 (see FIGS. 8 and 9, respectively).

Step 12: Clone the gene in Table 8 into pEXS51 at NdeI/NotI site to form pEXS52. Other similar plasmids can be made by cloning other genes (STSI, II, WX, glgA, glgB, glgC, BEI, BEII, etc.) into pEXS51, pEXS61 at NdeI/NotI site.

Plasmid EXS52 was transformed into rice. The regenerated rice plants transformed with pEXS52 were marked and placed in a magenta box.

Two siblings of each line were chosen from the magenta box and transferred into 2.5 inch pots filled with soil mix (topsoil mixed with peat-vermiculite 50/50). The pots were placed in an aquarium (fish tank) with half an inch of water. The top was covered to maintain high humidity (some holes were made to help heat escape). A thermometer monitored the temperature. The fish tank was placed under fluorescent lights. No fertilizer was used on the plants in the first week. Light period was 6 a.m.–8 p.m., minimum 14 hours light. Temperature was minimum 68° F. at night, 80°–90° F. during the day. A heating mat was used under the fish tank to help root growth when necessary. The plants stayed in the above condition for a week. (Note: the seedlings began to grow tall because of low light intensity.)

After the first week, the top of the aquarium was opened and rice transformants were transferred to growth chambers for three weeks with high humidity and high light intensity.

Alternatively, water mix in the greenhouse can be used to maintain high humidity. The plants grew for three weeks. Then the plants were transferred to 6-inch pots (minimum 5-inch pots) with soil mix (topsoil and peat-Vet, 50/50). The pots were in a tray filled with half an inch of water. 15-16-17 (N-K-P) was used to fertilize the plants (250 ppm) once a week or according to the plants' needs by their appearances. The plants remained in 14 hours light (minimum) 6 a.m.–8 p.m. high light intensity, temperature 85°–90°/70° F. day/night.

The plants formed rice grains and the rice grains were harvested. These harvested seeds can have the starch extracted and analyzed for the presence of the ligated amino acids C, V, A, E, L, S, R, E [SEQ ID NO:27] in the starch within the seed.

Example Seven

Figure 6:
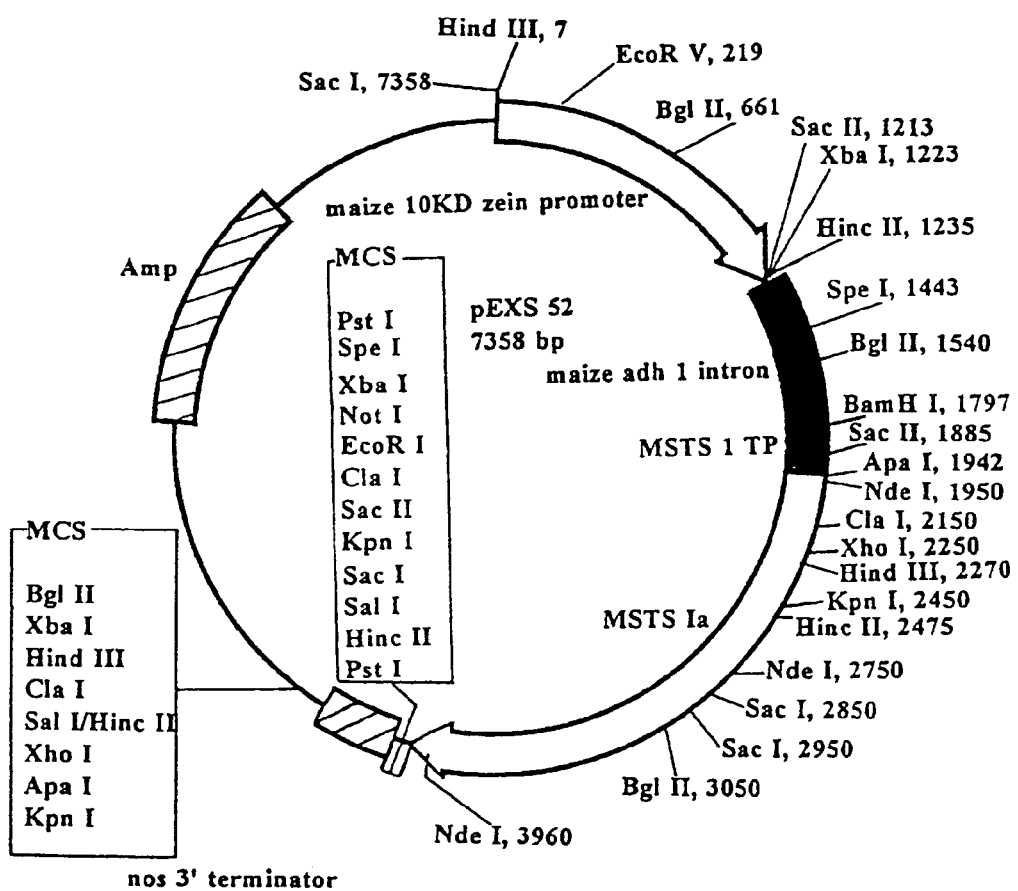
FIG. 6 shows the plasmid pEXS52.
Figure 7A:
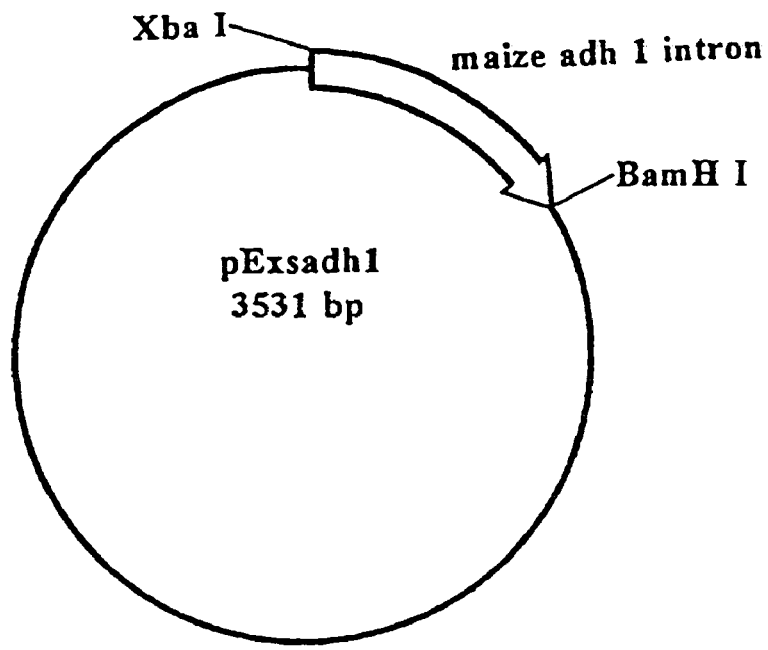
FIG. 7A–7F shows the six introductory plasmids used to form pEXS51 and pEX560.
Figure 7B:
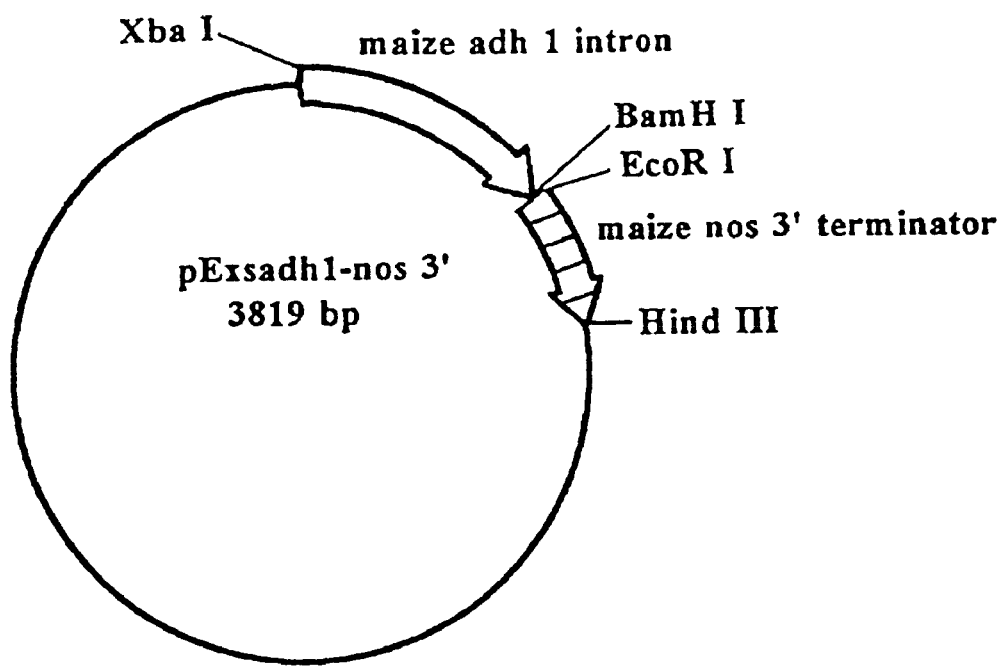
Figure 7C:
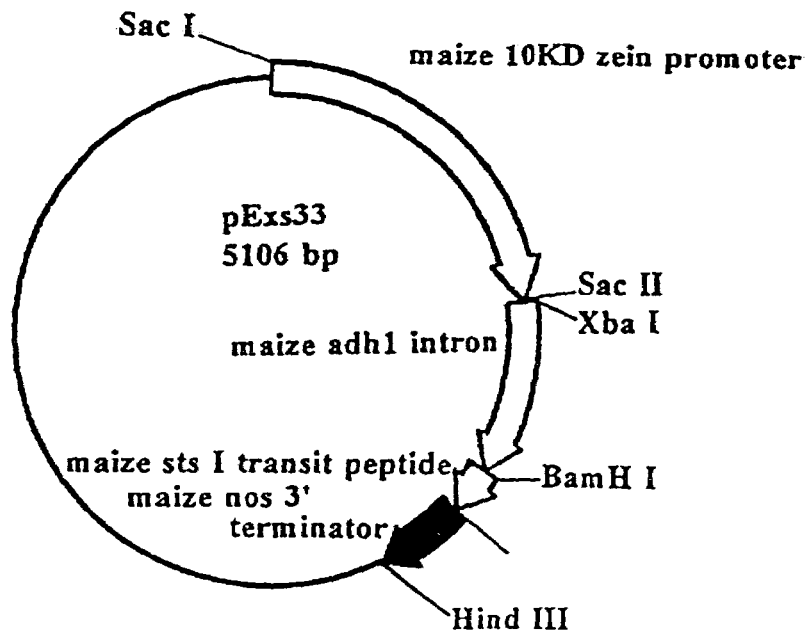
Figure 7D:
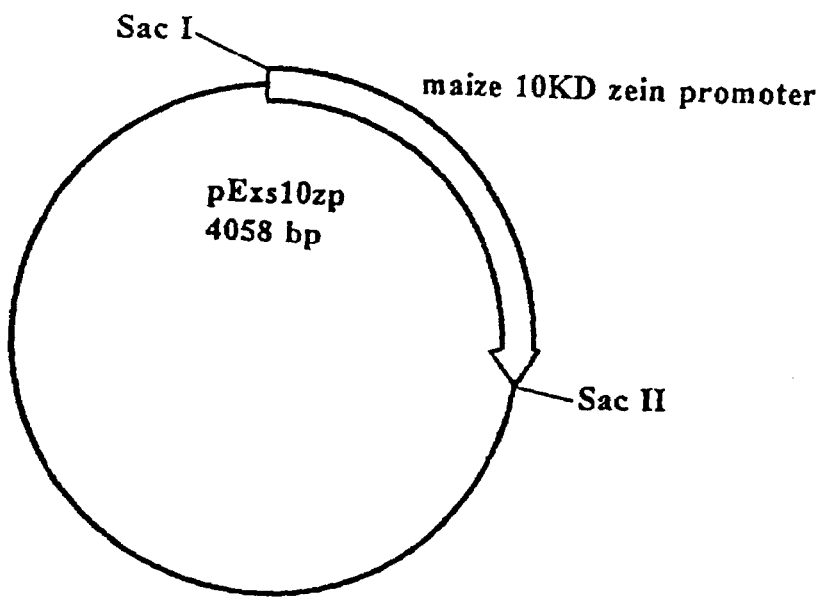
Figure 7E:
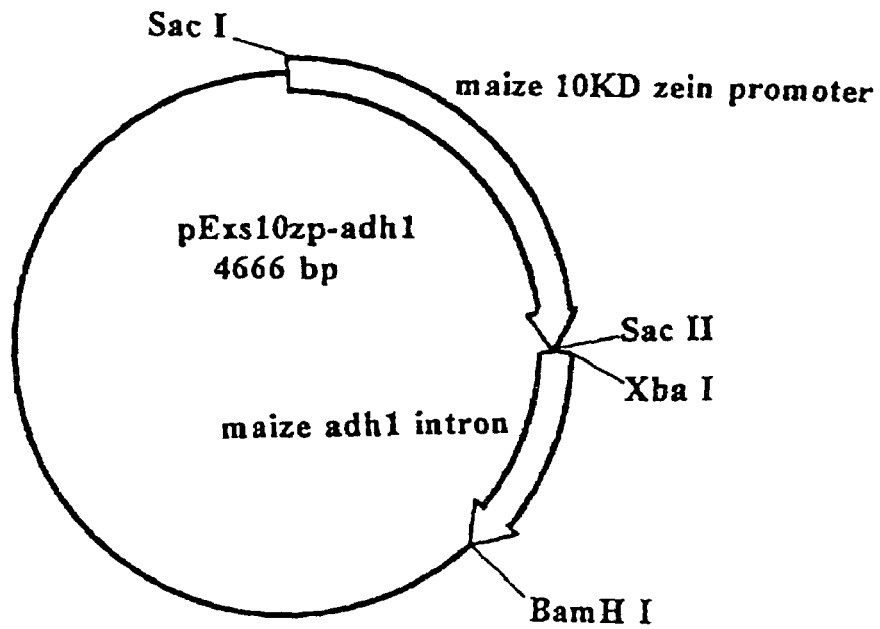
Figure 7F:
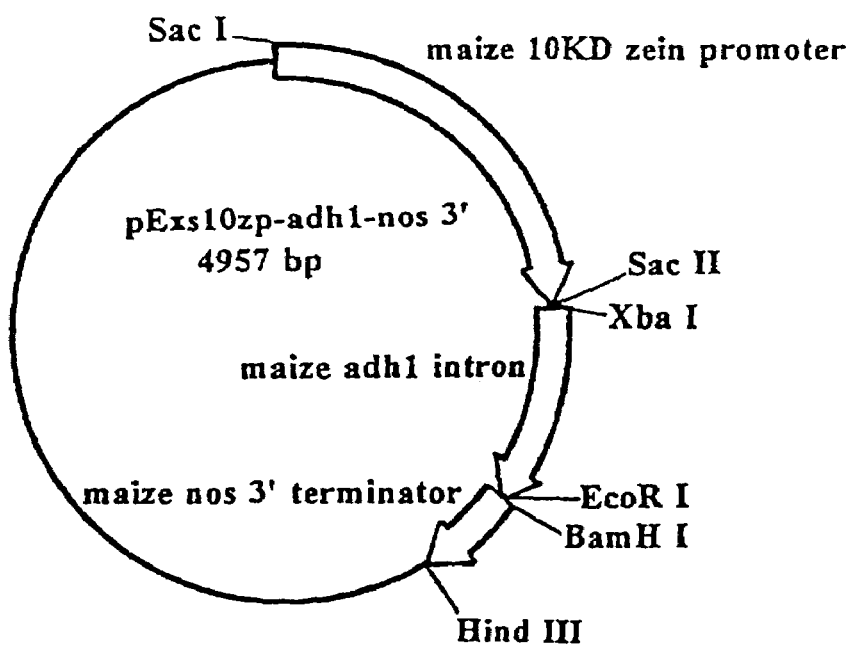

SER Vector for Plants:

The plasmid shown in FIG. 6 is adapted for use in monocots, i.e., maize. Plasmid pEXS52 (FIG. 6) has a promoter, a transit peptide (from maize), and a ligated gene fragment (TGC GTC GCG GAG CTG AGC AGG GAG) [SEQ ID NO:26] which encodes the amino acid sequence C V A E L S R E [SEQ ID NO:27].

This gene fragment naturally occurs close to the N-terminal end of the maize soluble starch synthase (MSTSI) gene. As is shown in TABLE 8, at about amino acid 292 the SER from the starch synthase begins. This vector is preferably transformed into a maize host. The transit peptide is adapted for maize so this is the preferred host. Clearly the transit peptide and the promoter, if necessary, can be altered to be appropriate for the host plant desired. After transformation by "whiskers" technology (U.S. Pat. Nos. 5,302,523 and 5,464,765), the transformed host cells are regenerated by methods known in the art, the transformant is pollinated, and the resultant kernels can be collected and analyzed for the presence of the peptide in the starch and the starch granule.

The following preferred genes can be employed in maize to improve feeds: phytase gene, the somototrophin gene, the following chained amino acids: AUG AUG AUG AUG AUG AUG AUG AUG [SEQ ID NO:28]; and/or, AAG AAG AAG AAG AAG AAG AAG AAG AAG AAG {SEQ ID NO:29]; and/or AAA AAA AAA AAA AAA AAA [ID NO:30]; or a combination of the codons encoding the lysine amino acid in a chain or a combination of the codons encoding both lysine and the methionine codon or any combination of two or three of these amino acids. The length of the chains should not be unduly long but the length of the chain does not appear to be critical. Thus the amino acids will be encapsulated within the starch granule or bound within the starch formed in the starch-bearing portion of the plant host.

This plasmid may be transformed into other cereals such as rice, wheat, barley, oats, sorghum, or millet with little to no modification of the plasmid. The promoter may be the waxy gene promoter whose sequence has been published, or other zein promoters known to the art.

Additionally these plasmids, without undue experimentation, may be transformed into dicots such as potatoes, sweet potato, taro, yam, lotus cassava, peanuts, peas, soybean, beans, or chickpeas. The promoter may be selected to target the starch-storage area of particular dicots or tubers, for example the patatin promoter may be used for potato tubers.

Various methods of transforming monocots and dicots are known in the industry and the method of transforming the genes is not critical to the present invention. The plasmid can be introduced into *Agrobacterium tumefaciens* by the freeze-thaw method of An et al. (1988) Binary Vectors, in Plant Molecular Biology Manual A3, S. B. Gelvin and R. A. Schilperoot, eds. (Dordrecht, The Netherlands: Kluwer Academic Publishers), pp. 1–19. Preparation of *Agrobacterium* inoculum carrying the construct and inoculation of plant material, regeneration of shoots, and rooting of shoots are described in Edwards et al., "Biochemical and molecular characterization of a novel starch synthase from potatoes," Plant J. 8, 283–294 (1995).

A number of encapsulating regions are present in a number of different genes. Although it is preferred that the protein be encapsulated within the starch granule (granule encapsulation), encapsulation within non-granule starch is also encompassed within the scope of the present invention in the term "encapsulation." The following types of genes are useful for this purpose.

Use of Starch-Encapsulating Regions of Glycogen Synthase:

*E. coli* glycogen synthase is not a large protein: the structural gene is 1431 base pairs in length, specifying a protein of 477 amino acids with an estimated molecular weight of 49,000. It is known that problems of codon usage can occur with bacterial genes inserted into plant genomes but this is generally not so great with *E. coli* genes as with those from other bacteria such as those from *Bacillus*. Glycogen synthase from *E. coli* has a codon usage profile much in common with maize genes but it is preferred to alter, by known procedures, the sequence at the translation start point to be more compatible with a plant consensus sequence:

```
glgA G A T A A T G C A G          [SEQ ID NO:31]
cons A A C A A T G G C T          [SEQ ID NO:32]
```

Use of Starch-Encapsulating Regions of Soluble Starch Synthase:

cDNA clones of plant-soluble starch synthases are described in the background section above and can be used in the present invention. The genes for any such SSTS protein may be used in constructs according to this invention.

Use of Starch-Encapsulating Regions of Branching Enzyme:

cDNA clones of plant, bacterial and animal branching enzymes are described in the background section above can be used in the present invention. Branching enzyme [1,4Dglucan: 1,4Dglucan 6D(1,4Dglucano) transferase (E.C. 2.4.1.18)] converts amylose to amylopectin, (a segment of a 1,4Dglucan chain is transferred to a primary hydroxyl group in a similar glucan chain) sometimes called Q-enzyme.

The sequence of maize branching enzyme I was investigated by Baba et al. (1991) BBRC, 181:87–94. Starch branching enzyme II from maize endosperm was investigated by Fisher et al. (1993) Plant Physiol, 102:1045–1046. The BE gene construct may require the presence of an amyloplast transit peptide to ensure its correct localization in the amyloplast. The genes for any such branching enzyme of GBSTS protein may be used in constructs according to this invention.

Use of Starch-Binding Domains of Granule-Bound Starch Synthase:

The use of cDNA clones of plant granule-bound starch synthases are described in Shure et al. (1983) Cell 35:225–233, and Visser et al. (1989) Plant Sci. 64(2): 185–192. Visser et al. have also described the inhibition of the expression of the gene for granule-bound starch synthase in potato by antisense constructs (1991) Mol. Gen. Genetic 225(2):289–296; (1994) The Plant Cell 6:43–52.) Shimada et al. show antisense in rice (1993) Theor. Appl. Genet. 86:665–672. Van der Leij et al. show restoration of amylose synthesis in low-amylose potato following transformation with the wild-type waxy potato gene (1991) Theor. Appl. Genet. 82:289–295.

The amino acid sequences and nucleotide sequences of granule starch synthases from, for example, maize, rice, wheat, potato, cassava, peas or barley are well known. The genes for any such GBSTS protein may be used in constructs according to this invention.

Construction of Plant Transformation Vectors:

Plant transformation vectors for use in the method of the invention may be constructed using standard techniques Use of Transit Peptide Sequences:

Some gene constructs require the presence of an amyloplast transit peptide to ensure correct localization in the amyloplast. It is believed that chloroplast transit peptides have similar sequences (Heijne et al. describe a database of chloroplast transit peptides in (1991) Plant Mol. Biol. Reporter, 9(2): 104–126). Other transit peptides useful in this invention are those of ADPG pyrophosphorylase (1991) Plant Mol. Biol. Reporter, 9:104–126), small subunit RUBISCO, acetolactate synthase, glyceraldehyde3Pdehydrogenase and nitrite reductase.

The consensus sequence of the transit peptide of small subunit RUBISCO from many genotypes has the sequence:

MASSMLSSAAVATRTNPAQASMVAPFTGLKSAAFP   [SEQ ID NO:33]

VSRKQNLDITSIASNGGRVQC

The corn small subunit RUBISCO has the sequence: MAPTVMMASSATATRTNPAQAS AVAFQGLKSTASLP-VARRSSR SLGNVASNGGRIRC [SEQ ID NO:34]

The transit peptide of leaf glyceraldehyde3Pdehydrogenase from corn has the sequence:

MAQILAPSTQWQMRITKTSPCATPITSKMWSSLVM   [SEQ ID NO:35]

KQTKKVAHSAKFRVMAVNSENGT

The transit peptide sequence of corn endosperm-bound starch synthase has the sequence:

MAALATSQLVATRAGHGVPDASTFRRGAAQGLRGA   [SEQ ID NO:36]

RASAAADTLSMRTSARAAPRHQQQARRGGRFPFPS

LVVC

The transit peptide sequence of corn endosperm soluble starch synthase has the sequence:

MATPSAVGAACLLLARXAWPAAVGDRARPRRLQRV   [SEQ ID NO:37]

LRRR

Engineering New Amino Acids or Peptides into Starch-Encapsulating Proteins:

The starch-binding proteins used in this invention may be modified by methods known to those skilled in the art to incorporate new amino acid combinations. For example, sequences of starch-binding proteins may be modified to express higher-than-normal levels of lysine, methionine or tryptophan. Such levels can be usefully elevated above natural levels and such proteins provide nutritional enhancement in crops such as cereals.

In addition to altering amino acid balance, it is possible to engineer the starch-binding proteins so that valuable peptides can be incorporated into the starch-binding protein. Attaching the payload polypeptide to the starch-binding protein at the N-terminal end of the protein provides a known means of adding peptide fragments and still maintaining starch-binding capacity. Further improvements can be made by incorporating specific protease cleavage sites into the site of attachment of the payload polypeptide to the starch-encapsulating region. It is well known to those skilled in the art that proteases have preferred specificities for different amino-acid linkages. Such specificities can be used to provide a vehicle for delivery of valuable peptides to different regions of the digestive tract of animals and man.

In yet another embodiment of this invention, the payload polypeptide can be released following purification and processing of the starch granules. Using amylolysis and/or gelatinization procedures it is known that the proteins bound to the starch granule can be released or become available for proteolysis. Thus recovery of commercial quantities of proteins and peptides from the starch granule matrix becomes possible.

In yet another embodiment of the invention it is possible to process the starch granules in a variety of different ways in order to provide a means of altering the digestibility of the starch. Using this methodology it is possible to change the bioavailablility of the proteins, peptides or amino acids entrapped within the starch granules.

Although the foregoing invention has been described in detail by way of illustration and example for purposes of clarity and understanding, it will be readily apparent to those of ordinary skill in the art in light of the teachings of this invention that certain changes and modifications may be made thereto without departing from the spirit or scope of the appended claims.

```
                           SEQUENCE LISTING (1) GENERAL INFORMATION:

(iii) NUMBER OF SEQUENCES: 37

(2) INFORMATION FOR SEQ ID NO: 1:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO: 1:

GACTAGTCAT ATGGTGAGCA AGGGCGAGGA G                                    31

(2) INFORMATION FOR SEQ ID NO: 2:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO: 2:

CTAGATCTTC ATATGCTTGT ACAGCTCGTC CATGCC                               36

(2) INFORMATION FOR SEQ ID NO: 3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO: 3:

CTAGATCTTG GCCATGGCCT TGTACAGCTC GTCCATGCC                            39

(2) INFORMATION FOR SEQ ID NO: 4:

(i) SEQUENCE CHARACTERISTICS:
        (A) LENGTH: 4800 base pairs
        (B) TYPE: nucleic acid
        (C) STRANDEDNESS: double
        (D) TOPOLOGY: Not Relevant
```

(ii) MOLECULE TYPE: DNA (genomic)

(iii) HYPOTHETICAL: NO (vi) ORIGINAL SOURCE:
             (A) ORGANISM: Zea mays (ix) FEATURE:
             (A) NAME/KEY: CDS
             (B) LOCATION: join(1449..1553, 1685..1765, 1860..1958, 2055
                 ..2144, 2226..2289, 2413..2513, 2651..2760, 2858
                 ..3101, 3212..3394, 3490..3681, 3793..3879, 3977
                 ..4105, 4227..4343)

(xi) SEQUENCE DESCRIPTION: SEQ ID NO: 4:

```
CAGCGACCTA TTACACAGCC CGCTCGGGCC CGCGACGTCG GGACACATCT TCTTCCCCCT       60

TTTGGTGAAG CTCTGCTCGC AGCTGTCCGG CTCCTTGGAC GTTCGTGTGG CAGATTCATC      120

TGTTGTCTCG TCTCCTGTGC TTCCTGGGTA GCTTGTGTAG TGGAGCTGAC ATGGTCTGAG      180

CAGGCTTAAA ATTTGCTCGT AGACGAGGAG TACCAGCACA GCACGTTGCG GATTTCTCTG      240

CCTGTGAAGT GCAACGTCTA GGATTGTCAC ACGCCTTGGT CGCGTCGCGT CGCGTCGCGT      300

CGATGCGGTG GTGAGCAGAG CAGCAACAGC TGGGCGGCCC AACGTTGGCT TCCGTGTCTT      360

CGTCGTACGT ACGCGCGCGC CGGGGACACG CAGCAGAGAG CGGAGAGCGA GCCGTGCACG      420

GGGAGGTGGT GTGGAAGTGG AGCCGCGCGC CCGGCCGCCC GCGCCCGGTG GGCAACCCAA      480

AAGTACCCAC GACAAGCGAA GGCGCCAAAG CGATCCAAGC TCCGGAACGC AACAGCATGC      540

GTCGCGTCGG AGAGCCAGCC ACAAGCAGCC GAGAACCGAA CCGGTGGGCG ACGCGTCATG      600

GGACGGACGC GGGCGACGCT TCCAAACGGG CCACGTACGC CGGCGTGTGC GTGCGTGCAG      660

ACGACAAGCC AAGGCGAGGC AGCCCCCGAT CGGGAAAGCG TTTTGGGCGC GAGCGCTGGC      720

GTGCGGGTCA GTCGCTGGTG CGCAGTGCCG GGGGAACGG GTATCGTGGG GGGCGCGGGC      780

GGAGGAGAGC GTGGCGAGGG CCGAGAGCAG CGCGCGGCCG GGTCACGCAA CGCGCCCCAC      840

GTACTGCCCT CCCCCTCCGC GCGCGCTAGA AATACCGAGG CCTGGACCGG GGGGGGGCCC      900

CGTCACATCC ATCCATCGAC CGATCGATCG CCACAGCCAA CACCACCCGC CGAGGCGACG      960

CGACAGCCGC CAGGAGGAAG GAATAAACTC ACTGCCAGCC AGTGAAGGGG GAGAAGTGTA     1020

CTGCTCCGTC GACCAGTGCG CGCACCGCCC GGCAGGGCTG CTCATCTCGT CGACGACCAG     1080

GTTCTGTTCC GTTCCGATCC GATCCGATCC TGTCCTTGAG TTTCGTCCAG ATCCTGGCGC     1140

GTATCTGCGT GTTTGATGAT CCAGGTTCTT CGAACCTAAA TCTGTCCGTG CACACGTCTT     1200

TTCTCTCTCT CCTACGCAGT GGATTAATCG GCATGGCGGC TCTGGCCACG TCGCAGCTCG     1260

TCGCAACGCG CGCCGGCCTG GGCGTCCCGG ACGCGTCCAC GTTCCGCCGC GGCGCCGCGC     1320

AGGGCCTGAG GGGGGCCCGG GCGTCGGCGG CGGCGGACAC GCTCAGCATG CGGACCAGCG     1380

CGCGCGCGGC GCCCAGGCAC CAGCAGCAGG CGCGCCGCGG GGGCAGGTTC CCGTCGCTCG     1440

TCGTGTGC GCC AGC GCC GGC ATG AAC GTC GTC TTC GTC GGC GCC GAG ATG     1490
         Ala Ser Ala Gly Met Asn Val Val Phe Val Gly Ala Glu Met
           1               5                  10

GCG CCG TGG AGC AAG ACC GGC GGC CTC GGC GAC GTC CTC GGC GGC CTG     1538
Ala Pro Trp Ser Lys Thr Gly Gly Leu Gly Asp Val Leu Gly Gly Leu
 15                 20                  25                  30

CCG CCG GCC ATG GCC GTAAGCGCGC GCACCGAGAC ATGCATCCGT TGGATCGCGT     1593
Pro Pro Ala Met Ala
                35

CTTCTTCGTG CTCCTTGCCG CGTGCATGATG CATGTGTTTC CTCCTGGCTT GTGTTCGTGT     1653

ATGTGACGTG TTTGTTCGGG CATGCATGCA G GCG AAC GGG CAC CGT GTC ATG        1705
```

-continued

```
                            Ala Asn Gly His Arg Val Met
                                            40
GTC GTC TCT CCC CGC TAC GAC CAG TAC AAG GAC GCC TGG GAC ACC AGC      1753
Val Val Ser Pro Arg Tyr Asp Gln Tyr Lys Asp Ala Trp Asp Thr Ser
        45                  50                  55

GTC GTG TCC GAG GTACGGCCAC CGAGACCAGA TTCAGATCAC AGTCACACAC          1805
Val Val Ser Glu
        60

ACCGTCATAT GAACCTTTCT CTGCTCTGAT GCCTGCAACT GCAAATGCAT GCAG ATC      1862
                                                            Ile

AAG ATG GGA GAC GGG TAC GAG ACG GTC AGG TTC TTC CAC TGC TAC AAG      1910
Lys Met Gly Asp Gly Tyr Glu Thr Val Arg Phe Phe His Cys Tyr Lys
        65                  70                  75

CGC GGA GTG GAC CGC GTG TTC GTT GAC CAC CCA CTG TTC CTG GAG AGG      1958
Arg Gly Val Asp Arg Val Phe Val Asp His Pro Leu Phe Leu Glu Arg
80                  85                  90                  95

GTGAGACGAG ATCTGATCAC TCGATACGCA ATTACCACCC CATTGTAAGC AGTTACAGTG    2018

AGCTTTTTTT CCCCCCGGCC TGGTCGCTGG TTTCAG GTT TGG GGA AAG ACC GAG      2072
                                     Val Trp Gly Lys Thr Glu
                                                         100

GAG AAG ATC TAC GGG CCT GTC GCT GGA ACG GAC TAC AGG GAC AAC CAG      2120
Glu Lys Ile Tyr Gly Pro Val Ala Gly Thr Asp Tyr Arg Asp Asn Gln
            105                 110                 115

CTG CGG TTC AGC CTG CTA TGC CAG GTCAGGATGG CTTGGTACTA CAACTTCATA     2174
Leu Arg Phe Ser Leu Leu Cys Gln
            120             125

TCATCTGTAT GCAGCAGTAT ACACTGATGA GAAATGCATG CTGTTCTGCA G GCA GCA     2231
                                                        Ala Ala

CTT GAA GCT CCA AGG ATC CTG AGC CTC AAC AAC AAC CCA TAC TTC TCC      2279
Leu Glu Ala Pro Arg Ile Leu Ser Leu Asn Asn Asn Pro Tyr Phe Ser
            130                 135                 140

GGA CCA TAC G GTAAGAGTTG CAGTCTTCGT ATATATATCT GTTGAGCTCG            2329
Gly Pro Tyr
145

AGAATCTTCA CAGGAAGCGG CCCATCAGAC GGACTGTCAT TTTACACTGA CTACTGCTGC    2389

TGCTCTTCGT CCATCCATAC AAG  GG GAG GAC GTC GTG TTC GTC TGC AAC       2438
                             Gly Glu Asp Val Val Phe Val Cys Asn
                                         150                 155

GAC TGG CAC ACC GGC CCT CTC TCG TGC TAC CTC AAG AGC AAC TAC CAG      2486
Asp Trp His Thr Gly Pro Leu Ser Cys Tyr Leu Lys Ser Asn Tyr Gln
            160                 165                 170

TCC CAC GGC ATC TAC AGG GAC GCA AAG GTTGCCTTCT CTGAACTGAA            2533
Ser His Gly Ile Tyr Arg Asp Ala Lys
            175             180

CAACGCCGTT TTCGTTCTCC ATGCTCGTAT ATACCTCGTC TGGTAGTGGT GGTGCTTCTC    2593

TGAGAAACTA ACTGAAACTG ACTGCATGTC TGTCTGACCA TCTTCACGTA CTACCAG       2650

ACC GCT TTC TGC ATC CAC AAC ATC TCC TAC CAG GGC CGG TTC GCC TTC      2698
Thr Ala Phe Cys Ile His Asn Ile Ser Tyr Gln Gly Arg Phe Ala Phe
            185                 190                 195

TCC GAC TAC CCG GAG CTG AAC CTC CCG GAG AGA TTC AAG TCG TCC TTC      2746
Ser Asp Tyr Pro Glu Leu Asn Leu Pro Glu Arg Phe Lys Ser Ser Phe
            200                 205                 210

GAT TTC ATC GAC GG  GTCTGTTTTC CTGCGTGCAT GTGAACATTC ATGAATGGTA      2800
Asp Phe Ile Asp Gly
            215

ACCCACAACT GTTCGCGTCC TGCTGGTTCA TTATCTGACC TGATTGCATT ATTGCAG C     2858
```

-continued

| | |
|---|---|
| TAC GAG AAG CCC GTG AAA GGC CGG AAG ATC AAC TGG ATG AAG GCC GGG<br>Tyr Glu Lys Pro Val Glu Gly Arg Lys Ile Asn Trp Met Lys Ala Gly<br>220               225                 230 | 2906 |
| ATC CTC GAG GCC GAC AGG GTC CTC ACC GTC AGC CCC TAC TAC GCC GAG<br>Ile Leu Glu Ala Asp Arg Val Leu Thr Val Ser Pro Tyr Tyr Ala Glu<br>235               240                 245 | 2954 |
| GAG CTC ATC TCC GGC ATC GCC AGG GGC TGC GAG CTC GAC AAC ATC ATG<br>Glu Leu Ile Ser Gly Ile Ala Arg Gly Cys Glu Leu Asp Asn Ile Met<br>250               255                 260               265 | 3002 |
| CGC CTC ACC GGC ATC ACC GGC ATC GTC AAC GGC ATG GAC GTC AGC GAG<br>Arg Leu Thr Gly Ile Thr Gly Ile Val Asn Gly Met Asp Val Ser Glu<br>270               275                 280 | 3050 |
| TGG GAC CCC AGC AGG GAC AAG TAC ATC GCC GTG AAG TAC GAC GTG TCG<br>Trp Asp Pro Ser Arg Asp Lys Tyr Ile Ala Val Lys Tyr Asp Val Ser<br>285               290                 295 | 3098 |
| ACG GTGAGCTGGC TAGCTCTGAT TCTGCTGCCT GGTCCTCCTG CTCATCATGC<br>Thr | 3151 |
| TGGTTCGGTA CTGACGCGGC AAGTGTACGT ACGTGCGTGC GACGGTGGTG TCCGGTTCAG | 3211 |
| GCC GTG GAG GCC AAG GCG CTG AAC AAG GAG GCG CTG CAG GCG GAG GTC<br>Ala Val Glu Ala Lys Ala Leu Asn Lys Glu Ala Leu Gln Ala Glu Val<br>300               305                 310 | 3259 |
| GGG CTC CCG GTG GAC CGG AAC ATC CCG CTG GTG GCG TTC ATC GGC AGG<br>Gly Leu Pro Val Asp Arg Asn Ile Pro Leu Val Ala Phe Ile Gly Arg<br>315               320                 325               330 | 3307 |
| CTG GAA GAG CAG AAG GGC CCC GAC GTC ATG GCG GCC GCC ATC CCG CAG<br>Leu Glu Glu Gln Lys Gly Pro Asp Val Met Ala Ala Ala Ile Pro Gln<br>335               340                 345 | 3355 |
| CTC ATG GAG ATG GTG GAG GAC GTG CAG ATC GTT CTG CTG GTACGTGTGC<br>Leu Met Glu Met Val Glu Asp Val Gln Ile Val Leu Leu<br>350               355 | 3404 |
| GCCGGCCGCC ACCCGGCTAC TACATGCGTG TATCGTTCGT TCTACTGGAA CATGCGTGTG | 3464 |
| AGCAACGCGA TGGATAATGC TGCAG GGC ACG GGC AAG AAG AAG TTC GAG CGC<br>                                             Gly Thr Gly Lys Lys Lys Phe Glu Arg<br>                                             360                 365 | 3516 |
| ATG CTC ATG AGC GCC GAG GAG AAG TTC CCA GGC AAG GTG CGC GCC GTG<br>Met Leu Met Ser Ala Glu Glu Lys Phe Pro Gly Lys Val Arg Ala Val<br>370               375                 380 | 3564 |
| GTC AAG TTC AAC GCG GCG CTG GCG CAC CAC ATC ATG GCC GGC GCC GAC<br>Val Lys Phe Asn Ala Ala Leu Ala His His Ile Met Ala Gly Ala Asp<br>385               390                 395               400 | 3612 |
| GTG CTC GCC GTC ACC AGC CGC TTC GAG CCC TGC GGC CTC ATC CAG CTG<br>Val Leu Ala Val Thr Ser Arg Phe Glu Pro Cys Gly Leu Ile Gln Leu<br>               405                 410               415 | 3660 |
| CAG GGG ATG CGA TAC GGA ACG GTACGAGAGA AAAAAAAAT CCTGAATCCT<br>Gln Gly Met Arg Tyr Gly Thr<br>               420 | 3711 |
| GACGAGAGGG ACAGAGACAG ATTATGAATG CTTCATCGAT TTGAATTGAT TGATCGATGT | 3771 |
| CTCCCGCTGC GACTCTTGCA G CCC TGC GCC TGC GCG TCC ACC GGT GGA CTC<br>                                 Pro Cys Ala Cys Ala Ser Thr Gly Gly Leu<br>                                 425                           430 | 3822 |
| GTC GAC ACC ATC ATC GAA GGC AAG ACC GGG TTC CAC ATG GGC CGC CTC<br>Val Asp Thr Ile Ile Glu Gly Lys Thr Gly Phe His Met Gly Arg Leu<br>435               440                 445 | 3870 |
| AGC GTC GAC GTAAGCCTAG CTCTGCCATG TTCTTTCTTC TTTCTTTCTG<br>Ser Val Asp<br>450 | 3919 |
| TATGTATGTA TGAATCAGCA CCGCCGTTCT TGTTTCGTCG TCGTCCTCTC TTCCCAG | 3976 |

```
TGT AAC GTC GTG GAG CCG GCG GAC GTC AAG AAG GTG GCC ACC ACA TTG      4024
Cys Asn Val Val Glu Pro Ala Asp Val Lys Lys Val Ala Thr Thr Leu
        455                 460                 465

CAG CGC GCC ATC AAG GTG GTC GGC ACG CCG GCG TAC GAG GAG ATG GTG      4072
Gln Arg Ala Ile Lys Val Val Gly Thr Pro Ala Tyr Glu Glu Met Val
    470                 475                 480

AGG AAC TGC ATG ATC CAG GAT CTC TCC TGG AAG GTACGTACGC CCGCCCCGCC    4125
Arg Asn Cys Met Ile Gln Asp Leu Ser Trp Lys
485                 490                 495

CCGCCCCGCC AGAGCAGAGC GCCAAGATCG ACCGATCGAC CGACCACACG TACGCGCCTC    4185

GCTCCTGTCG CTGACCGTGG TTTAATTTGC GAAATGCGCA G GGC CCT GCC AAG        4238
                                             Gly Pro Ala Lys

AAC TGG GAG AAC GTG CTG CTC AGC CTC GGG GTC GCC GGC GGC GAG CCA      4286
Asn Trp Glu Asn Val Leu Leu Ser Leu Gly Val Ala Gly Gly Glu Pro
500                 505                 510                 515

GGG GTC GAA GGC GAG GAG ATC GCG CCG CTC GCC AAG GAG AAC GTG GCC      4334
Gly Val Glu Gly Glu Glu Ile Ala Pro Leu Ala Lys Glu Asn Val Ala
                520                 525                 530

GCG CCC TGA AGAGTTCGGC CTGCAGGGCC CCTGATCTCG CGCGTGGTGC              4383
Ala Pro *

AAAGATGTTG GGACATCTTC TTATATATGC TGTTTCGTTT ATGTGATATG GACAAGTATG    4443

TGTAGCTGCT TGCTTGTGCT AGTGTAATGT AGTGTAGTGG TGGCCAGTGG CACAACCTAA    4503

TAAGCGCATG AACTAATTGC TTGCGTGTGT AGTTAAGTAC CGATCGGTAA TTTTATATTG    4563

CGAGTAAATA AATGGACCTG TAGTGGTGGA GTAAATAATC CCTGCTGTTC GGTGTTCTTA    4623

TCGCTCCTCG TATAGATATT ATATAGAGTA CATTTTCTC TCTCTGAATC CTACGTTTGT     4683

GAAATTTCTA TATCATTACT GTAAAATTTC TGCGTTCCAA AAGAGACCAT AGCCTATCTT    4743

TGGCCCTGTT TGTTTCGGCT TCTGGCAGCT TCTGGCCACC AAAAGCTGCT GCGGACT       4800

(2) INFORMATION FOR SEQ ID NO: 5:

(i) SEQUENCE CHARACTERISTICS:
        (A) LENGTH: 533 amino acids
        (B) TYPE: amino acid
        (D) TOPOLOGY: linear (ii) MOLECULE TYPE: protein (xi) SEQUENCE DESCRIPTION: SEQ ID NO: 5:

Ala Ser Ala Gly Met Asn Val Val Phe Val Gly Ala Glu Met Ala Pro
 1                5                  10                  15

Trp Ser Lys Thr Gly Gly Leu Gly Asp Val Leu Gly Gly Leu Pro Pro
            20                  25                  30

Ala Met Ala Ala Asn Gly His Arg Val Met Val Val Ser Pro Arg Tyr
        35                  40                  45

Asp Gln Tyr Lys Asp Ala Trp Asp Thr Ser Val Ser Glu Ile Lys
    50                  55                  60

Met Gly Asp Gly Tyr Glu Thr Val Arg Phe Phe His Cys Tyr Lys Arg
 65                  70                  75                  80

Gly Val Asp Arg Val Phe Val Asp His Pro Leu Phe Leu Glu Arg Val
                    85                  90                  95

Trp Gly Lys Thr Glu Glu Lys Ile Tyr Gly Pro Val Ala Gly Thr Asp
                100                 105                 110

Tyr Arg Asp Asn Gln Leu Arg Phe Ser Leu Leu Cys Gln Ala Ala Leu
            115                 120                 125

Glu Ala Pro Arg Ile Leu Ser Leu Asn Asn Asn Pro Tyr Phe Ser Gly
```

```
                130                 135                 140
Pro Tyr Gly Glu Asp Val Val Phe Val Cys Asn Asp Trp His Thr Gly
145                 150                 155                 160

Pro Leu Ser Cys Tyr Leu Lys Ser Asn Tyr Gln Ser His Gly Ile Tyr
                165                 170                 175

Arg Asp Ala Lys Thr Ala Phe Cys Ile His Asn Ile Ser Tyr Gln Gly
                180                 185                 190

Arg Phe Ala Phe Ser Asp Tyr Pro Glu Leu Asn Leu Pro Glu Arg Phe
                195                 200                 205

Lys Ser Ser Phe Asp Phe Ile Asp Gly Tyr Glu Lys Pro Val Glu Gly
210                 215                 220

Arg Lys Ile Asn Trp Met Lys Ala Gly Ile Leu Glu Ala Asp Arg Val
225                 230                 235                 240

Leu Thr Val Ser Pro Tyr Tyr Ala Glu Glu Leu Ile Ser Gly Ile Ala
                245                 250                 255

Arg Gly Cys Glu Leu Asp Asn Ile Met Arg Leu Thr Gly Ile Thr Gly
                260                 265                 270

Ile Val Asn Gly Met Asp Val Ser Glu Trp Asp Pro Ser Arg Asp Lys
            275                 280                 285

Tyr Ile Ala Val Lys Tyr Asp Val Ser Thr Ala Val Glu Ala Lys Ala
            290                 295                 300

Leu Asn Lys Glu Ala Leu Gln Ala Glu Val Gly Leu Pro Val Asp Arg
305                 310                 315                 320

Asn Ile Pro Leu Val Ala Phe Ile Gly Arg Leu Glu Glu Gln Lys Gly
                325                 330                 335

Pro Asp Val Met Ala Ala Ala Ile Pro Gln Leu Met Glu Met Val Glu
                340                 345                 350

Asp Val Gln Ile Val Leu Leu Gly Thr Gly Lys Lys Lys Phe Glu Arg
                355                 360                 365

Met Leu Met Ser Ala Glu Glu Lys Phe Pro Gly Lys Val Arg Ala Val
            370                 375                 380

Val Lys Phe Asn Ala Ala Leu Ala His His Ile Met Ala Gly Ala Asp
385                 390                 395                 400

Val Leu Ala Val Thr Ser Arg Phe Glu Pro Cys Gly Leu Ile Gln Leu
                405                 410                 415

Gln Gly Met Arg Tyr Gly Thr Pro Cys Ala Cys Ala Ser Thr Gly Gly
                420                 425                 430

Leu Val Asp Thr Ile Ile Glu Gly Lys Thr Gly Phe His Met Gly Arg
                435                 440                 445

Leu Ser Val Asp Cys Asn Val Val Glu Pro Ala Asp Val Lys Lys Val
450                 455                 460

Ala Thr Thr Leu Gln Arg Ala Ile Lys Val Val Gly Thr Pro Ala Tyr
465                 470                 475                 480

Glu Glu Met Val Arg Asn Cys Met Ile Gln Asp Leu Ser Trp Lys Gly
                485                 490                 495

Pro Ala Lys Asn Trp Glu Asn Val Leu Leu Ser Leu Gly Val Ala Gly
                500                 505                 510

Gly Glu Pro Gly Val Glu Gly Glu Ile Ala Pro Leu Ala Lys Glu
            515                 520                 525

Asn Val Ala Ala Pro
            530
```

(2) INFORMATION FOR SEQ ID NO: 6:

-continued

```
    (i) SEQUENCE CHARACTERISTICS:
        (A) LENGTH: 2542 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (vi) ORIGINAL SOURCE:
        (A) ORGANISM: Oryza sativa (ix) FEATURE:
        (A) NAME/KEY: CDS
        (B) LOCATION: 453..2282

(xi) SEQUENCE DESCRIPTION: SEQ ID NO: 6:
```

| | |
|---|---|
| GAATTCAGTG TGAAGGAATA GATTCTCTTC AAAACAATTT AATCATTCAT CTGATCTGCT | 60 |
| CAAAGCTCTG TGCATCTCCG GGTGCAACGG CCAGGATATT TATTGTGCAG TAAAAAAATG | 120 |
| TCATATCCCC TAGCCACCCA AGAAACTGCT CCTTAAGTCC TTATAAGCAC ATATGGCATT | 180 |
| GTAATATATA TGTTTGAGTT TTAGCGACAA TTTTTTTAAA AACTTTTGGT CCTTTTTATG | 240 |
| AACGTTTTAA GTTTCACTGT CTTTTTTTTT CGAATTTTAA ATGTAGCTTC AAATTCTAAT | 300 |
| CCCCAATCCA AATTGTAATA AACTTCAATT CTCCTAATTA ACATCTTAAT TCATTTATTT | 360 |
| GAAAACCAGT TCAAATTCTT TTTAGGCTCA CCAAACCTTA AACAATTCAA TTCAGTGCAG | 420 |

```
AGATCTTCCA CAGCAACAGC TAGACAACCA CC ATG TCG GCT CTC ACC ACG TCC      473
                                  Met Ser Ala Leu Thr Thr Ser
                                  535                 540

CAG CTC GCC ACC TCG GCC ACC GGC TTC GGC ATC GCC GAC AGG TCG GCG      521
Gln Leu Ala Thr Ser Ala Thr Gly Phe Gly Ile Ala Asp Arg Ser Ala
        545                 550                 555

CCG TCG TCG CTG CTC CGC CAC GGG TTC CAG GGC CTC AAG CCC CGC AGC      569
Pro Ser Ser Leu Leu Arg His Gly Phe Gln Gly Leu Lys Pro Arg Ser
    560                 565                 570

CCC GCC GGC GGC GAC GCG ACG TCG CTC AGC GTG ACG ACC AGC GCG CGC      617
Pro Ala Gly Gly Asp Ala Thr Ser Leu Ser Val Thr Thr Ser Ala Arg
575                 580                 585

GCG ACG CCC AAG CAG CAG CGG TCG GTG CAG CGT GGC AGC CGG AGG TTC      665
Ala Thr Pro Lys Gln Gln Arg Ser Val Gln Arg Gly Ser Arg Arg Phe
590                 595                 600                 605

CCC TCC GTC GTC GTG TAC GCC ACC GGC GCC GGC ATG AAC GTC GTG TTC      713
Pro Ser Val Val Val Tyr Ala Thr Gly Ala Gly Met Asn Val Val Phe
                610                 615                 620

GTC GGC GCC GAG ATG GCC CCC TGG AGC AAG ACC GGC GGC CTC GGT GAC      761
Val Gly Ala Glu Met Ala Pro Trp Ser Lys Thr Gly Gly Leu Gly Asp
            625                 630                 635

GTC CTC GGT GGC CTC CCC CCT GCC ATG GCT GCG AAT GGC CAC AGG GTC      809
Val Leu Gly Gly Leu Pro Pro Ala Met Ala Ala Asn Gly His Arg Val
        640                 645                 650

ATG GTG ATC TCT CCT CGG TAC GAC CAG TAC AAG GAC GCT TGG GAT ACC      857
Met Val Ile Ser Pro Arg Tyr Asp Gln Tyr Lys Asp Ala Trp Asp Thr
    655                 660                 665

AGC GTT GTG GCT GAG ATC AAG GTT GCA GAC AGG TAC GAG AGG GTG AGG      905
Ser Val Val Ala Glu Ile Lys Val Ala Asp Arg Tyr Glu Arg Val Arg
670                 675                 680                 685

TTT TTC CAT TGC TAC AAG CGT GGA GTC GAC CGT GTG TTC ATC GAC CAT      953
Phe Phe His Cys Tyr Lys Arg Gly Val Asp Arg Val Phe Ile Asp His
                690                 695                 700

CCG TCA TTC CTG GAG AAG GTT TGG GGA AAG ACC GGT GAG AAG ATC TAC      1001
```

```
                    Pro Ser Phe Leu Glu Lys Val Trp Gly Lys Thr Gly Glu Lys Ile Tyr
                                705                 710                 715

GGA CCT GAC ACT GGA GTT GAT TAC AAA GAC AAC CAG ATG CGT TTC AGC                  1049
Gly Pro Asp Thr Gly Val Asp Tyr Lys Asp Asn Gln Met Arg Phe Ser
            720                 725                 730

CTT CTT TGC CAG GCA GCA CTC GAG GCT CCT AGG ATC CTA AAC CTC AAC                  1097
Leu Leu Cys Gln Ala Ala Leu Glu Ala Pro Arg Ile Leu Asn Leu Asn
        735                 740                 745

AAC AAC CCA TAC TTC AAA GGA ACT TAT GGT GAG GAT GTT GTG TTC GTC                  1145
Asn Asn Pro Tyr Phe Lys Gly Thr Tyr Gly Glu Asp Val Val Phe Val
750                 755                 760                 765

TGC AAC GAC TGG CAC ACT GGC CCA CTG GCG AGC TAC CTG AAG AAC AAC                  1193
Cys Asn Asp Trp His Thr Gly Pro Leu Ala Ser Tyr Leu Lys Asn Asn
                770                 775                 780

TAC CAG CCC AAT GGC ATC TAC AGG AAT GCA AAG GTT GCT TTC TGC ATC                  1241
Tyr Gln Pro Asn Gly Ile Tyr Arg Asn Ala Lys Val Ala Phe Cys Ile
            785                 790                 795

CAC AAC ATC TCC TAC CAG GGC CGT TTC GCT TTC GAG GAT TAC CCT GAG                  1289
His Asn Ile Ser Tyr Gln Gly Arg Phe Ala Phe Glu Asp Tyr Pro Glu
        800                 805                 810

CTG AAC CTC TCC GAG AGG TTC AGG TCA TCC TTC GAT TTC ATC GAC GGG                  1337
Leu Asn Leu Ser Glu Arg Phe Arg Ser Ser Phe Asp Phe Ile Asp Gly
    815                 820                 825

TAT GAC ACG CCG GTG GAG GGC AGG AAG ATC AAC TGG ATG AAG GCC GGA                  1385
Tyr Asp Thr Pro Val Glu Gly Arg Lys Ile Asn Trp Met Lys Ala Gly
830                 835                 840                 845

ATC CTG GAA GCC GAC AGG GTG CTC ACC GTG AGC CCG TAC TAC GCC GAG                  1433
Ile Leu Glu Ala Asp Arg Val Leu Thr Val Ser Pro Tyr Tyr Ala Glu
                850                 855                 860

GAG CTC ATC TCC GGC ATC GCC AGG GGA TGC GAG CTC GAC AAC ATC ATG                  1481
Glu Leu Ile Ser Gly Ile Ala Arg Gly Cys Glu Leu Asp Asn Ile Met
            865                 870                 875

CGG CTC ACC GGC ATC ACC GGC ATC GTC AAC GGC ATG GAC GTC AGC GAG                  1529
Arg Leu Thr Gly Ile Thr Gly Ile Val Asn Gly Met Asp Val Ser Glu
        880                 885                 890

TGG GAT CCT AGC AAG GAC AAG TAC ATC ACC GCC AAG TAC GAC GCA ACC                  1577
Trp Asp Pro Ser Lys Asp Lys Tyr Ile Thr Ala Lys Tyr Asp Ala Thr
    895                 900                 905

ACG GCA ATC GAG GCG AAG GCG CTG AAC AAG GAG GCG TTG CAG GCG GAG                  1625
Thr Ala Ile Glu Ala Lys Ala Leu Asn Lys Glu Ala Leu Gln Ala Glu
910                 915                 920                 925

GCG GGT CTT CCG GTC GAC AGG AAA ATC CCA CTG ATC GCG TTC ATC GGC                  1673
Ala Gly Leu Pro Val Asp Arg Lys Ile Pro Leu Ile Ala Phe Ile Gly
                930                 935                 940

AGG CTG GAG GAA CAG AAG GGC CCT GAC GTC ATG GCC GCC GCC ATC CCG                  1721
Arg Leu Glu Glu Gln Lys Gly Pro Asp Val Met Ala Ala Ala Ile Pro
            945                 950                 955

GAG CTC ATG CAG GAG GAC GTC CAG ATC GTT CTT CTG GGT ACT GGA AAG                  1769
Glu Leu Met Gln Glu Asp Val Gln Ile Val Leu Leu Gly Thr Gly Lys
        960                 965                 970

AAG AAG TTC GAG AAG CTG CTC AAG AGC ATG GAG GAG AAG TAT CCG GGC                  1817
Lys Lys Phe Glu Lys Leu Leu Lys Ser Met Glu Glu Lys Tyr Pro Gly
    975                 980                 985

AAG GTG AGG GCG GTG GTG AAG TTC AAC GCG CCG CTT GCT CAT CTC ATC                  1865
Lys Val Arg Ala Val Val Lys Phe Asn Ala Pro Leu Ala His Leu Ile
990                 995                 1000                1005

ATG GCC GGA GCC GAC GTG CTC GCC GTC CCC AGC CGC TTC GAG CCC TGT                  1913
Met Ala Gly Ala Asp Val Leu Ala Val Pro Ser Arg Phe Glu Pro Cys
                1010                1015                1020
```

-continued

```
GGA CTC ATC CAG CTG CAG GGG ATG AGA TAC GGA ACG CCC TGT GCT TGC    1961
Gly Leu Ile Gln Leu Gln Gly Met Arg Tyr Gly Thr Pro Cys Ala Cys
            1025                1030                1035

GCG TCC ACC GGT GGG CTC GTG GAC ACG GTC ATC GAA GGC AAG ACT GGT    2009
Ala Ser Thr Gly Gly Leu Val Asp Thr Val Ile Glu Gly Lys Thr Gly
        1040                1045                1050

TTC CAC ATG GGC CGT CTC AGC GTC GAC TGC AAG GTG GTG GAG CCA AGC    2057
Phe His Met Gly Arg Leu Ser Val Asp Cys Lys Val Val Glu Pro Ser
    1055                1060                1065

GAC GTG AAG AAG GTG GCG GCC ACC CTG AAG CGC GCC ATC AAG GTC GTC    2105
Asp Val Lys Lys Val Ala Ala Thr Leu Lys Arg Ala Ile Lys Val Val
1070                1075                1080                1085

GGC ACG CCG GCG TAC GAG GAG ATG GTC AGG AAC TGC ATG AAC CAG GAC    2153
Gly Thr Pro Ala Tyr Glu Glu Met Val Arg Asn Cys Met Asn Gln Asp
            1090                1095                1100

CTC TCC TGG AAG GGG CCT GCG AAG AAC TGG GAG AAT GTG CTC CTG GGC    2201
Leu Ser Trp Lys Gly Pro Ala Lys Asn Trp Glu Asn Val Leu Leu Gly
        1105                1110                1115

CTG GGC GTC GCC GGC AGC GCG CCG GGG ATC GAA GGC GAC GAG ATC GCG    2249
Leu Gly Val Ala Gly Ser Ala Pro Gly Ile Glu Gly Asp Glu Ile Ala
    1120                1125                1130

CCG CTC GCC AAG GAG AAC GTG GCT GCT CCT TGA AGAGCCTGAG ATCTACATAT  2302
Pro Leu Ala Lys Glu Asn Val Ala Ala Pro *
1135                1140

GGAGTGATTA ATTAATATAG CAGTATATGG ATGAGAGACG AATGAACCAG TGGTTTGTTT  2362

GTTGTAGTGA ATTTGTAGCT ATAGCCAATT ATATAGGCTA ATAAGTTTGA TGTTGTACTC  2422

TTCTGGGTGT GCTTAAGTAT CTTATCGGAC CCTGAATTTA TGTGTGTGGC TTATTGCCAA  2482

TAATATTAAG TAATAAGGGG TTTATTATAT TATTATATAT GTTATATTAT ACTAAAAAAA  2542
```

(2) INFORMATION FOR SEQ ID NO: 7:

(i) SEQUENCE CHARACTERISTICS:
        (A) LENGTH: 609 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Ser Ala Leu Thr Thr Ser Gln Leu Ala Thr Ser Ala Thr Gly Phe
 1               5                  10                  15

Gly Ile Ala Asp Arg Ser Ala Pro Ser Ser Leu Arg His Gly Phe
            20                  25                  30

Gln Gly Leu Lys Pro Arg Ser Pro Ala Gly Gly Asp Ala Thr Ser Leu
        35                  40                  45

Ser Val Thr Thr Ser Ala Arg Ala Thr Pro Lys Gln Gln Arg Ser Val
    50                  55                  60

Gln Arg Gly Ser Arg Arg Phe Pro Ser Val Val Tyr Ala Thr Gly
65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
            100                 105                 110

Ala Ala Asn Gly His Arg Val Met Val Ile Ser Pro Arg Tyr Asp Gln
        115                 120                 125

Tyr Lys Asp Ala Trp Asp Thr Ser Val Val Ala Glu Ile Lys Val Ala
    130                 135                 140
```

```
Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
                165                 170                 175

Lys Thr Gly Glu Lys Ile Tyr Gly Pro Asp Thr Gly Val Asp Tyr Lys
            180                 185                 190

Asp Asn Gln Met Arg Phe Ser Leu Leu Cys Gln Ala Ala Leu Glu Ala
        195                 200                 205

Pro Arg Ile Leu Asn Leu Asn Asn Pro Tyr Phe Lys Gly Thr Tyr
    210                 215                 220

Gly Glu Asp Val Val Phe Val Cys Asn Asp Trp His Thr Gly Pro Leu
225                 230                 235                 240

Ala Ser Tyr Leu Lys Asn Asn Tyr Gln Pro Asn Gly Ile Tyr Arg Asn
                245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
290                 295                 300

Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
        355                 360                 365

Thr Ala Lys Tyr Asp Ala Thr Thr Ala Ile Glu Ala Lys Ala Leu Asn
    370                 375                 380

Lys Glu Ala Leu Gln Ala Glu Ala Gly Leu Pro Val Asp Arg Lys Ile
385                 390                 395                 400

Pro Leu Ile Ala Phe Ile Gly Arg Leu Glu Glu Gln Lys Gly Pro Asp
                405                 410                 415

Val Met Ala Ala Ala Ile Pro Glu Leu Met Gln Glu Asp Val Gln Ile
            420                 425                 430

Val Leu Leu Gly Thr Gly Lys Lys Lys Phe Glu Lys Leu Leu Lys Ser
        435                 440                 445

Met Glu Glu Lys Tyr Pro Gly Lys Val Arg Ala Val Val Lys Phe Asn
450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
            500                 505                 510

Val Ile Glu Gly Lys Thr Gly Phe His Met Gly Arg Leu Ser Val Asp
        515                 520                 525

Cys Lys Val Val Glu Pro Ser Asp Val Lys Val Ala Ala Thr Leu
530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
```

```
                565                 570                 575
Trp Glu Asn Val Leu Leu Gly Leu Gly Val Ala Gly Ser Ala Pro Gly
        580                 585                 590

Ile Glu Gly Asp Glu Ile Ala Pro Leu Ala Lys Glu Asn Val Ala Ala
        595                 600                 605

Pro
    610

(2) INFORMATION FOR SEQ ID NO: 8:

(i) SEQUENCE CHARACTERISTICS:
        (A) LENGTH: 2007 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (vi) ORIGINAL SOURCE:
        (A) ORGANISM: Zea mays (ix) FEATURE:
        (A) NAME/KEY: CDS
        (B) LOCATION: 1..2007

(xi) SEQUENCE DESCRIPTION: SEQ ID NO: 8:

GCT GAG GCT GAG GCC GGG GGC AAG GAC GCG CCG CCG GAG AGG AGC GGC        48
Ala Glu Ala Glu Ala Gly Gly Lys Asp Ala Pro Pro Glu Arg Ser Gly
                615                 620                 625

GAC GCC GCC AGG TTG CCC CGC GCT CGG CGC AAT GCG GTC TCC AAA CGG        96
Asp Ala Ala Arg Leu Pro Arg Ala Arg Arg Asn Ala Val Ser Lys Arg
        630                 635                 640

AGG GAT CCT CTT CAG CCG GTC GGC CGG TAC GGC TCC GCG ACG GGA AAC       144
Arg Asp Pro Leu Gln Pro Val Gly Arg Tyr Gly Ser Ala Thr Gly Asn
            645                 650                 655

ACG GCC AGG ACC GGC GCC GCG TCC TGC CAG AAC GCC GCA TTG GCG GAC       192
Thr Ala Arg Thr Gly Ala Ala Ser Cys Gln Asn Ala Ala Leu Ala Asp
        660                 665                 670

GTT GAG ATC GTT GAG ATC AAG TCC ATC GTC GCC GCG CCG CCG ACG AGC       240
Val Glu Ile Val Glu Ile Lys Ser Ile Val Ala Ala Pro Pro Thr Ser
675                 680                 685                 690

ATA GTG AAG TTC CCA GGG CGC GGG CTA CAG GAT GAT CCT TCC CTC TGG       288
Ile Val Lys Phe Pro Gly Arg Gly Leu Gln Asp Asp Pro Ser Leu Trp
                695                 700                 705

GAC ATA GCA CCG GAG ACT GTC CTC CCA GCC CCG AAG CCA CTG CAT GAA       336
Asp Ile Ala Pro Glu Thr Val Leu Pro Ala Pro Lys Pro Leu His Glu
            710                 715                 720

TCG CCT GCG GTT GAC GGA GAT TCA AAT GGA ATT GCA CCT CCT ACA GTT       384
Ser Pro Ala Val Asp Gly Asp Ser Asn Gly Ile Ala Pro Pro Thr Val
        725                 730                 735

GAG CCA TTA GTA CAG GAG GCC ACT TGG GAT TTC AAG AAA TAC ATC GGT       432
Glu Pro Leu Val Gln Glu Ala Thr Trp Asp Phe Lys Lys Tyr Ile Gly
    740                 745                 750

TTT GAC GAG CCT GAC GAA GCG AAG GAT GAT TCC AGG GTT GGT GCA GAT       480
Phe Asp Glu Pro Asp Glu Ala Lys Asp Asp Ser Arg Val Gly Ala Asp
755                 760                 765                 770

GAT GCT GGT TCT TTT GAA CAT TAT GGG ACA ATG ATT CTG GGC CTT TGT       528
Asp Ala Gly Ser Phe Glu His Tyr Gly Thr Met Ile Leu Gly Leu Cys
                775                 780                 785

GGG GAG AAT GTT ATG AAC GTG ATC GTG GTG GCT GCT GAA TGT TCT CCA       576
Gly Glu Asn Val Met Asn Val Ile Val Val Ala Ala Glu Cys Ser Pro
```

-continued

|  |  |  |  |
|---|---|---|---|
| 790 | 795 | 800 | |
| TGG TGC AAA ACA GGT GGT CTT GGA GAT GTT GTG GGA GCT TTA CCC AAG | 624 | | |
| Trp Cys Lys Thr Gly Gly Leu Gly Asp Val Val Gly Ala Leu Pro Lys | | | |
| 805 | 810 | 815 | |
| GCT TTA GCG AGA AGA GGA CAT CGT GTT ATG GTT GTG GTA CCA AGG TAT | 672 | | |
| Ala Leu Ala Arg Arg Gly His Arg Val Met Val Val Val Pro Arg Tyr | | | |
| 820 | 825 | 830 | |
| GGG GAC TAT GTG GAA GCC TTT GAT ATG GGA ATC CGG AAA TAC TAC AAA | 720 | | |
| Gly Asp Tyr Val Glu Ala Phe Asp Met Gly Ile Arg Lys Tyr Tyr Lys | | | |
| 835 | 840 | 845 | 850 |
| GCT GCA GGA CAG GAC CTA GAA GTG AAC TAT TTC CAT GCA TTT ATT GAT | 768 | | |
| Ala Ala Gly Gln Asp Leu Glu Val Asn Tyr Phe His Ala Phe Ile Asp | | | |
| 855 | 860 | 865 | |
| GGA GTC GAC TTT GTG TTC ATT GAT GCC TCT TTC CGG CAC CGT CAA GAT | 816 | | |
| Gly Val Asp Phe Val Phe Ile Asp Ala Ser Phe Arg His Arg Gln Asp | | | |
| 870 | 875 | 880 | |
| GAC ATA TAT GGG GGA AGT AGG CAG GAA ATC ATG AAG CGC ATG ATT TTG | 864 | | |
| Asp Ile Tyr Gly Gly Ser Arg Gln Glu Ile Met Lys Arg Met Ile Leu | | | |
| 885 | 890 | 895 | |
| TTT TGC AAG GTT GCT GTT GAG GTT CCT TGG CAC GTT CCA TGC GGT GGT | 912 | | |
| Phe Cys Lys Val Ala Val Glu Val Pro Trp His Val Pro Cys Gly Gly | | | |
| 900 | 905 | 910 | |
| GTG TGC TAC GGA GAT GGA AAT TTG GTG TTC ATT GCC ATG AAT TGG CAC | 960 | | |
| Val Cys Tyr Gly Asp Gly Asn Leu Val Phe Ile Ala Met Asn Trp His | | | |
| 915 | 920 | 925 | 930 |
| ACT GCA CTC CTG CCT GTT TAT CTG AAG GCA TAT TAC AGA GAC CAT GGG | 1008 | | |
| Thr Ala Leu Leu Pro Val Tyr Leu Lys Ala Tyr Tyr Arg Asp His Gly | | | |
| 935 | 940 | 945 | |
| TTA ATG CAG TAC ACT CGC TCC GTC CTC GTC ATA CAT AAC ATC GGC CAC | 1056 | | |
| Leu Met Gln Tyr Thr Arg Ser Val Leu Val Ile His Asn Ile Gly His | | | |
| 950 | 955 | 960 | |
| CAG GGC CGT GGT CCT GTA CAT GAA TTC CCG TAC ATG GAC TTG CTG AAC | 1104 | | |
| Gln Gly Arg Gly Pro Val His Glu Phe Pro Tyr Met Asp Leu Leu Asn | | | |
| 965 | 970 | 975 | |
| ACT AAC CTT CAA CAT TTC GAG CTG TAC GAT CCC GTC GGT GGC GAG CAC | 1152 | | |
| Thr Asn Leu Gln His Phe Glu Leu Tyr Asp Pro Val Gly Gly Glu His | | | |
| 980 | 985 | 990 | |
| GCC AAC ATC TTT GCC GCG TGT GTT CTG AAG ATG GCA GAC CGG GTG GTG | 1200 | | |
| Ala Asn Ile Phe Ala Ala Cys Val Leu Lys Met Ala Asp Arg Val Val | | | |
| 995 | 1000 | 1005 | 1010 |
| ACT GTC AGC CGC GGC TAC CTG TGG GAG CTG AAG ACA GTG GAA GGC GGC | 1248 | | |
| Thr Val Ser Arg Gly Tyr Leu Trp Glu Leu Lys Thr Val Glu Gly Gly | | | |
| 1015 | 1020 | 1025 | |
| TGG GGC CTC CAC GAC ATC ATC CGT TCT AAC GAC TGG AAG ATC AAT GGC | 1296 | | |
| Trp Gly Leu His Asp Ile Ile Arg Ser Asn Asp Trp Lys Ile Asn Gly | | | |
| 1030 | 1035 | 1040 | |
| ATT CGT GAA CGC ATC GAC CAC CAG GAG TGG AAC CCC AAG GTG GAC GTG | 1344 | | |
| Ile Arg Glu Arg Ile Asp His Gln Glu Trp Asn Pro Lys Val Asp Val | | | |
| 1045 | 1050 | 1055 | |
| CAC CTG CGG TCG GAC GGC TAC ACC AAC TAC TCC CTC GAG ACA CTC GAC | 1392 | | |
| His Leu Arg Ser Asp Gly Tyr Thr Asn Tyr Ser Leu Glu Thr Leu Asp | | | |
| 1060 | 1065 | 1070 | |
| GCT GGA AAG CGG CAG TGC AAG GCG GCC CTG CAG CGG GAC GTG GGC CTG | 1440 | | |
| Ala Gly Lys Arg Gln Cys Lys Ala Ala Leu Gln Arg Asp Val Gly Leu | | | |
| 1075 | 1080 | 1085 | 1090 |
| GAA GTG CGC GAC GAC GTG CCG CTG CTC GGC TTC ATC GGG CGT CTG GAT | 1488 | | |
| Glu Val Arg Asp Asp Val Pro Leu Leu Gly Phe Ile Gly Arg Leu Asp | | | |
| 1095 | 1100 | 1105 | |
| GGA CAG AAG GGC GTG GAC ATC ATC GGG GAC GCG ATG CCG TGG ATC GCG | 1536 | | |

-continued

```
Gly Gln Lys Gly Val Asp Ile Ile Gly Asp Ala Met Pro Trp Ile Ala
            1110                1115                1120

GGG CAG GAC GTG CAG CTG GTG ATG CTG GGC ACC GGC CCA CCT GAC CTG      1584
Gly Gln Asp Val Gln Leu Val Met Leu Gly Thr Gly Pro Pro Asp Leu
        1125                1130                1135

GAA CGA ATG CTG CAG CAC TTG GAG CGG GAG CAT CCC AAC AAG GTG CGC      1632
Glu Arg Met Leu Gln His Leu Glu Arg Glu His Pro Asn Lys Val Arg
    1140                1145                1150

GGG TGG GTC GGG TTC TCG GTC CTA ATG GTG CAT CGC ATC ACG CCG GGC      1680
Gly Trp Val Gly Phe Ser Val Leu Met Val His Arg Ile Thr Pro Gly
1155                1160                1165                1170

GCC AGC GTG CTG GTG ATG CCC TCC CGC TTC GCC GGG GGG CTG AAC CAG      1728
Ala Ser Val Leu Val Met Pro Ser Arg Phe Ala Gly Gly Leu Asn Gln
            1175                1180                1185

CTC TAC GCG ATG GCA TAC GGC ACC GTC CCT GTG GTG CAC GCC GTG GGC      1776
Leu Tyr Ala Met Ala Tyr Gly Thr Val Pro Val Val His Ala Val Gly
        1190                1195                1200

GGG CTC AGG GAC ACC GTG GCG CCG TTC GAC CCG TTC GGC GAC GCC GGG      1824
Gly Leu Arg Asp Thr Val Ala Pro Phe Asp Pro Phe Gly Asp Ala Gly
    1205                1210                1215

CTC GGG TGG ACT TTT GAC CGC GCC GAG GCC AAC AAG CTG ATC GAG GTG      1872
Leu Gly Trp Thr Phe Asp Arg Ala Glu Ala Asn Lys Leu Ile Glu Val
1220                1225                1230

CTC AGC CAC TGC CTC GAC ACG TAC CGA AAC TAC GAG GAG AGC TGG AAG      1920
Leu Ser His Cys Leu Asp Thr Tyr Arg Asn Tyr Glu Glu Ser Trp Lys
1235                1240                1245                1250

AGT CTC CAG GCG CGC GGC ATG TCG CAG AAC CTC AGC TGG GAC CAC GCG      1968
Ser Leu Gln Ala Arg Gly Met Ser Gln Asn Leu Ser Trp Asp His Ala
            1255                1260                1265

GCT GAG CTC TAC GAG GAC GTC CTT GTC AAG TAC CAG TGG                  2007
Ala Glu Leu Tyr Glu Asp Val Leu Val Lys Tyr Gln Trp
        1270                1275

(2) INFORMATION FOR SEQ ID NO: 9:

(i) SEQUENCE CHARACTERISTICS:
        (A) LENGTH: 669 amino acids
        (B) TYPE: amino acid
        (D) TOPOLOGY: linear (ii) MOLECULE TYPE: protein (xi) SEQUENCE DESCRIPTION: SEQ ID NO: 9:

Ala Glu Ala Glu Ala Gly Gly Lys Asp Ala Pro Pro Glu Arg Ser Gly
 1               5                  10                  15

Asp Ala Ala Arg Leu Pro Arg Ala Arg Arg Asn Ala Val Ser Lys Arg
                20                  25                  30

Arg Asp Pro Leu Gln Pro Val Gly Arg Tyr Gly Ser Ala Thr Gly Asn
            35                  40                  45

Thr Ala Arg Thr Gly Ala Ala Ser Cys Gln Asn Ala Ala Leu Ala Asp
        50                  55                  60

Val Glu Ile Val Glu Ile Lys Ser Ile Val Ala Ala Pro Pro Thr Ser
65                  70                  75                  80

Ile Val Lys Phe Pro Gly Arg Gly Leu Gln Asp Asp Pro Ser Leu Trp
                85                  90                  95

Asp Ile Ala Pro Glu Thr Val Leu Pro Ala Pro Lys Pro Leu His Glu
            100                 105                 110

Ser Pro Ala Val Asp Gly Asp Ser Asn Gly Ile Ala Pro Pro Thr Val
        115                 120                 125
```

```
Glu Pro Leu Val Gln Glu Ala Thr Trp Asp Phe Lys Lys Tyr Ile Gly
    130                 135                 140

Phe Asp Glu Pro Asp Glu Ala Lys Asp Asp Ser Arg Val Gly Ala Asp
145                 150                 155                 160

Asp Ala Gly Ser Phe Glu His Tyr Gly Thr Met Ile Leu Gly Leu Cys
                165                 170                 175

Gly Glu Asn Val Met Asn Val Ile Val Val Ala Ala Glu Cys Ser Pro
            180                 185                 190

Trp Cys Lys Thr Gly Gly Leu Gly Asp Val Val Gly Ala Leu Pro Lys
        195                 200                 205

Ala Leu Ala Arg Arg Gly His Arg Val Met Val Val Pro Arg Tyr
210                 215                 220

Gly Asp Tyr Val Glu Ala Phe Asp Met Gly Ile Arg Lys Tyr Tyr Lys
225                 230                 235                 240

Ala Ala Gly Gln Asp Leu Glu Val Asn Tyr Phe His Ala Phe Ile Asp
                245                 250                 255

Gly Val Asp Phe Val Phe Ile Asp Ala Ser Phe Arg His Arg Gln Asp
                260                 265                 270

Asp Ile Tyr Gly Gly Ser Arg Gln Glu Ile Met Lys Arg Met Ile Leu
            275                 280                 285

Phe Cys Lys Val Ala Val Glu Val Pro Trp His Val Pro Cys Gly Gly
290                 295                 300

Val Cys Tyr Gly Asp Gly Asn Leu Val Phe Ile Ala Met Asn Trp His
305                 310                 315                 320

Thr Ala Leu Leu Pro Val Tyr Leu Lys Ala Tyr Arg Asp His Gly
                325                 330                 335

Leu Met Gln Tyr Thr Arg Ser Val Leu Val Ile His Asn Ile Gly His
                340                 345                 350

Gln Gly Arg Gly Pro Val His Glu Phe Pro Tyr Met Asp Leu Leu Asn
            355                 360                 365

Thr Asn Leu Gln His Phe Glu Leu Tyr Asp Pro Val Gly Gly Glu His
370                 375                 380

Ala Asn Ile Phe Ala Ala Cys Val Leu Lys Met Ala Asp Arg Val Val
385                 390                 395                 400

Thr Val Ser Arg Gly Tyr Leu Trp Glu Leu Lys Thr Val Glu Gly Gly
            405                 410                 415

Trp Gly Leu His Asp Ile Ile Arg Ser Asn Asp Trp Lys Ile Asn Gly
            420                 425                 430

Ile Arg Glu Arg Ile Asp His Gln Glu Trp Asn Pro Lys Val Asp Val
        435                 440                 445

His Leu Arg Ser Asp Gly Tyr Thr Asn Tyr Ser Leu Glu Thr Leu Asp
    450                 455                 460

Ala Gly Lys Arg Gln Cys Lys Ala Ala Leu Gln Arg Asp Val Gly Leu
465                 470                 475                 480

Glu Val Arg Asp Asp Val Pro Leu Leu Gly Phe Ile Gly Arg Leu Asp
                485                 490                 495

Gly Gln Lys Gly Val Asp Ile Ile Gly Asp Ala Met Pro Trp Ile Ala
            500                 505                 510

Gly Gln Asp Val Gln Leu Val Met Leu Gly Thr Gly Pro Pro Asp Leu
            515                 520                 525

Glu Arg Met Leu Gln His Leu Glu Arg Glu His Pro Asn Lys Val Arg
            530                 535                 540

Gly Trp Val Gly Phe Ser Val Leu Met Val His Arg Ile Thr Pro Gly
```

```
                    545                 550                 555                 560
Ala Ser Val Leu Val Met Pro Ser Arg Phe Ala Gly Gly Leu Asn Gln
                565                 570                 575

Leu Tyr Ala Met Ala Tyr Gly Thr Val Pro Val Val His Ala Val Gly
                580                 585                 590

Gly Leu Arg Asp Thr Val Ala Pro Phe Asp Pro Phe Gly Asp Ala Gly
                595                 600                 605

Leu Gly Trp Thr Phe Asp Arg Ala Glu Ala Asn Lys Leu Ile Glu Val
            610                 615                 620

Leu Ser His Cys Leu Asp Thr Tyr Arg Asn Tyr Glu Glu Ser Trp Lys
625                 630                 635                 640

Ser Leu Gln Ala Arg Gly Met Ser Gln Asn Leu Ser Trp Asp His Ala
                645                 650                 655

Ala Glu Leu Tyr Glu Asp Val Leu Val Lys Tyr Gln Trp
                660                 665

(2) INFORMATION FOR SEQ ID NO: 10:

(i) SEQUENCE CHARACTERISTICS:
        (A) LENGTH: 2097 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (vi) ORIGINAL SOURCE:
        (A) ORGANISM: Zea mays (ix) FEATURE:
        (A) NAME/KEY: CDS
        (B) LOCATION: 1..2097

(xi) SEQUENCE DESCRIPTION: SEQ ID NO: 10:
```

| | | |
|---|---|---|
| ATG CCG GGG GCA ATC TCT TCC TCG TCG TCG GCT TTT CTC CTC CCC GTC<br>Met Pro Gly Ala Ile Ser Ser Ser Ser Ser Ala Phe Leu Leu Pro Val<br>670                        675                        680                        685 | | 48 |
| GCG TCC TCC TCG CCG CGG CGC AGG CGG GGC AGT GTG GGT GCT GCT CTG<br>Ala Ser Ser Ser Pro Arg Arg Arg Arg Gly Ser Val Gly Ala Ala Leu<br>                        690                        695                        700 | | 96 |
| CGC TCG TAC GGC TAC AGC GGC GCG GAG CTG CGG TTG CAT TGG GCG CGG<br>Arg Ser Tyr Gly Tyr Ser Gly Ala Glu Leu Arg Leu His Trp Ala Arg<br>                        705                        710                        715 | | 144 |
| CGG GGC CCG CCT CAG GAT GGA GCG GCG TCG GTA CGC GCC GCA GCG GCA<br>Arg Gly Pro Pro Gln Asp Gly Ala Ala Ser Val Arg Ala Ala Ala Ala<br>                        720                        725                        730 | | 192 |
| CCG GCC GGG GGC GAA AGC GAG GAG GCA GCG AAG AGC TCC TCC TCG TCC<br>Pro Ala Gly Gly Glu Ser Glu Glu Ala Ala Lys Ser Ser Ser Ser Ser<br>                        735                        740                        745 | | 240 |
| CAG GCG GGC GCT GTT CAG GGC AGC ACG GCC AAG GCT GTG GAT TCT GCT<br>Gln Ala Gly Ala Val Gln Gly Ser Thr Ala Lys Ala Val Asp Ser Ala<br>750                        755                        760                        765 | | 288 |
| TCA CCT CCC AAT CCT TTG ACA TCT GCT CCG AAG CAA AGT CAG AGC GCT<br>Ser Pro Pro Asn Pro Leu Thr Ser Ala Pro Lys Gln Ser Gln Ser Ala<br>                        770                        775                        780 | | 336 |
| GCA ATG CAA AAC GGA ACG AGT GGG GGC AGC AGC GCG AGC ACC GCC GCG<br>Ala Met Gln Asn Gly Thr Ser Gly Gly Ser Ser Ala Ser Thr Ala Ala<br>                        785                        790                        795 | | 384 |
| CCG GTG TCC GGA CCC AAA GCT GAT CAT CCA TCA GCT CCT GTC ACC AAG<br>Pro Val Ser Gly Pro Lys Ala Asp His Pro Ser Ala Pro Val Thr Lys | | 432 |

-continued

```
                800              805             810
AGA GAA ATC GAT GCC AGT GCG GTG AAG CCA GAG CCC GCA GGT GAT GAT       480
Arg Glu Ile Asp Ala Ser Ala Val Lys Pro Glu Pro Ala Gly Asp Asp
        815                 820                 825

GCT AGA CCG GTG GAA AGC ATA GGC ATC GCT GAA CCG GTG GAT GCT AAG       528
Ala Arg Pro Val Glu Ser Ile Gly Ile Ala Glu Pro Val Asp Ala Lys
830                 835                 840                 845

GCT GAT GCA GCT CCG GCT ACA GAT GCG GCG GCG AGT GCT CCT TAT GAC       576
Ala Asp Ala Ala Pro Ala Thr Asp Ala Ala Ala Ser Ala Pro Tyr Asp
            850                 855                 860

AGG GAG GAT AAT GAA CCT GGC CCT TTG GCT GGG CCT AAT GTG ATG AAC       624
Arg Glu Asp Asn Glu Pro Gly Pro Leu Ala Gly Pro Asn Val Met Asn
                865                 870                 875

GTC GTG GTG GTG GCT TCT GAA TGT GCT CCT TTC TGC AAG ACA GGT GGC       672
Val Val Val Val Ala Ser Glu Cys Ala Pro Phe Cys Lys Thr Gly Gly
                    880                 885                 890

CTT GGA GAT GTC GTG GGT GCT TTG CCT AAG GCT CTG GCG AGG AGA GGA       720
Leu Gly Asp Val Val Gly Ala Leu Pro Lys Ala Leu Ala Arg Arg Gly
895                 900                 905

CAC CGT GTT ATG GTC GTG ATA CCA AGA TAT GGA GAG TAT GCC GAA GCC       768
His Arg Val Met Val Val Ile Pro Arg Tyr Gly Glu Tyr Ala Glu Ala
910                 915                 920                 925

CGG GAT TTA GGT GTA AGG AGA CGT TAC AAG GTA GCT GGA CAG GAT TCA       816
Arg Asp Leu Gly Val Arg Arg Tyr Lys Val Ala Gly Gln Asp Ser
                930                 935                 940

GAA GTT ACT TAT TTT CAC TCT TAC ATT GAT GGA GTT GAT TTT GTA TTC       864
Glu Val Thr Tyr Phe His Ser Tyr Ile Asp Gly Val Asp Phe Val Phe
                945                 950                 955

GTA GAA GCC CCT CCC TTC CGG CAC CGG CAC AAT AAT ATT TAT GGG GGA       912
Val Glu Ala Pro Pro Phe Arg His Arg His Asn Asn Ile Tyr Gly Gly
                    960                 965                 970

GAA AGA TTG GAT ATT TTG AAG CGC ATG ATT TTG TTC TGC AAG GCC GCT       960
Glu Arg Leu Asp Ile Leu Lys Arg Met Ile Leu Phe Cys Lys Ala Ala
975                 980                 985

GTT GAG GTT CCA TGG TAT GCT CCA TGT GGC GGT ACT GTC TAT GGT GAT      1008
Val Glu Val Pro Trp Tyr Ala Pro Cys Gly Gly Thr Val Tyr Gly Asp
990                 995                 1000                1005

GGC AAC TTA GTT TTC ATT GCT AAT GAT TGG CAT ACC GCA CTT CTG CCT      1056
Gly Asn Leu Val Phe Ile Ala Asn Asp Trp His Thr Ala Leu Leu Pro
                    1010                1015                1020

GTC TAT CTA AAG GCC TAT TAC CGG GAC AAT GGT TTG ATG CAG TAT GCT      1104
Val Tyr Leu Lys Ala Tyr Tyr Arg Asp Asn Gly Leu Met Gln Tyr Ala
                1025                1030                1035

CGC TCT GTG CTT GTG ATA CAC AAC ATT GCT CAT CAG GGT CGT GGC CCT      1152
Arg Ser Val Leu Val Ile His Asn Ile Ala His Gln Gly Arg Gly Pro
            1040                1045                1050

GTA GAC GAC TTC GTC AAT TTT GAC TTG CCT GAA CAC TAC ATC GAC CAC      1200
Val Asp Asp Phe Val Asn Phe Asp Leu Pro Glu His Tyr Ile Asp His
1055                1060                1065

TTC AAA CTG TAT GAC AAC ATT GGT GGG GAT CAC AGC AAC GTT TTT GCT      1248
Phe Lys Leu Tyr Asp Asn Ile Gly Gly Asp His Ser Asn Val Phe Ala
1070                1075                1080                1085

GCG GGG CTG AAG ACG GCA GAC CGG GTG GTG ACC GTT AGC AAT GGC TAC      1296
Ala Gly Leu Lys Thr Ala Asp Arg Val Val Thr Val Ser Asn Gly Tyr
                1090                1095                1100

ATG TGG GAG CTG AAG ACT TCG GAA GGC GGG TGG GGC CTC CAC GAC ATC      1344
Met Trp Glu Leu Lys Thr Ser Glu Gly Gly Trp Gly Leu His Asp Ile
                1105                1110                1115

ATA AAC CAG AAC GAC TGG AAG CTG CAG GGC ATC GTG AAC GGC ATC GAC      1392
```

```
Ile Asn Gln Asn Asp Trp Lys Leu Gln Gly Ile Val Asn Gly Ile Asp
        1120                1125                1130

ATG AGC GAG TGG AAC CCC GCT GTG GAC GTG CAC CTC CAC TCC GAC GAC        1440
Met Ser Glu Trp Asn Pro Ala Val Asp Val His Leu His Ser Asp Asp
        1135                1140                1145

TAC ACC AAC TAC ACG TTC GAG ACG CTG GAC ACC GGC AAG CGG CAG TGC        1488
Tyr Thr Asn Tyr Thr Phe Glu Thr Leu Asp Thr Gly Lys Arg Gln Cys
1150                1155                1160                1165

AAG GCC GCC CTG CAG CGG CAG CTG GGC CTG CAG GTC CGC GAC GAC GTG        1536
Lys Ala Ala Leu Gln Arg Gln Leu Gly Leu Gln Val Arg Asp Asp Val
            1170                1175                1180

CCA CTG ATC GGG TTC ATC GGG CGG CTG GAC CAC CAG AAG GGC GTG GAC        1584
Pro Leu Ile Gly Phe Ile Gly Arg Leu Asp His Gln Lys Gly Val Asp
        1185                1190                1195

ATC ATC GCC GAC GCG ATC CAC TGG ATC GCG GGG CAG GAC GTG CAG CTC        1632
Ile Ile Ala Asp Ala Ile His Trp Ile Ala Gly Gln Asp Val Gln Leu
        1200                1205                1210

GTG ATG CTG GGC ACC GGG CGG GCC GAC CTG GAG GAC ATG CTG CGG CGG        1680
Val Met Leu Gly Thr Gly Arg Ala Asp Leu Glu Asp Met Leu Arg Arg
        1215                1220                1225

TTC GAG TCG GAG CAC AGC GAC AAG GTG CGC GCG TGG GTG GGG TTC TCG        1728
Phe Glu Ser Glu His Ser Asp Lys Val Arg Ala Trp Val Gly Phe Ser
1230                1235                1240                1245

GTG CCC CTG GCG CAC CGC ATC ACG GCG GGC GCG GAC ATC CTG CTG ATG        1776
Val Pro Leu Ala His Arg Ile Thr Ala Gly Ala Asp Ile Leu Leu Met
            1250                1255                1260

CCG TCG CGG TTC GAG CCG TGC GGG CTG AAC CAG CTC TAC GCC ATG GCG        1824
Pro Ser Arg Phe Glu Pro Cys Gly Leu Asn Gln Leu Tyr Ala Met Ala
        1265                1270                1275

TAC GGG ACC GTG CCC GTG GTG CAC GCC GTG GGG GGC CTC CGG GAC ACG        1872
Tyr Gly Thr Val Pro Val Val His Ala Val Gly Gly Leu Arg Asp Thr
        1280                1285                1290

GTG GCG CCG TTC GAC CCG TTC AAC GAC ACC GGG CTC GGG TGG ACG TTC        1920
Val Ala Pro Phe Asp Pro Phe Asn Asp Thr Gly Leu Gly Trp Thr Phe
        1295                1300                1305

GAC CGC GCG GAG GCG AAC CGG ATG ATC GAC GCG CTC TCG CAC TGC CTC        1968
Asp Arg Ala Glu Ala Asn Arg Met Ile Asp Ala Leu Ser His Cys Leu
1310                1315                1320                1325

ACC ACG TAC CGG AAC TAC AAG GAG AGC TGG CGC GCC TGC AGG GCG CGC        2016
Thr Thr Tyr Arg Asn Tyr Lys Glu Ser Trp Arg Ala Cys Arg Ala Arg
                1330                1335                1340

GGC ATG GCC GAG GAC CTC AGC TGG GAC CAC GCC GCC GTG CTG TAT GAG        2064
Gly Met Ala Glu Asp Leu Ser Trp Asp His Ala Ala Val Leu Tyr Glu
            1345                1350                1355

GAC GTG CTC GTC AAG GCG AAG TAC CAG TGG TGA                            2097
Asp Val Leu Val Lys Ala Lys Tyr Gln Trp *
        1360                1365
```

(2) INFORMATION FOR SEQ ID NO: 11:

(i) SEQUENCE CHARACTERISTICS:
        (A) LENGTH: 698 amino acids
        (B) TYPE: amino acid
        (D) TOPOLOGY: linear (ii) MOLECULE TYPE: protein (xi) SEQUENCE DESCRIPTION: SEQ ID NO: 11:

```
Met Pro Gly Ala Ile Ser Ser Ser Ser Ala Phe Leu Leu Pro Val
1               5                   10                  15

Ala Ser Ser Ser Pro Arg Arg Arg Arg Gly Ser Val Gly Ala Ala Leu
```

-continued

```
                20                  25                  30
Arg Ser Tyr Gly Tyr Ser Gly Ala Glu Leu Arg Leu His Trp Ala Arg
            35                  40                  45

Arg Gly Pro Pro Gln Asp Gly Ala Ala Ser Val Arg Ala Ala Ala
        50                  55                  60

Pro Ala Gly Gly Glu Ser Glu Ala Ala Lys Ser Ser Ser Ser
65                  70                  75                  80

Gln Ala Gly Ala Val Gln Gly Ser Thr Ala Lys Ala Val Asp Ser Ala
                85                  90                  95

Ser Pro Pro Asn Pro Leu Thr Ser Ala Pro Lys Gln Ser Gln Ser Ala
            100                 105                 110

Ala Met Gln Asn Gly Thr Ser Gly Gly Ser Ser Ala Ser Thr Ala Ala
            115                 120                 125

Pro Val Ser Gly Pro Lys Ala Asp His Pro Ser Ala Pro Val Thr Lys
            130                 135                 140

Arg Glu Ile Asp Ala Ser Ala Val Lys Pro Glu Pro Ala Gly Asp Asp
145                 150                 155                 160

Ala Arg Pro Val Glu Ser Ile Gly Ile Ala Glu Pro Val Asp Ala Lys
                165                 170                 175

Ala Asp Ala Ala Pro Ala Thr Asp Ala Ala Ser Ala Pro Tyr Asp
            180                 185                 190

Arg Glu Asp Asn Glu Pro Gly Pro Leu Ala Gly Pro Asn Val Met Asn
            195                 200                 205

Val Val Val Ala Ser Glu Cys Ala Pro Phe Cys Lys Thr Gly Gly
        210                 215                 220

Leu Gly Asp Val Val Gly Ala Leu Pro Lys Ala Leu Ala Arg Arg Gly
225                 230                 235                 240

His Arg Val Met Val Val Ile Pro Arg Tyr Gly Glu Tyr Ala Glu Ala
                245                 250                 255

Arg Asp Leu Gly Val Arg Arg Tyr Lys Val Ala Gly Gln Asp Ser
            260                 265                 270

Glu Val Thr Tyr Phe His Ser Tyr Ile Asp Gly Val Asp Phe Val Phe
            275                 280                 285

Val Glu Ala Pro Pro Phe Arg His Arg His Asn Asn Ile Tyr Gly Gly
        290                 295                 300

Glu Arg Leu Asp Ile Leu Lys Arg Met Ile Leu Phe Cys Lys Ala Ala
305                 310                 315                 320

Val Glu Val Pro Trp Tyr Ala Pro Cys Gly Gly Thr Val Tyr Gly Asp
                325                 330                 335

Gly Asn Leu Val Phe Ile Ala Asn Asp Trp His Thr Ala Leu Leu Pro
            340                 345                 350

Val Tyr Leu Lys Ala Tyr Tyr Arg Asp Asn Gly Leu Met Gln Tyr Ala
            355                 360                 365

Arg Ser Val Leu Val Ile His Asn Ile Ala His Gln Gly Arg Gly Pro
            370                 375                 380

Val Asp Asp Phe Val Asn Phe Asp Leu Pro Glu His Tyr Ile Asp His
385                 390                 395                 400

Phe Lys Leu Tyr Asp Asn Ile Gly Gly Asp His Ser Asn Val Phe Ala
                405                 410                 415

Ala Gly Leu Lys Thr Ala Asp Arg Val Val Thr Val Ser Asn Gly Tyr
            420                 425                 430

Met Trp Glu Leu Lys Thr Ser Glu Gly Gly Trp Gly Leu His Asp Ile
            435                 440                 445
```

```
Ile Asn Gln Asn Asp Trp Lys Leu Gln Gly Ile Val Asn Gly Ile Asp
    450                 455                 460
Met Ser Glu Trp Asn Pro Ala Val Asp Val His Leu His Ser Asp Asp
465                 470                 475                 480
Tyr Thr Asn Tyr Thr Phe Glu Thr Leu Asp Thr Gly Lys Arg Gln Cys
                485                 490                 495
Lys Ala Ala Leu Gln Arg Gln Leu Gly Leu Gln Val Arg Asp Asp Val
            500                 505                 510
Pro Leu Ile Gly Phe Ile Gly Arg Leu Asp His Gln Lys Gly Val Asp
        515                 520                 525
Ile Ile Ala Asp Ala Ile His Trp Ile Ala Gly Gln Asp Val Gln Leu
    530                 535                 540
Val Met Leu Gly Thr Gly Arg Ala Asp Leu Glu Asp Met Leu Arg Arg
545                 550                 555                 560
Phe Glu Ser Glu His Ser Asp Lys Val Arg Ala Trp Val Gly Phe Ser
                565                 570                 575
Val Pro Leu Ala His Arg Ile Thr Ala Gly Ala Asp Ile Leu Leu Met
            580                 585                 590
Pro Ser Arg Phe Glu Pro Cys Gly Leu Asn Gln Leu Tyr Ala Met Ala
        595                 600                 605
Tyr Gly Thr Val Pro Val Val His Ala Val Gly Gly Leu Arg Asp Thr
    610                 615                 620
Val Ala Pro Phe Asp Pro Phe Asn Asp Thr Gly Leu Gly Trp Thr Phe
625                 630                 635                 640
Asp Arg Ala Glu Ala Asn Arg Met Ile Asp Ala Leu Ser His Cys Leu
                645                 650                 655
Thr Thr Tyr Arg Asn Tyr Lys Glu Ser Trp Arg Ala Cys Arg Ala Arg
            660                 665                 670
Gly Met Ala Glu Asp Leu Ser Trp Asp His Ala Val Leu Tyr Glu
        675                 680                 685
Asp Val Leu Val Lys Ala Lys Tyr Gln Trp
    690                 695

(2) INFORMATION FOR SEQ ID NO: 12:

(i) SEQUENCE CHARACTERISTICS:
        (A) LENGTH: 1752 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (vi) ORIGINAL SOURCE:
        (A) ORGANISM: Zea mays (ix) FEATURE:
        (A) NAME/KEY: CDS
        (B) LOCATION: 1..1752

(xi) SEQUENCE DESCRIPTION: SEQ ID NO: 12:

TGC GTC GCG GAG CTG AGC AGG GAG GGG CCC GCG CCG CGC CCG CTG CCA        48
Cys Val Ala Glu Leu Ser Arg Glu Gly Pro Ala Pro Arg Pro Leu Pro
700                 705                 710                 715

CCC GCG CTG CTG GCG CCC CCG CTC GTG CCC GGC TTC CTC GCG CCG CCG        96
Pro Ala Leu Leu Ala Pro Pro Leu Val Pro Gly Phe Leu Ala Pro Pro
            720                 725                 730
```

-continued

```
GCC GAG CCC ACG GGT GAG CCG GCA TCG ACG CCG CCG CCC GTG CCC GAC        144
Ala Glu Pro Thr Gly Glu Pro Ala Ser Thr Pro Pro Pro Val Pro Asp
            735                 740                 745

GCC GGC CTG GGG GAC CTC GGT CTC GAA CCT GAA GGG ATT GCT GAA GGT        192
Ala Gly Leu Gly Asp Leu Gly Leu Glu Pro Glu Gly Ile Ala Glu Gly
            750                 755                 760

TCC ATC GAT AAC ACA GTA GTT GTG GCA AGT GAG CAA GAT TCT GAG ATT        240
Ser Ile Asp Asn Thr Val Val Val Ala Ser Glu Gln Asp Ser Glu Ile
            765                 770                 775

GTG GTT GGA AAG GAG CAA GCT CGA GCT AAA GTA ACA CAA AGC ATT GTC        288
Val Val Gly Lys Glu Gln Ala Arg Ala Lys Val Thr Gln Ser Ile Val
780                 785                 790                 795

TTT GTA ACC GGC GAA GCT TCT CCT TAT GCA AAG TCT GGG GGT CTA GGA        336
Phe Val Thr Gly Glu Ala Ser Pro Tyr Ala Lys Ser Gly Gly Leu Gly
                800                 805                 810

GAT GTT TGT GGT TCA TTG CCA GTT GCT CTT GCT GCT CGT GGT CAC CGT        384
Asp Val Cys Gly Ser Leu Pro Val Ala Leu Ala Ala Arg Gly His Arg
                815                 820                 825

GTG ATG GTT GTA ATG CCC AGA TAT TTA AAT GGT ACC TCC GAT AAG AAT        432
Val Met Val Val Met Pro Arg Tyr Leu Asn Gly Thr Ser Asp Lys Asn
            830                 835                 840

TAT GCA AAT GCA TTT TAC ACA GAA AAA CAC ATT CGG ATT CCA TGC TTT        480
Tyr Ala Asn Ala Phe Tyr Thr Glu Lys His Ile Arg Ile Pro Cys Phe
845                 850                 855

GGC GGT GAA CAT GAA GTT ACC TTC TTC CAT GAG TAT AGA GAT TCA GTT        528
Gly Gly Glu His Glu Val Thr Phe Phe His Glu Tyr Arg Asp Ser Val
860                 865                 870                 875

GAC TGG GTG TTT GTT GAT CAT CCC TCA TAT CAC AGA CCT GGA AAT TTA        576
Asp Trp Val Phe Val Asp His Pro Ser Tyr His Arg Pro Gly Asn Leu
                880                 885                 890

TAT GGA GAT AAG TTT GGT GCT TTT GGT GAT AAT CAG TTC AGA TAC ACA        624
Tyr Gly Asp Lys Phe Gly Ala Phe Gly Asp Asn Gln Phe Arg Tyr Thr
            895                 900                 905

CTC CTT TGC TAT GCT GCA TGT GAG GCT CCT TTG ATC CTT GAA TTG GGA        672
Leu Leu Cys Tyr Ala Ala Cys Glu Ala Pro Leu Ile Leu Glu Leu Gly
    910                 915                 920

GGA TAT ATT TAT GGA CAG AAT TGC ATG TTT GTT GTC AAT GAT TGG CAT        720
Gly Tyr Ile Tyr Gly Gln Asn Cys Met Phe Val Val Asn Asp Trp His
925                 930                 935

GCC AGT CTA GTG CCA GTC CTT CTT GCT GCA AAA TAT AGA CCA TAT GGT        768
Ala Ser Leu Val Pro Val Leu Leu Ala Ala Lys Tyr Arg Pro Tyr Gly
940                 945                 950                 955

GTT TAT AAA GAC TCC CGC AGC ATT CTT GTA ATA CAT AAT TTA GCA CAT        816
Val Tyr Lys Asp Ser Arg Ser Ile Leu Val Ile His Asn Leu Ala His
                960                 965                 970

CAG GGT GTA GAG CCT GCA AGC ACA TAT CCT GAC CTT GGG TTG CCA CCT        864
Gln Gly Val Glu Pro Ala Ser Thr Tyr Pro Asp Leu Gly Leu Pro Pro
            975                 980                 985

GAA TGG TAT GGA GCT CTG GAG TGG GTA TTC CCT GAA TGG GCG AGG AGG        912
Glu Trp Tyr Gly Ala Leu Glu Trp Val Phe Pro Glu Trp Ala Arg Arg
            990                 995                 1000

CAT GCC CTT GAC AAG GGT GAG GCA GTT AAT TTT TTG AAA GGT GCA GTT        960
His Ala Leu Asp Lys Gly Glu Ala Val Asn Phe Leu Lys Gly Ala Val
        1005                1010                1015

GTG ACA GCA GAT CGA ATC GTG ACT GTC AGT AAG GGT TAT TCG TGG GAG       1008
Val Thr Ala Asp Arg Ile Val Thr Val Ser Lys Gly Tyr Ser Trp Glu
1020                1025                1030                1035

GTC ACA ACT GCT GAA GGT GGA CAG GGC CTC AAT GAG CTC TTA AGC TCC       1056
Val Thr Thr Ala Glu Gly Gly Gln Gly Leu Asn Glu Leu Leu Ser Ser
                    1040                1045                1050
```

```
AGA AAG AGT GTA TTA AAC GGA ATT GTA AAT GGA ATT GAC ATT AAT GAT    1104
Arg Lys Ser Val Leu Asn Gly Ile Val Asn Gly Ile Asp Ile Asn Asp
            1055                1060                1065

TGG AAC CCT GCC ACA GAC AAA TGT ATC CCC TGT CAT TAT TCT GTT GAT    1152
Trp Asn Pro Ala Thr Asp Lys Cys Ile Pro Cys His Tyr Ser Val Asp
            1070                1075                1080

GAC CTC TCT GGA AAG GCC AAA TGT AAA GGT GCA TTG CAG AAG GAG CTG    1200
Asp Leu Ser Gly Lys Ala Lys Cys Lys Gly Ala Leu Gln Lys Glu Leu
            1085                1090                1095

GGT TTA CCT ATA AGG CCT GAT GTT CCT CTG ATT GGC TTT ATT GGA AGG    1248
Gly Leu Pro Ile Arg Pro Asp Val Pro Leu Ile Gly Phe Ile Gly Arg
1100                1105                1110                1115

TTG GAT TAT CAG AAA GGC ATT GAT CTC ATT CAA CTT ATC ATA CCA GAT    1296
Leu Asp Tyr Gln Lys Gly Ile Asp Leu Ile Gln Leu Ile Ile Pro Asp
            1120                1125                1130

CTC ATG CGG GAA GAT GTT CAA TTT GTC ATG CTT GGA TCT GGT GAC CCA    1344
Leu Met Arg Glu Asp Val Gln Phe Val Met Leu Gly Ser Gly Asp Pro
            1135                1140                1145

GAG CTT GAA GAT TGG ATG AGA TCT ACA GAG TCG ATC TTC AAG GAT AAA    1392
Glu Leu Glu Asp Trp Met Arg Ser Thr Glu Ser Ile Phe Lys Asp Lys
            1150                1155                1160

TTT CGT GGA TGG GTT GGA TTT AGT GTT CCA GTT TCC CAC CGA ATA ACT    1440
Phe Arg Gly Trp Val Gly Phe Ser Val Pro Val Ser His Arg Ile Thr
            1165                1170                1175

GCC GGC TGC GAT ATA TTG TTA ATG CCA TCC AGA TTC GAA CCT TGT GGT    1488
Ala Gly Cys Asp Ile Leu Leu Met Pro Ser Arg Phe Glu Pro Cys Gly
1180                1185                1190                1195

CTC AAT CAG CTA TAT GCT ATG CAG TAT GGC ACA GTT CCT GTT GTC CAT    1536
Leu Asn Gln Leu Tyr Ala Met Gln Tyr Gly Thr Val Pro Val Val His
            1200                1205                1210

GCA ACT GGG GGC CTT AGA GAT ACC GTG GAG AAC TTC AAC CCT TTC GGT    1584
Ala Thr Gly Gly Leu Arg Asp Thr Val Glu Asn Phe Asn Pro Phe Gly
            1215                1220                1225

GAG AAT GGA GAG CAG GGT ACA GGG TGG GCA TTC GCA CCC CTA ACC ACA    1632
Glu Asn Gly Glu Gln Gly Thr Gly Trp Ala Phe Ala Pro Leu Thr Thr
            1230                1235                1240

GAA AAC ATG TTT GTG GAC ATT GCG AAC TGC AAT ATC TAC ATA CAG GGA    1680
Glu Asn Met Phe Val Asp Ile Ala Asn Cys Asn Ile Tyr Ile Gln Gly
            1245                1250                1255

ACA CAA GTC CTC CTG GGA AGG GCT AAT GAA GCG AGG CAT GTC AAA AGA    1728
Thr Gln Val Leu Leu Gly Arg Ala Asn Glu Ala Arg His Val Lys Arg
1260                1265                1270                1275

CTT CAC GTG GGA CCA TGC CGC TGA                                    1752
Leu His Val Gly Pro Cys Arg  *
            1280
```

(2) INFORMATION FOR SEQ ID NO: 13:

(i) SEQUENCE CHARACTERISTICS:
        (A) LENGTH: 583 amino acids
        (B) TYPE: amino acid
        (D) TOPOLOGY: linear (ii) MOLECULE TYPE: protein (xi) SEQUENCE DESCRIPTION: SEQ ID NO: 13:

```
Cys Val Ala Glu Leu Ser Arg Glu Gly Pro Ala Pro Arg Pro Leu Pro
 1               5                  10                  15

Pro Ala Leu Leu Ala Pro Pro Leu Val Pro Gly Phe Leu Ala Pro Pro
            20                  25                  30
```

```
Ala Glu Pro Thr Gly Glu Pro Ala Ser Thr Pro Pro Val Pro Asp
         35                  40                  45

Ala Gly Leu Gly Asp Leu Gly Leu Glu Pro Glu Gly Ile Ala Glu Gly
     50                  55                  60

Ser Ile Asp Asn Thr Val Val Ala Ser Glu Gln Asp Ser Glu Ile
 65                  70                  75                  80

Val Val Gly Lys Glu Gln Ala Arg Ala Lys Val Thr Gln Ser Ile Val
                 85                  90                  95

Phe Val Thr Gly Glu Ala Ser Pro Tyr Ala Lys Ser Gly Gly Leu Gly
             100                 105                 110

Asp Val Cys Gly Ser Leu Pro Val Ala Leu Ala Ala Arg Gly His Arg
         115                 120                 125

Val Met Val Met Pro Arg Tyr Leu Asn Gly Thr Ser Asp Lys Asn
 130                 135                 140

Tyr Ala Asn Ala Phe Tyr Thr Glu Lys His Ile Arg Ile Pro Cys Phe
145                 150                 155                 160

Gly Gly Glu His Glu Val Thr Phe Phe His Glu Tyr Arg Asp Ser Val
                 165                 170                 175

Asp Trp Val Phe Val Asp His Pro Ser Tyr His Arg Pro Gly Asn Leu
             180                 185                 190

Tyr Gly Asp Lys Phe Gly Ala Phe Gly Asp Asn Gln Phe Arg Tyr Thr
         195                 200                 205

Leu Leu Cys Tyr Ala Ala Cys Glu Ala Pro Leu Ile Leu Glu Leu Gly
         210                 215                 220

Gly Tyr Ile Tyr Gly Gln Asn Cys Met Phe Val Val Asn Asp Trp His
225                 230                 235                 240

Ala Ser Leu Val Pro Val Leu Leu Ala Ala Lys Tyr Arg Pro Tyr Gly
                 245                 250                 255

Val Tyr Lys Asp Ser Arg Ser Ile Leu Val Ile His Asn Leu Ala His
             260                 265                 270

Gln Gly Val Glu Pro Ala Ser Thr Tyr Pro Asp Leu Gly Leu Pro Pro
         275                 280                 285

Glu Trp Tyr Gly Ala Leu Glu Trp Val Phe Pro Glu Trp Ala Arg Arg
         290                 295                 300

His Ala Leu Asp Lys Gly Glu Ala Val Asn Phe Leu Lys Gly Ala Val
305                 310                 315                 320

Val Thr Ala Asp Arg Ile Val Thr Val Ser Lys Gly Tyr Ser Trp Glu
                 325                 330                 335

Val Thr Thr Ala Glu Gly Gly Gln Gly Leu Asn Glu Leu Leu Ser Ser
             340                 345                 350

Arg Lys Ser Val Leu Asn Gly Ile Val Asn Gly Ile Asp Ile Asn Asp
         355                 360                 365

Trp Asn Pro Ala Thr Asp Lys Cys Ile Pro Cys His Tyr Ser Val Asp
370                 375                 380

Asp Leu Ser Gly Lys Ala Lys Cys Lys Gly Ala Leu Gln Lys Glu Leu
385                 390                 395                 400

Gly Leu Pro Ile Arg Pro Asp Val Pro Leu Ile Gly Phe Ile Gly Arg
             405                 410                 415

Leu Asp Tyr Gln Lys Gly Ile Asp Leu Ile Gln Leu Ile Ile Pro Asp
         420                 425                 430

Leu Met Arg Glu Asp Val Gln Phe Val Met Leu Gly Ser Gly Asp Pro
         435                 440                 445

Glu Leu Glu Asp Trp Met Arg Ser Thr Glu Ser Ile Phe Lys Asp Lys
```

```
                  450                 455                 460
Phe Arg Gly Trp Val Gly Phe Ser Val Pro Val Ser His Arg Ile Thr
465                 470                 475                 480

Ala Gly Cys Asp Ile Leu Leu Met Pro Ser Arg Phe Glu Pro Cys Gly
                485                 490                 495

Leu Asn Gln Leu Tyr Ala Met Gln Tyr Gly Thr Val Pro Val Val His
                500                 505                 510

Ala Thr Gly Gly Leu Arg Asp Thr Val Glu Asn Phe Asn Pro Phe Gly
                515                 520                 525

Glu Asn Gly Glu Gln Gly Thr Gly Trp Ala Phe Ala Pro Leu Thr Thr
530                 535                 540

Glu Asn Met Phe Val Asp Ile Ala Asn Cys Asn Ile Tyr Ile Gln Gly
545                 550                 555                 560

Thr Gln Val Leu Leu Gly Arg Ala Asn Glu Ala Arg His Val Lys Arg
                565                 570                 575

Leu His Val Gly Pro Cys Arg
                580

(2) INFORMATION FOR SEQ ID NO: 14:

(i) SEQUENCE CHARACTERISTICS:
        (A) LENGTH: 2725 base pairs
        (B) TYPE: nucleic acid
        (C) STRANDEDNESS: single
        (D) TOPOLOGY: Not Relevant (ii) MOLECULE TYPE: mRNA (iii) HYPOTHETICAL: NO (vi) ORIGINAL SOURCE:
        (A) ORGANISM: Zea mays (ix) FEATURE:
        (A) NAME/KEY: sig_peptide
        (B) LOCATION: 91..264

(ix) FEATURE:
        (A) NAME/KEY: mat_peptide
        (B) LOCATION: 265..2487

(ix) FEATURE:
        (A) NAME/KEY: CDS
        (B) LOCATION: 91..2490

(xi) SEQUENCE DESCRIPTION: SEQ ID NO: 14:

GGCCCAGAGC AGACCCGGAT TTCGCTCTTG CGGTCGCTGG GGTTTTAGCA TTGGCTGATC          60

AGTTCGATCC GATCCGGCTG CGAAGGCGAG ATG GCG TTC CGG GTT TCT GGG GCG         114
                                 Met Ala Phe Arg Val Ser Gly Ala
                                 -58             -55

GTG CTC GGT GGG GCC GTA AGG GCT CCC CGA CTC ACC GGC GGC GGG GAG          162
Val Leu Gly Gly Ala Val Arg Ala Pro Arg Leu Thr Gly Gly Gly Glu
-50                 -45                 -40                 -35

GGT AGT CTA GTC TTC CGG CAC ACC GGC CTC TTC TTA ACT CGG GGT GCT          210
Gly Ser Leu Val Phe Arg His Thr Gly Leu Phe Leu Thr Arg Gly Ala
                -30                 -25                 -20

CGA GTT GGA TGT TCG GGG ACG CAC GGG GCC ATG CGC GCG GCG GCC GCG          258
Arg Val Gly Cys Ser Gly Thr His Gly Ala Met Arg Ala Ala Ala Ala
            -15                 -10                 -5

GCC AGG AAG GCG GTC ATG GTT CCT GAG GGC GAG AAT GAT GGC CTC GCA          306
Ala Arg Lys Ala Val Met Val Pro Glu Gly Glu Asn Asp Gly Leu Ala
        1               5                   10

TCA AGG GCT GAC TCG GCT CAA TTC CAG TCG GAT GAA CTG GAG GTA CCA          354
```

```
Ser Arg Ala Asp Ser Ala Gln Phe Gln Ser Asp Glu Leu Glu Val Pro
 15              20                  25                  30

GAC ATT TCT GAA GAG ACA ACG TGC GGT GCT GGT GTG GCT GAT GCT CAA         402
Asp Ile Ser Glu Glu Thr Thr Cys Gly Ala Gly Val Ala Asp Ala Gln
                     35                  40                  45

GCC TTG AAC AGA GTT CGA GTG GTC CCC CCA CCA AGC GAT GGA CAA AAA         450
Ala Leu Asn Arg Val Arg Val Val Pro Pro Pro Ser Asp Gly Gln Lys
                 50                  55                  60

ATA TTC CAG ATT GAC CCC ATG TTG CAA GGC TAT AAG TAC CAT CTT GAG         498
Ile Phe Gln Ile Asp Pro Met Leu Gln Gly Tyr Lys Tyr His Leu Glu
             65                  70                  75

TAT CGG TAC AGC CTC TAT AGA AGA ATC CGT TCA GAC ATT GAT GAA CAT         546
Tyr Arg Tyr Ser Leu Tyr Arg Arg Ile Arg Ser Asp Ile Asp Glu His
         80                  85                  90

GAA GGA GGC TTG GAA GCC TTC TCC CGT AGT TAT GAG AAG TTT GGA TTT         594
Glu Gly Gly Leu Glu Ala Phe Ser Arg Ser Tyr Glu Lys Phe Gly Phe
 95                 100                 105                 110

AAT GCC AGC GCG GAA GGT ATC ACA TAT CGA GAA TGG GCT CCT GGA GCA         642
Asn Ala Ser Ala Glu Gly Ile Thr Tyr Arg Glu Trp Ala Pro Gly Ala
                115                 120                 125

TTT TCT GCA GCA TTG GTG GGT GAC GTC AAC AAC TGG GAT CCA AAT GCA         690
Phe Ser Ala Ala Leu Val Gly Asp Val Asn Asn Trp Asp Pro Asn Ala
            130                 135                 140

GAT CGT ATG AGC AAA AAT GAG TTT GGT GTT TGG GAA ATT TTT CTG CCT         738
Asp Arg Met Ser Lys Asn Glu Phe Gly Val Trp Glu Ile Phe Leu Pro
        145                 150                 155

AAC AAT GCA GAT GGT ACA TCA CCT ATT CCT CAT GGA TCT CGT GTA AAG         786
Asn Asn Ala Asp Gly Thr Ser Pro Ile Pro His Gly Ser Arg Val Lys
    160                 165                 170

GTG AGA ATG GAT ACT CCA TCA GGG ATA AAG GAT TCA ATT CCA GCC TGG         834
Val Arg Met Asp Thr Pro Ser Gly Ile Lys Asp Ser Ile Pro Ala Trp
175                 180                 185                 190

ATC AAG TAC TCA GTG CAG GCC CCA GGA GAA ATA CCA TAT GAT GGG ATT         882
Ile Lys Tyr Ser Val Gln Ala Pro Gly Glu Ile Pro Tyr Asp Gly Ile
                195                 200                 205

TAT TAT GAT CCT CCT GAA GAG GTA AAG TAT GTG TTC AGG CAT GCG CAA         930
Tyr Tyr Asp Pro Pro Glu Glu Val Lys Tyr Val Phe Arg His Ala Gln
            210                 215                 220

CCT AAA CGA CCA AAA TCA TTG CGG ATA TAT GAA ACA CAT GTC GGA ATG         978
Pro Lys Arg Pro Lys Ser Leu Arg Ile Tyr Glu Thr His Val Gly Met
        225                 230                 235

AGT AGC CCG GAA CCG AAG ATA AAC ACA TAT GTA AAC TTT AGG GAT GAA        1026
Ser Ser Pro Glu Pro Lys Ile Asn Thr Tyr Val Asn Phe Arg Asp Glu
    240                 245                 250

GTC CTC CCA AGA ATA AAA AAA CTT GGA TAC AAT GCA GTG CAA ATA ATG        1074
Val Leu Pro Arg Ile Lys Lys Leu Gly Tyr Asn Ala Val Gln Ile Met
255                 260                 265                 270

GCA ATC CAA GAG CAC TCA TAT TAT GGA AGC TTT GGA TAC CAT GTA ACT        1122
Ala Ile Gln Glu His Ser Tyr Tyr Gly Ser Phe Gly Tyr His Val Thr
                275                 280                 285

AAT TTT TTT GCG CCA AGT AGT CGT TTT GGT ACC CCA GAA GAT TTG AAG        1170
Asn Phe Phe Ala Pro Ser Ser Arg Phe Gly Thr Pro Glu Asp Leu Lys
            290                 295                 300

TCT TTG ATT GAT AGA GCA CAT GAG CTT GGT TTG CTA GTT CTC ATG GAT        1218
Ser Leu Ile Asp Arg Ala His Glu Leu Gly Leu Leu Val Leu Met Asp
        305                 310                 315

GTG GTT CAT AGT CAT GCG TCA AGT AAT ACT CTG GAT GGG TTG AAT GGT        1266
Val Val His Ser His Ala Ser Ser Asn Thr Leu Asp Gly Leu Asn Gly
    320                 325                 330
```

-continued

| | | |
|---|---|---|
| TTT GAT GGT ACA GAT ACA CAT TAC TTT CAC AGT GGT CCA CGT GGC CAT<br>Phe Asp Gly Thr Asp Thr His Tyr Phe His Ser Gly Pro Arg Gly His<br>335                 340               345               350 | 1314 |
| CAC TGG ATG TGG GAT TCT CGC CTA TTT AAC TAT GGG AAC TGG GAA GTT<br>His Trp Met Trp Asp Ser Arg Leu Phe Asn Tyr Gly Asn Trp Glu Val<br>               355               360               365 | 1362 |
| TTA AGA TTT CTT CTC TCC AAT GCT AGA TGG TGG CTC GAG GAA TAT AAG<br>Leu Arg Phe Leu Leu Ser Asn Ala Arg Trp Trp Leu Glu Glu Tyr Lys<br>         370               375               380 | 1410 |
| TTT GAT GGT TTC CGT TTT GAT GGT GTG ACC TCC ATG ATG TAC ACT CAC<br>Phe Asp Gly Phe Arg Phe Asp Gly Val Thr Ser Met Met Tyr Thr His<br>385                 390               395 | 1458 |
| CAC GGA TTA CAA GTA ACA TTT ACG GGG AAC TTC AAT GAG TAT TTT GGC<br>His Gly Leu Gln Val Thr Phe Thr Gly Asn Phe Asn Glu Tyr Phe Gly<br>    400               405               410 | 1506 |
| TTT GCC ACC GAT GTA GAT GCA GTG GTT TAC TTG ATG CTG GTA AAT GAT<br>Phe Ala Thr Asp Val Asp Ala Val Val Tyr Leu Met Leu Val Asn Asp<br>415                 420               425               430 | 1554 |
| CTA ATT CAT GGA CTT TAT CCT GAG GCT GTA ACC ATT GGT GAA GAT GTT<br>Leu Ile His Gly Leu Tyr Pro Glu Ala Val Thr Ile Gly Glu Asp Val<br>               435               440               445 | 1602 |
| AGT GGA ATG CCT ACA TTT GCC CTT CCT GTT CAC GAT GGT GGG GTA GGT<br>Ser Gly Met Pro Thr Phe Ala Leu Pro Val His Asp Gly Gly Val Gly<br>         450               455               460 | 1650 |
| TTT GAC TAT CGG ATG CAT ATG GCT GTG GCT GAC AAA TGG ATT GAC CTT<br>Phe Asp Tyr Arg Met His Met Ala Val Ala Asp Lys Trp Ile Asp Leu<br>465                 470               475 | 1698 |
| CTC AAG CAA AGT GAT GAA ACT TGG AAG ATG GGT GAT ATT GTG CAC ACA<br>Leu Lys Gln Ser Asp Glu Thr Trp Lys Met Gly Asp Ile Val His Thr<br>               480               485               490 | 1746 |
| CTG ACA AAT AGG AGG TGG TTA GAG AAG TGT GTA ACT TAT GCT GAA AGT<br>Leu Thr Asn Arg Arg Trp Leu Glu Lys Cys Val Thr Tyr Ala Glu Ser<br>495                 500               505               510 | 1794 |
| CAT GAT CAA GCA TTA GTC GGC GAC AAG ACT ATT GCG TTT TGG TTG ATG<br>His Asp Gln Ala Leu Val Gly Asp Lys Thr Ile Ala Phe Trp Leu Met<br>               515               520               525 | 1842 |
| GAC AAG GAT ATG TAT GAT TTC ATG GCC CTC GAT AGA CCT TCA ACT CCT<br>Asp Lys Asp Met Tyr Asp Phe Met Ala Leu Asp Arg Pro Ser Thr Pro<br>                 530               535               540 | 1890 |
| ACC ATT GAT CGT GGG ATA GCA TTA CAT AAG ATG ATT AGA CTT ATC ACA<br>Thr Ile Asp Arg Gly Ile Ala Leu His Lys Met Ile Arg Leu Ile Thr<br>545                 550               555 | 1938 |
| ATG GGT TTA GGA GGA GAG GGC TAT CTT AAT TTC ATG GGA AAT GAG TTT<br>Met Gly Leu Gly Gly Glu Gly Tyr Leu Asn Phe Met Gly Asn Glu Phe<br>         560               565               570 | 1986 |
| GGA CAT CCT GAA TGG ATA GAT TTT CCA AGA GGT CCG CAA AGA CTT CCA<br>Gly His Pro Glu Trp Ile Asp Phe Pro Arg Gly Pro Gln Arg Leu Pro<br>575                 580               585               590 | 2034 |
| AGT GGT AAG TTT ATT CCA GGG AAT AAC AAC AGT TAT GAC AAA TGT CGT<br>Ser Gly Lys Phe Ile Pro Gly Asn Asn Asn Ser Tyr Asp Lys Cys Arg<br>               595               600               605 | 2082 |
| CGA AGA TTT GAC CTG GGT GAT GCA GAC TAT CTT AGG TAT CAT GGT ATG<br>Arg Arg Phe Asp Leu Gly Asp Ala Asp Tyr Leu Arg Tyr His Gly Met<br>         610               615               620 | 2130 |
| CAA GAG TTT GAT CAG GCA ATG CAA CAT CTT GAG CAA AAA TAT GAA TTC<br>Gln Glu Phe Asp Gln Ala Met Gln His Leu Glu Gln Lys Tyr Glu Phe<br>625                 630               635 | 2178 |
| ATG ACA TCT GAT CAC CAG TAT ATT TCC CGG AAA CAT GAG GAG GAT AAG<br>Met Thr Ser Asp His Gln Tyr Ile Ser Arg Lys His Glu Glu Asp Lys<br>         640               645               650 | 2226 |

-continued

```
GTG ATT GTG TTC GAA AAG GGA GAT TTG GTA TTT GTG TTC AAC TTC CAC        2274
Val Ile Val Phe Glu Lys Gly Asp Leu Val Phe Val Phe Asn Phe His
655                 660                 665                 670

TGC AAC AAC AGC TAT TTT GAC TAC CGT ATT GGT TGT CGA AAG CCT GGG        2322
Cys Asn Asn Ser Tyr Phe Asp Tyr Arg Ile Gly Cys Arg Lys Pro Gly
                675                 680                 685

GTG TAT AAG GTG GTC TTG GAC TCC GAC GCT GGA CTA TTT GGT GGA TTT        2370
Val Tyr Lys Val Val Leu Asp Ser Asp Ala Gly Leu Phe Gly Gly Phe
            690                 695                 700

AGC AGG ATC CAT CAC GCA GCC GAG CAC TTC ACC GCC GAC TGT TCG CAT        2418
Ser Arg Ile His His Ala Ala Glu His Phe Thr Ala Asp Cys Ser His
        705                 710                 715

GAT AAT AGG CCA TAT TCA TTC TCG GTT TAT ACA CCA AGC AGA ACA TGT        2466
Asp Asn Arg Pro Tyr Ser Phe Ser Val Tyr Thr Pro Ser Arg Thr Cys
    720                 725                 730

GTC GTC TAT GCT CCA GTG GAG TGA TAGCGGGGTA CTCGTTGCTG CGCGGCATGT       2520
Val Val Tyr Ala Pro Val Glu *
735                 740

GTGGGGCTGT CGATGTGAGG AAAAACCTTC TTCCAAAACC GGCAGATGCA TGCATGCATG      2580

CTACAATAAG GTTCTGATAC TTTAATCGAT GCTGGAAAGC CCATGCATCT CGCTGCGTTG      2640

TCCTCTCTAT ATATATAAGA CCTTCAAGGT GTCAATTAAA CATAGAGTTT CGTTTTTCG       2700

CTTTCCTAAA AAAAAAAAAA AAAAA                                            2725
```

(2) INFORMATION FOR SEQ ID NO: 15:

(i) SEQUENCE CHARACTERISTICS:
        (A) LENGTH: 799 amino acids
        (B) TYPE: amino acid
        (D) TOPOLOGY: linear (ii) MOLECULE TYPE: protein (xi) SEQUENCE DESCRIPTION: SEQ ID NO: 15:

```
Met Ala Phe Arg Val Ser Gly Ala Val Leu Gly Gly Ala Val Arg Ala
-58             -55                 -50                 -45

Pro Arg Leu Thr Gly Gly Gly Glu Gly Ser Leu Val Phe Arg His Thr
        -40                 -35                 -30

Gly Leu Phe Leu Thr Arg Gly Ala Arg Val Gly Cys Ser Gly Thr His
    -25                 -20                 -15

Gly Ala Met Arg Ala Ala Ala Ala Arg Lys Ala Val Met Val Pro
-10             -5                   1                   5

Glu Gly Glu Asn Asp Gly Leu Ala Ser Arg Ala Asp Ser Ala Gln Phe
            10                  15                  20

Gln Ser Asp Glu Leu Glu Val Pro Asp Ile Ser Glu Glu Thr Thr Cys
        25                  30                  35

Gly Ala Gly Val Ala Asp Ala Gln Ala Leu Asn Arg Val Arg Val Val
    40                  45                  50

Pro Pro Pro Ser Asp Gly Gln Lys Ile Phe Gln Ile Asp Pro Met Leu
55                  60                  65                  70

Gln Gly Tyr Lys Tyr His Leu Glu Tyr Tyr Ser Leu Tyr Arg Arg
            75                  80                  85

Ile Arg Ser Asp Ile Asp Glu His Glu Gly Gly Leu Glu Ala Phe Ser
        90                  95                  100

Arg Ser Tyr Glu Lys Phe Gly Phe Asn Ala Ser Ala Glu Gly Ile Thr
    105                 110                 115

Tyr Arg Glu Trp Ala Pro Gly Ala Phe Ser Ala Ala Leu Val Gly Asp
```

-continued

```
            120                 125                 130
Val Asn Asn Trp Asp Pro Asn Ala Asp Arg Met Ser Lys Asn Glu Phe
135                 140                 145                 150

Gly Val Trp Glu Ile Phe Leu Pro Asn Ala Asp Gly Thr Ser Pro
            155                 160                 165

Ile Pro His Gly Ser Arg Val Lys Val Arg Met Asp Thr Pro Ser Gly
            170                 175                 180

Ile Lys Asp Ser Ile Pro Ala Trp Ile Lys Tyr Ser Val Gln Ala Pro
            185                 190                 195

Gly Glu Ile Pro Tyr Asp Gly Ile Tyr Asp Pro Pro Glu Glu Val
200                 205                 210

Lys Tyr Val Phe Arg His Ala Gln Pro Lys Arg Pro Lys Ser Leu Arg
215                 220                 225                 230

Ile Tyr Glu Thr His Val Gly Met Ser Ser Pro Glu Pro Lys Ile Asn
            235                 240                 245

Thr Tyr Val Asn Phe Arg Asp Glu Val Leu Pro Arg Ile Lys Lys Leu
            250                 255                 260

Gly Tyr Asn Ala Val Gln Ile Met Ala Ile Gln Glu His Ser Tyr Tyr
            265                 270                 275

Gly Ser Phe Gly Tyr His Val Thr Asn Phe Phe Ala Pro Ser Ser Arg
            280                 285                 290

Phe Gly Thr Pro Glu Asp Leu Lys Ser Leu Ile Asp Arg Ala His Glu
295                 300                 305                 310

Leu Gly Leu Leu Val Leu Met Asp Val Val His Ser His Ala Ser Ser
            315                 320                 325

Asn Thr Leu Asp Gly Leu Asn Gly Phe Asp Gly Thr Asp Thr His Tyr
            330                 335                 340

Phe His Ser Gly Pro Arg Gly His His Trp Met Trp Asp Ser Arg Leu
            345                 350                 355

Phe Asn Tyr Gly Asn Trp Glu Val Leu Arg Phe Leu Leu Ser Asn Ala
            360                 365                 370

Arg Trp Trp Leu Glu Glu Tyr Lys Phe Asp Gly Phe Arg Phe Asp Gly
375                 380                 385                 390

Val Thr Ser Met Met Tyr Thr His His Gly Leu Gln Val Thr Phe Thr
            395                 400                 405

Gly Asn Phe Asn Glu Tyr Phe Gly Phe Ala Thr Asp Val Asp Ala Val
            410                 415                 420

Val Tyr Leu Met Leu Val Asn Asp Leu Ile His Gly Leu Tyr Pro Glu
            425                 430                 435

Ala Val Thr Ile Gly Glu Asp Val Ser Gly Met Pro Thr Phe Ala Leu
            440                 445                 450

Pro Val His Asp Gly Gly Val Gly Phe Asp Tyr Arg Met His Met Ala
455                 460                 465                 470

Val Ala Asp Lys Trp Ile Asp Leu Leu Lys Gln Ser Asp Glu Thr Trp
            475                 480                 485

Lys Met Gly Asp Ile Val His Thr Leu Thr Asn Arg Arg Trp Leu Glu
            490                 495                 500

Lys Cys Val Thr Tyr Ala Glu Ser His Asp Gln Ala Leu Val Gly Asp
            505                 510                 515

Lys Thr Ile Ala Phe Trp Leu Met Asp Lys Asp Met Tyr Asp Phe Met
520                 525                 530

Ala Leu Asp Arg Pro Ser Thr Pro Thr Ile Asp Arg Gly Ile Ala Leu
535                 540                 545                 550
```

```
His Lys Met Ile Arg Leu Ile Thr Met Gly Leu Gly Gly Glu Gly Tyr
                555                 560                 565

Leu Asn Phe Met Gly Asn Glu Phe Gly His Pro Glu Trp Ile Asp Phe
                570                 575                 580

Pro Arg Gly Pro Gln Arg Leu Pro Ser Gly Lys Phe Ile Pro Gly Asn
                585                 590                 595

Asn Asn Ser Tyr Asp Lys Cys Arg Arg Phe Asp Leu Gly Asp Ala
            600                 605                 610

Asp Tyr Leu Arg Tyr His Gly Met Gln Glu Phe Asp Gln Ala Met Gln
615                 620                 625                 630

His Leu Glu Gln Lys Tyr Glu Phe Met Thr Ser Asp His Gln Tyr Ile
                635                 640                 645

Ser Arg Lys His Glu Glu Asp Lys Val Ile Val Phe Glu Lys Gly Asp
                650                 655                 660

Leu Val Phe Val Phe Asn Phe His Cys Asn Asn Ser Tyr Phe Asp Tyr
                665                 670                 675

Arg Ile Gly Cys Arg Lys Pro Gly Val Tyr Lys Val Val Leu Asp Ser
            680                 685                 690

Asp Ala Gly Leu Phe Gly Gly Phe Ser Arg Ile His His Ala Ala Glu
695                 700                 705                 710

His Phe Thr Ala Asp Cys Ser His Asp Asn Arg Pro Tyr Ser Phe Ser
                715                 720                 725

Val Tyr Thr Pro Ser Arg Thr Cys Val Val Tyr Ala Pro Val Glu
                730                 735                 740

(2) INFORMATION FOR SEQ ID NO: 16:

(i) SEQUENCE CHARACTERISTICS:
        (A) LENGTH: 2763 base pairs
        (B) TYPE: nucleic acid
        (C) STRANDEDNESS: single
        (D) TOPOLOGY: Not Relevant (ii) MOLECULE TYPE: mRNA (iii) HYPOTHETICAL: NO (vi) ORIGINAL SOURCE:
        (A) ORGANISM: Zea mays (ix) FEATURE:
        (A) NAME/KEY: transit_peptide
        (B) LOCATION: 2..190

(ix) FEATURE:
        (A) NAME/KEY: mat_peptide
        (B) LOCATION: 191..2467

(ix) FEATURE:
        (A) NAME/KEY: CDS
        (B) LOCATION: 2..2470

(xi) SEQUENCE DESCRIPTION: SEQ ID NO: 16:

G CTG TGC CTC GTG TCG CCC TCT TCC TCG CCG ACT CCG CTT CCG CCG        46
  Leu Cys Leu Val Ser Pro Ser Ser Ser Pro Thr Pro Leu Pro Pro
  -63         -60             -55                 -50

CCG CGG CGC TCT CGC TCG CAT GCT GAT CGG GCG GCA CCG CCG GGG ATC     94
Pro Arg Arg Ser Arg Ser His Ala Asp Arg Ala Ala Pro Pro Gly Ile
            -45             -40                 -35

GCG GGT GGC GGC AAT GTG CGC CTG AGT GTG TTG TCT GTC CAG TGC AAG    142
Ala Gly Gly Gly Asn Val Arg Leu Ser Val Leu Ser Val Gln Cys Lys
        -30             -25                 -20
```

```
GCT CGC CGG TCA GGG GTG CGG AAG GTC AAG AGC AAA TTC GCC ACT GCA      190
Ala Arg Arg Ser Gly Val Arg Lys Val Lys Ser Lys Phe Ala Thr Ala
    -15             -10              -5

GCT ACT GTG CAA GAA GAT AAA ACT ATG GCA ACT GCC AAA GGC GAT GTC      238
Ala Thr Val Gln Glu Asp Lys Thr Met Ala Thr Ala Lys Gly Asp Val
  1           5               10              15

GAC CAT CTC CCC ATA TAC GAC CTG GAC CCC AAG CTG GAG ATA TTC AAG      286
Asp His Leu Pro Ile Tyr Asp Leu Asp Pro Lys Leu Glu Ile Phe Lys
             20              25              30

GAC CAT TTC AGG TAC CGG ATG AAA AGA TTC CTA GAG CAG AAA GGA TCA      334
Asp His Phe Arg Tyr Arg Met Lys Arg Phe Leu Glu Gln Lys Gly Ser
         35              40              45

ATT GAA GAA AAT GAG GGA AGT CTT GAA TCT TTT TCT AAA GGC TAT TTG      382
Ile Glu Glu Asn Glu Gly Ser Leu Glu Ser Phe Ser Lys Gly Tyr Leu
     50              55              60

AAA TTT GGG ATT AAT ACA AAT GAG GAT GGA ACT GTA TAT CGT GAA TGG      430
Lys Phe Gly Ile Asn Thr Asn Glu Asp Gly Thr Val Tyr Arg Glu Trp
 65              70              75              80

GCA CCT GCT GCG CAG GAG GCA GAG CTT ATT GGT GAC TTC AAT GAC TGG      478
Ala Pro Ala Ala Gln Glu Ala Glu Leu Ile Gly Asp Phe Asn Asp Trp
             85              90              95

AAT GGT GCA AAC CAT AAG ATG GAG AAG GAT AAA TTT GGT GTT TGG TCG      526
Asn Gly Ala Asn His Lys Met Glu Lys Asp Lys Phe Gly Val Trp Ser
         100             105             110

ATC AAA ATT GAC CAT GTC AAA GGG AAA CCT GCC ATC CCT CAC AAT TCC      574
Ile Lys Ile Asp His Val Lys Gly Lys Pro Ala Ile Pro His Asn Ser
     115             120             125

AAG GTT AAA TTT CGC TTT CTA CAT GGT GGA GTA TGG GTT GAT CGT ATT      622
Lys Val Lys Phe Arg Phe Leu His Gly Gly Val Trp Val Asp Arg Ile
 130             135             140

CCA GCA TTG ATT CGT TAT GCG ACT GTT GAT GCC TCT AAA TTT GGA GCT      670
Pro Ala Leu Ile Arg Tyr Ala Thr Val Asp Ala Ser Lys Phe Gly Ala
145             150             155             160

CCC TAT GAT GGT GTT CAT TGG GAT CCT CCT GCT TCT GAA AGG TAC ACA      718
Pro Tyr Asp Gly Val His Trp Asp Pro Pro Ala Ser Glu Arg Tyr Thr
             165             170             175

TTT AAG CAT CCT CGG CCT TCA AAG CCT GCT GCT CCA CGT ATC TAT GAA      766
Phe Lys His Pro Arg Pro Ser Lys Pro Ala Ala Pro Arg Ile Tyr Glu
         180             185             190

GCC CAT GTA GGT ATG AGT GGT GAA AAG CCA GCA GTA AGC ACA TAT AGG      814
Ala His Val Gly Met Ser Gly Glu Lys Pro Ala Val Ser Thr Tyr Arg
     195             200             205

GAA TTT GCA GAC AAT GTG TTG CCA CGC ATA CGA GCA AAT AAC TAC AAC      862
Glu Phe Ala Asp Asn Val Leu Pro Arg Ile Arg Ala Asn Asn Tyr Asn
 210             215             220

ACA GTT CAG TTG ATG GCA GTT ATG GAG CAT TCG TAC TAT GCT TCT TTC      910
Thr Val Gln Leu Met Ala Val Met Glu His Ser Tyr Tyr Ala Ser Phe
225             230             235             240

GGG TAC CAT GTG ACA AAT TTC TTT GCG GTT AGC AGC AGA TCA GGC ACA      958
Gly Tyr His Val Thr Asn Phe Phe Ala Val Ser Ser Arg Ser Gly Thr
             245             250             255

CCA GAG GAC CTC AAA TAT CTT GTT GAT AAG GCA CAC AGT TTG GGT TTG     1006
Pro Glu Asp Leu Lys Tyr Leu Val Asp Lys Ala His Ser Leu Gly Leu
         260             265             270

CGA GTT CTG ATG GAT GTT GTC CAT AGC CAT GCA AGT AAT AAT GTC ACA     1054
Arg Val Leu Met Asp Val Val His Ser His Ala Ser Asn Asn Val Thr
     275             280             285

GAT GGT TTA AAT GGC TAT GAT GTT GGA CAA AGC ACC CAA GAG TCC TAT     1102
Asp Gly Leu Asn Gly Tyr Asp Val Gly Gln Ser Thr Gln Glu Ser Tyr
290             295             300
```

| | | |
|---|---|---|
| TTT CAT GCG GGA GAT AGA GGT TAT CAT AAA CTT TGG GAT AGT CGG CTG<br>Phe His Ala Gly Asp Arg Gly Tyr His Lys Leu Trp Asp Ser Arg Leu<br>305                           310                     315                  320 | 1150 |
| TTC AAC TAT GCT AAC TGG GAG GTA TTA AGG TTT CTT CTT TCT AAC CTG<br>Phe Asn Tyr Ala Asn Trp Glu Val Leu Arg Phe Leu Leu Ser Asn Leu<br>                     325                     330                     335 | 1198 |
| AGA TAT TGG TTG GAT GAA TTC ATG TTT GAT GGC TTC CGA TTT GAT GGA<br>Arg Tyr Trp Leu Asp Glu Phe Met Phe Asp Gly Phe Arg Phe Asp Gly<br>               340                     345                     350 | 1246 |
| GTT ACA TCA ATG CTG TAT CAT CAC CAT GGT ATC AAT GTG GGG TTT ACT<br>Val Thr Ser Met Leu Tyr His His His Gly Ile Asn Val Gly Phe Thr<br>               355                     360                     365 | 1294 |
| GGA AAC TAC CAG GAA TAT TTC AGT TTG GAC ACA GCT GTG GAT GCA GTT<br>Gly Asn Tyr Gln Glu Tyr Phe Ser Leu Asp Thr Ala Val Asp Ala Val<br>370                     375                     380 | 1342 |
| GTT TAC ATG ATG CTT GCA AAC CAT TTA ATG CAC AAA CTC TTG CCA GAA<br>Val Tyr Met Met Leu Ala Asn His Leu Met His Lys Leu Leu Pro Glu<br>385                     390                     395                  400 | 1390 |
| GCA ACT GTT GTT GCT GAA GAT GTT TCA GGC ATG CCG GTC CTT TGC CGG<br>Ala Thr Val Val Ala Glu Asp Val Ser Gly Met Pro Val Leu Cys Arg<br>                     405                     410                     415 | 1438 |
| CCA GTT GAT GAA GGT GGG GTT GGG TTT GAC TAT CGC CTG GCA ATG GCT<br>Pro Val Asp Glu Gly Gly Val Gly Phe Asp Tyr Arg Leu Ala Met Ala<br>               420                     425                     430 | 1486 |
| ATC CCT GAT AGA TGG ATT GAC TAC CTG AAG AAT AAA GAT GAC TCT GAG<br>Ile Pro Asp Arg Trp Ile Asp Tyr Leu Lys Asn Lys Asp Asp Ser Glu<br>                     435                     440                     445 | 1534 |
| TGG TCG ATG GGT GAA ATA GCG CAT ACT TTG ACT AAC AGG AGA TAT ACT<br>Trp Ser Met Gly Glu Ile Ala His Thr Leu Thr Asn Arg Arg Tyr Thr<br>450                     455                     460 | 1582 |
| GAA AAA TGC ATC GCA TAT GCT GAG AGC CAT GAT CAG TCT ATT GTT GGC<br>Glu Lys Cys Ile Ala Tyr Ala Glu Ser His Asp Gln Ser Ile Val Gly<br>465                     470                     475                  480 | 1630 |
| GAC AAA ACT ATT GCA TTT CTC CTG ATG GAC AAG GAA ATG TAC ACT GGC<br>Asp Lys Thr Ile Ala Phe Leu Leu Met Asp Lys Glu Met Tyr Thr Gly<br>                     485                     490                     495 | 1678 |
| ATG TCA GAC TTG CAG CCT GCT TCA CCT ACA ATT GAT CGA GGG ATT GCA<br>Met Ser Asp Leu Gln Pro Ala Ser Pro Thr Ile Asp Arg Gly Ile Ala<br>               500                     505                     510 | 1726 |
| CTC CAA AAG ATG ATT CAC TTC ATC ACA ATG GCC CTT GGA GGT GAT GGC<br>Leu Gln Lys Met Ile His Phe Ile Thr Met Ala Leu Gly Gly Asp Gly<br>               515                     520                     525 | 1774 |
| TAC TTG AAT TTT ATG GGA AAT GAG TTT GGT CAC CCA GAA TGG ATT GAC<br>Tyr Leu Asn Phe Met Gly Asn Glu Phe Gly His Pro Glu Trp Ile Asp<br>530                     535                     540 | 1822 |
| TTT CCA AGA GAA GGG AAC AAC TGG AGC TAT GAT AAA TGC AGA CGA CAG<br>Phe Pro Arg Glu Gly Asn Asn Trp Ser Tyr Asp Lys Cys Arg Arg Gln<br>545                     550                     555                  560 | 1870 |
| TGG AGC CTT GTG GAC ACT GAT CAC TTG CGG TAC AAG TAC ATG AAT GCG<br>Trp Ser Leu Val Asp Thr Asp His Leu Arg Tyr Lys Tyr Met Asn Ala<br>               565                     570                     575 | 1918 |
| TTT GAC CAA GCG ATG AAT GCG CTC GAT GAG AGA TTT TCC TTC CTT TCG<br>Phe Asp Gln Ala Met Asn Ala Leu Asp Glu Arg Phe Ser Phe Leu Ser<br>                     580                     585                     590 | 1966 |
| TCG TCA AAG CAG ATC GTC AGC GAC ATG AAC GAT GAG GAA AAG GTT ATT<br>Ser Ser Lys Gln Ile Val Ser Asp Met Asn Asp Glu Glu Lys Val Ile<br>595                     600                     605 | 2014 |
| GTC TTT GAA CGT GGA GAT TTA GTT TTT GTT TTC AAT TTC CAT CCC AAG<br>Val Phe Glu Arg Gly Asp Leu Val Phe Val Phe Asn Phe His Pro Lys | 2062 |

```
                 610              615              620
AAA ACT TAC GAG GGC TAC AAA GTG GGA TGC GAT TTG CCT GGG AAA TAC        2110
Lys Thr Tyr Glu Gly Tyr Lys Val Gly Cys Asp Leu Pro Gly Lys Tyr
625             630              635              640

AGA GTA GCC CTG GAC TCT GAT GCT CTG GTC TTC GGT GGA CAT GGA AGA        2158
Arg Val Ala Leu Asp Ser Asp Ala Leu Val Phe Gly Gly His Gly Arg
                645              650              655

GTT GGC CAC GAC GTG GAT CAC TTC ACG TCG CCT GAA GGG GTG CCA GGG        2206
Val Gly His Asp Val Asp His Phe Thr Ser Pro Glu Gly Val Pro Gly
                660              665              670

GTG CCC GAA ACG AAC TTC AAC AAC CGG CCG AAC TCG TTC AAA GTC CTT        2254
Val Pro Glu Thr Asn Phe Asn Asn Arg Pro Asn Ser Phe Lys Val Leu
                675              680              685

TCT CCG CCC CGC ACC TGT GTG GCT TAT TAC CGT GTA GAC GAA GCA GGG        2302
Ser Pro Pro Arg Thr Cys Val Ala Tyr Tyr Arg Val Asp Glu Ala Gly
                690              695              700

GCT GGA CGA CGT CTT CAC GCG AAA GCA GAG ACA GGA AAG ACG TCT CCA        2350
Ala Gly Arg Arg Leu His Ala Lys Ala Glu Thr Gly Lys Thr Ser Pro
705             710              715              720

GCA GAG AGC ATC GAC GTC AAA GCT TCC AGA GCT AGT AGC AAA GAA GAC        2398
Ala Glu Ser Ile Asp Val Lys Ala Ser Arg Ala Ser Ser Lys Glu Asp
                725              730              735

AAG GAG GCA ACG GCT GGT GGC AAG AAG GGA TGG AAG TTT GCG CGG CAG        2446
Lys Glu Ala Thr Ala Gly Gly Lys Lys Gly Trp Lys Phe Ala Arg Gln
                740              745              750

CCA TCC GAT CAA GAT ACC AAA TGA AGCCACGAGT CCTTGGTGAG GACTGGACTG       2500
Pro Ser Asp Gln Asp Thr Lys  *
                755              760

GCTGCCGGCG CCCTGTTAGT AGTCCTGCTC TACTGGACTA GCCGCCGCTG GCGCCCTTGG      2560

AACGGTCCTT TCCTGTAGCT TGCAGGCGAC TGGTGTCTCA TCACCGAGCA GGCAGGCACT      2620

GCTTGTATAG CTTTTCTAGA ATAATAATCA GGGATGGATG GATGGTGTGT ATTGGCTATC      2680

TGGCTAGACG TGCATGTGCC CAGTTTGTAT GTACAGGAGC AGTTCCCGTC CAGAATAAAA      2740

AAAAACTTGT TGGGGGGTTT TTC                                             2763

(2) INFORMATION FOR SEQ ID NO: 17:

(i) SEQUENCE CHARACTERISTICS:
        (A) LENGTH: 822 amino acids
        (B) TYPE: amino acid
        (D) TOPOLOGY: linear (ii) MOLECULE TYPE: protein (xi) SEQUENCE DESCRIPTION: SEQ ID NO: 17:

Leu Cys Leu Val Ser Pro Ser Ser Pro Thr Pro Leu Pro Pro
-63             -60              -55              -50

Arg Arg Ser Arg Ser His Ala Asp Arg Ala Ala Pro Pro Gly Ile Ala
        -45              -40              -35

Gly Gly Gly Asn Val Arg Leu Ser Val Leu Ser Val Gln Cys Lys Ala
        -30              -25              -20

Arg Arg Ser Gly Val Arg Lys Val Lys Ser Lys Phe Ala Thr Ala Ala
-15              -10              -5                        1

Thr Val Gln Glu Asp Lys Thr Met Ala Thr Ala Lys Gly Asp Val Asp
                5                10               15

His Leu Pro Ile Tyr Asp Leu Asp Pro Lys Leu Glu Ile Phe Lys Asp
                20               25               30

His Phe Arg Tyr Arg Met Lys Arg Phe Leu Glu Gln Lys Gly Ser Ile
```

-continued

```
             35                  40                  45
Glu Glu Asn Glu Gly Ser Leu Glu Ser Phe Ser Lys Gly Tyr Leu Lys
 50                  55                  60                  65

Phe Gly Ile Asn Thr Asn Glu Asp Gly Thr Val Tyr Arg Glu Trp Ala
                 70                  75                  80

Pro Ala Ala Gln Glu Ala Glu Leu Ile Gly Asp Phe Asn Asp Trp Asn
                     85                  90                  95

Gly Ala Asn His Lys Met Glu Lys Asp Lys Phe Gly Val Trp Ser Ile
                100                 105                 110

Lys Ile Asp His Val Lys Gly Lys Pro Ala Ile Pro His Asn Ser Lys
115                 120                 125

Val Lys Phe Arg Phe Leu His Gly Gly Val Trp Val Asp Arg Ile Pro
130                 135                 140                 145

Ala Leu Ile Arg Tyr Ala Thr Val Asp Ala Ser Lys Phe Gly Ala Pro
                150                 155                 160

Tyr Asp Gly Val His Trp Asp Pro Pro Ala Ser Glu Arg Tyr Thr Phe
                165                 170                 175

Lys His Pro Arg Pro Ser Lys Pro Ala Ala Pro Arg Ile Tyr Glu Ala
                180                 185                 190

His Val Gly Met Ser Gly Glu Lys Pro Ala Val Ser Thr Tyr Arg Glu
                195                 200                 205

Phe Ala Asp Asn Val Leu Pro Arg Ile Arg Ala Asn Asn Tyr Asn Thr
210                 215                 220                 225

Val Gln Leu Met Ala Val Met Glu His Ser Tyr Tyr Ala Ser Phe Gly
                230                 235                 240

Tyr His Val Thr Asn Phe Phe Ala Val Ser Ser Arg Ser Gly Thr Pro
                245                 250                 255

Glu Asp Leu Lys Tyr Leu Val Asp Lys Ala His Ser Leu Gly Leu Arg
                260                 265                 270

Val Leu Met Asp Val Val His Ser His Ala Ser Asn Asn Val Thr Asp
                275                 280                 285

Gly Leu Asn Gly Tyr Asp Val Gly Gln Ser Thr Gln Glu Ser Tyr Phe
290                 295                 300                 305

His Ala Gly Asp Arg Gly Tyr His Lys Leu Trp Asp Ser Arg Leu Phe
                310                 315                 320

Asn Tyr Ala Asn Trp Glu Val Leu Arg Phe Leu Leu Ser Asn Leu Arg
                325                 330                 335

Tyr Trp Leu Asp Glu Phe Met Phe Asp Gly Phe Arg Phe Asp Gly Val
                340                 345                 350

Thr Ser Met Leu Tyr His His His Gly Ile Asn Val Gly Phe Thr Gly
                355                 360                 365

Asn Tyr Gln Glu Tyr Phe Ser Leu Asp Thr Ala Val Asp Ala Val Val
370                 375                 380                 385

Tyr Met Met Leu Ala Asn His Leu Met His Lys Leu Leu Pro Glu Ala
                390                 395                 400

Thr Val Val Ala Glu Asp Val Ser Gly Met Pro Val Leu Cys Arg Pro
                405                 410                 415

Val Asp Glu Gly Gly Val Gly Phe Asp Tyr Arg Leu Ala Met Ala Ile
                420                 425                 430

Pro Asp Arg Trp Ile Asp Tyr Leu Lys Asn Lys Asp Asp Ser Glu Trp
                435                 440                 445

Ser Met Gly Glu Ile Ala His Thr Leu Thr Asn Arg Arg Tyr Thr Glu
450                 455                 460                 465
```

```
Lys Cys Ile Ala Tyr Ala Glu Ser His Asp Gln Ser Ile Val Gly Asp
                470                 475                 480

Lys Thr Ile Ala Phe Leu Leu Met Asp Lys Glu Met Tyr Thr Gly Met
                485                 490                 495

Ser Asp Leu Gln Pro Ala Ser Pro Thr Ile Asp Arg Gly Ile Ala Leu
                500                 505                 510

Gln Lys Met Ile His Phe Ile Thr Met Ala Leu Gly Gly Asp Gly Tyr
        515                 520                 525

Leu Asn Phe Met Gly Asn Glu Phe Gly His Pro Glu Trp Ile Asp Phe
530                 535                 540                 545

Pro Arg Glu Gly Asn Asn Trp Ser Tyr Asp Lys Cys Arg Arg Gln Trp
                550                 555                 560

Ser Leu Val Asp Thr Asp His Leu Arg Tyr Lys Tyr Met Asn Ala Phe
                565                 570                 575

Asp Gln Ala Met Asn Ala Leu Asp Glu Arg Phe Ser Phe Leu Ser Ser
                580                 585                 590

Ser Lys Gln Ile Val Ser Asp Met Asn Asp Glu Glu Lys Val Ile Val
        595                 600                 605

Phe Glu Arg Gly Asp Leu Val Phe Val Phe Asn Phe His Pro Lys Lys
610                 615                 620                 625

Thr Tyr Glu Gly Tyr Lys Val Gly Cys Asp Leu Pro Gly Lys Tyr Arg
                630                 635                 640

Val Ala Leu Asp Ser Asp Ala Leu Val Phe Gly Gly His Gly Arg Val
                645                 650                 655

Gly His Asp Val Asp His Phe Thr Ser Pro Glu Gly Val Pro Gly Val
        660                 665                 670

Pro Glu Thr Asn Phe Asn Asn Arg Pro Asn Ser Phe Lys Val Leu Ser
675                 680                 685

Pro Pro Arg Thr Cys Val Ala Tyr Tyr Arg Val Asp Glu Ala Gly Ala
690                 695                 700                 705

Gly Arg Arg Leu His Ala Lys Ala Glu Thr Gly Lys Thr Ser Pro Ala
                710                 715                 720

Glu Ser Ile Asp Val Lys Ala Ser Arg Ala Ser Ser Lys Glu Asp Lys
                725                 730                 735

Glu Ala Thr Ala Gly Gly Lys Lys Gly Trp Lys Phe Ala Arg Gln Pro
                740                 745                 750

Ser Asp Gln Asp Thr Lys
        755                 760

(2) INFORMATION FOR SEQ ID NO: 18:

(i) SEQUENCE CHARACTERISTICS:
        (A) LENGTH: 153 base pairs
        (B) TYPE: nucleic acid
        (C) STRANDEDNESS: single
        (D) TOPOLOGY: Not Relevant (ii) MOLECULE TYPE: cDNA to mRNA (iii) HYPOTHETICAL: NO (vi) ORIGINAL SOURCE:
        (A) ORGANISM: Zea mays (ix) FEATURE:
        (A) NAME/KEY: CDS
        (B) LOCATION: 1..153

(xi) SEQUENCE DESCRIPTION: SEQ ID NO: 18:
```

```
ATG GCG ACG CCC TCG GCC GTG GGC GCC GCG TGC CTC CTC CTC GCG CGG      48
Met Ala Thr Pro Ser Ala Val Gly Ala Ala Cys Leu Leu Leu Ala Arg
            765                 770                 775

GCC GCC TGG CCG GCC GCC GTC GGC GAC CGG GCG CGC CCG CGG AGG CTC      96
Ala Ala Trp Pro Ala Ala Val Gly Asp Arg Ala Arg Pro Arg Arg Leu
            780                 785                 790

CAG CGC GTG CTG CGC CGC CGG TGC GTC GCG GAG CTG AGC AGG GAG GGG     144
Gln Arg Val Leu Arg Arg Arg Cys Val Ala Glu Leu Ser Arg Glu Gly
            795                 800                 805

CCC CAT ATG                                                         153
Pro His Met
    810

(2) INFORMATION FOR SEQ ID NO: 19:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO: 19:

Met Ala Thr Pro Ser Ala Val Gly Ala Ala Cys Leu Leu Leu Ala Arg
 1               5                  10                  15

Ala Ala Trp Pro Ala Ala Val Gly Asp Arg Ala Arg Pro Arg Arg Leu
                20                  25                  30

Gln Arg Val Leu Arg Arg Arg Cys Val Ala Glu Leu Ser Arg Glu Gly
            35                  40                  45

Pro His Met
    50

(2) INFORMATION FOR SEQ ID NO: 20:

(i) SEQUENCE CHARACTERISTICS:
        (A) LENGTH: 1620 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (ix) FEATURE:
        (A) NAME/KEY: CDS
        (B) LOCATION: 1..1620

(xi) SEQUENCE DESCRIPTION: SEQ ID NO: 20:

TGC GTC GCG GAG CTG AGC AGG GAG GAC CTC GGT CTC GAA CCT GAA GGG      48
Cys Val Ala Glu Leu Ser Arg Glu Asp Leu Gly Leu Glu Pro Glu Gly
            55                  60                  65

ATT GCT GAA GGT TCC ATC GAT AAC ACA GTA GTT GTG GCA AGT GAG CAA      96
Ile Ala Glu Gly Ser Ile Asp Asn Thr Val Val Val Ala Ser Glu Gln
            70                  75                  80

GAT TCT GAG ATT GTG GTT GGA AAG GAG CAA GCT CGA GCT AAA GTA ACA     144
Asp Ser Glu Ile Val Val Gly Lys Glu Gln Ala Arg Ala Lys Val Thr
    85                  90                  95

CAA AGC ATT GTC TTT GTA ACC GGC GAA GCT TCT CCT TAT GCA AAG TCT     192
Gln Ser Ile Val Phe Val Thr Gly Glu Ala Ser Pro Tyr Ala Lys Ser
100                 105                 110                 115

GGG GGT CTA GGA GAT GTT TGT GGT TCA TTG CCA GTT GCT CTT GCT GCT     240
Gly Gly Leu Gly Asp Val Cys Gly Ser Leu Pro Val Ala Leu Ala Ala
            120                 125                 130
```

```
CGT GGT CAC CGT GTG ATG GTT GTA ATG CCC AGA TAT TTA AAT GGT ACC      288
Arg Gly His Arg Val Met Val Val Met Pro Arg Tyr Leu Asn Gly Thr
            135                 140                 145

TCC GAT AAG AAT TAT GCA AAT GCA TTT TAC ACA GAA AAA CAC ATT CGG      336
Ser Asp Lys Asn Tyr Ala Asn Ala Phe Tyr Thr Glu Lys His Ile Arg
        150                 155                 160

ATT CCA TGC TTT GGC GGT GAA CAT GAA GTT ACC TTC TTC CAT GAG TAT      384
Ile Pro Cys Phe Gly Gly Glu His Glu Val Thr Phe Phe His Glu Tyr
    165                 170                 175

AGA GAT TCA GTT GAC TGG GTG TTT GTT GAT CAT CCC TCA TAT CAC AGA      432
Arg Asp Ser Val Asp Trp Val Phe Val Asp His Pro Ser Tyr His Arg
180                 185                 190                 195

CCT GGA AAT TTA TAT GGA GAT AAG TTT GGT GCT TTT GGT GAT AAT CAG      480
Pro Gly Asn Leu Tyr Gly Asp Lys Phe Gly Ala Phe Gly Asp Asn Gln
                200                 205                 210

TTC AGA TAC ACA CTC CTT TGC TAT GCT GCA TGT GAG GCT CCT TTG ATC      528
Phe Arg Tyr Thr Leu Leu Cys Tyr Ala Ala Cys Glu Ala Pro Leu Ile
            215                 220                 225

CTT GAA TTG GGA GGA TAT ATT TAT GGA CAG AAT TGC ATG TTT GTT GTC      576
Leu Glu Leu Gly Gly Tyr Ile Tyr Gly Gln Asn Cys Met Phe Val Val
        230                 235                 240

AAT GAT TGG CAT GCC AGT CTA GTG CCA GTC CTT CTT GCT GCA AAA TAT      624
Asn Asp Trp His Ala Ser Leu Val Pro Val Leu Leu Ala Ala Lys Tyr
    245                 250                 255

AGA CCA TAT GGT GTT TAT AAA GAC TCC CGC AGC ATT CTT GTA ATA CAT      672
Arg Pro Tyr Gly Val Tyr Lys Asp Ser Arg Ser Ile Leu Val Ile His
260                 265                 270                 275

AAT TTA GCA CAT CAG GGT GTA GAG CCT GCA AGC ACA TAT CCT GAC CTT      720
Asn Leu Ala His Gln Gly Val Glu Pro Ala Ser Thr Tyr Pro Asp Leu
                280                 285                 290

GGG TTG CCA CCT GAA TGG TAT GGA GCT CTG GAG TGG GTA TTC CCT GAA      768
Gly Leu Pro Pro Glu Trp Tyr Gly Ala Leu Glu Trp Val Phe Pro Glu
            295                 300                 305

TGG GCG AGG AGG CAT GCC CTT GAC AAG GGT GAG GCA GTT AAT TTT TTG      816
Trp Ala Arg Arg His Ala Leu Asp Lys Gly Glu Ala Val Asn Phe Leu
        310                 315                 320

AAA GGT GCA GTT GTG ACA GCA GAT CGA ATC GTG ACT GTC AGT AAG GGT      864
Lys Gly Ala Val Val Thr Ala Asp Arg Ile Val Thr Val Ser Lys Gly
    325                 330                 335

TAT TCG TGG GAG GTC ACA ACT GCT GAA GGT GGA CAG GGC CTC AAT GAG      912
Tyr Ser Trp Glu Val Thr Thr Ala Glu Gly Gly Gln Gly Leu Asn Glu
340                 345                 350                 355

CTC TTA AGC TCC AGA AAG AGT GTA TTA AAC GGA ATT GTA AAT GGA ATT      960
Leu Leu Ser Ser Arg Lys Ser Val Leu Asn Gly Ile Val Asn Gly Ile
                360                 365                 370

GAC ATT AAT GAT TGG AAC CCT GCC ACA GAC AAA TGT ATC CCC TGT CAT     1008
Asp Ile Asn Asp Trp Asn Pro Ala Thr Asp Lys Cys Ile Pro Cys His
            375                 380                 385

TAT TCT GTT GAT GAC CTC TCT GGA AAG GCC AAA TGT AAA GGT GCA TTG     1056
Tyr Ser Val Asp Asp Leu Ser Gly Lys Ala Lys Cys Lys Gly Ala Leu
        390                 395                 400

CAG AAG GAG CTG GGT TTA CCT ATA AGG CCT GAT GTT CCT CTG ATT GGC     1104
Gln Lys Glu Leu Gly Leu Pro Ile Arg Pro Asp Val Pro Leu Ile Gly
    405                 410                 415

TTT ATT GGA AGG TTG GAT TAT CAG AAA GGC ATT GAT CTC ATT CAA CTT     1152
Phe Ile Gly Arg Leu Asp Tyr Gln Lys Gly Ile Asp Leu Ile Gln Leu
420                 425                 430                 435

ATC ATA CCA GAT CTC ATG CGG GAA GAT GTT CAA TTT GTC ATG CTT GGA     1200
Ile Ile Pro Asp Leu Met Arg Glu Asp Val Gln Phe Val Met Leu Gly
```

-continued

```
              440              445              450
TCT GGT GAC CCA GAG CTT GAA GAT TGG ATG AGA TCT ACA GAG TCG ATC         1248
Ser Gly Asp Pro Glu Leu Glu Asp Trp Met Arg Ser Thr Glu Ser Ile
            455                  460                  465

TTC AAG GAT AAA TTT CGT GGA TGG GTT GGA TTT AGT GTT CCA GTT TCC         1296
Phe Lys Asp Lys Phe Arg Gly Trp Val Gly Phe Ser Val Pro Val Ser
            470                  475                  480

CAC CGA ATA ACT GCC GGC TGC GAT ATA TTG TTA ATG CCA TCC AGA TTC         1344
His Arg Ile Thr Ala Gly Cys Asp Ile Leu Leu Met Pro Ser Arg Phe
            485                  490                  495

GAA CCT TGT GGT CTC AAT CAG CTA TAT GCT ATG CAG TAT GGC ACA GTT         1392
Glu Pro Cys Gly Leu Asn Gln Leu Tyr Ala Met Gln Tyr Gly Thr Val
500                  505                  510                  515

CCT GTT GTC CAT GCA ACT GGG GGC CTT AGA GAT ACC GTG GAG AAC TTC         1440
Pro Val Val His Ala Thr Gly Gly Leu Arg Asp Thr Val Glu Asn Phe
                520                  525                  530

AAC CCT TTC GGT GAG AAT GGA GAG CAG GGT ACA GGG TGG GCA TTC GCA         1488
Asn Pro Phe Gly Glu Asn Gly Glu Gln Gly Thr Gly Trp Ala Phe Ala
                535                  540                  545

CCC CTA ACC ACA GAA AAC ATG TTT GTG GAC ATT GCG AAC TGC AAT ATC         1536
Pro Leu Thr Thr Glu Asn Met Phe Val Asp Ile Ala Asn Cys Asn Ile
                550                  555                  560

TAC ATA CAG GGA ACA CAA GTC CTC CTG GGA AGG GCT AAT GAA GCG AGG         1584
Tyr Ile Gln Gly Thr Gln Val Leu Leu Gly Arg Ala Asn Glu Ala Arg
565                  570                  575

CAT GTC AAA AGA CTT CAC GTG GGA CCA TGC CGC TGA                         1620
His Val Lys Arg Leu His Val Gly Pro Cys Arg  *
580                  585                  590
```

(2) INFORMATION FOR SEQ ID NO: 21:

(i) SEQUENCE CHARACTERISTICS:
        (A) LENGTH: 539 amino acids
        (B) TYPE: amino acid
        (D) TOPOLOGY: linear (ii) MOLECULE TYPE: protein (xi) SEQUENCE DESCRIPTION: SEQ ID NO: 21:

```
Cys Val Ala Glu Leu Ser Arg Glu Asp Leu Gly Leu Glu Pro Glu Gly
 1               5                  10                  15

Ile Ala Glu Gly Ser Ile Asp Asn Thr Val Val Ala Ser Glu Gln
                20                  25                  30

Asp Ser Glu Ile Val Val Gly Lys Glu Gln Ala Arg Ala Lys Val Thr
            35                  40                  45

Gln Ser Ile Val Phe Val Thr Gly Glu Ala Ser Pro Tyr Ala Lys Ser
        50                  55                  60

Gly Gly Leu Gly Asp Val Cys Gly Ser Leu Pro Val Ala Leu Ala Ala
65                  70                  75                  80

Arg Gly His Arg Val Met Val Met Pro Arg Tyr Leu Asn Gly Thr
                85                  90                  95

Ser Asp Lys Asn Tyr Ala Asn Ala Phe Tyr Thr Glu Lys His Ile Arg
            100                 105                 110

Ile Pro Cys Phe Gly Gly Glu His Glu Val Thr Phe Phe His Glu Tyr
        115                 120                 125

Arg Asp Ser Val Asp Trp Val Phe Val Asp His Pro Ser Tyr His Arg
    130                 135                 140

Pro Gly Asn Leu Tyr Gly Asp Lys Phe Gly Ala Phe Gly Asp Asn Gln
145                 150                 155                 160
```

```
Phe Arg Tyr Thr Leu Leu Cys Tyr Ala Ala Cys Glu Ala Pro Leu Ile
                165                 170                 175

Leu Glu Leu Gly Gly Tyr Ile Tyr Gly Gln Asn Cys Met Phe Val Val
            180                 185                 190

Asn Asp Trp His Ala Ser Leu Val Pro Val Leu Leu Ala Ala Lys Tyr
        195                 200                 205

Arg Pro Tyr Gly Val Tyr Lys Asp Ser Arg Ser Ile Leu Val Ile His
    210                 215                 220

Asn Leu Ala His Gln Gly Val Glu Pro Ala Ser Thr Tyr Pro Asp Leu
225                 230                 235                 240

Gly Leu Pro Pro Glu Trp Tyr Gly Ala Leu Glu Trp Val Phe Pro Glu
                245                 250                 255

Trp Ala Arg Arg His Ala Leu Asp Lys Gly Glu Ala Val Asn Phe Leu
                260                 265                 270

Lys Gly Ala Val Val Thr Ala Asp Arg Ile Val Thr Val Ser Lys Gly
            275                 280                 285

Tyr Ser Trp Glu Val Thr Thr Ala Glu Gly Gly Gln Gly Leu Asn Glu
        290                 295                 300

Leu Leu Ser Ser Arg Lys Ser Val Leu Asn Gly Ile Val Asn Gly Ile
305                 310                 315                 320

Asp Ile Asn Asp Trp Asn Pro Ala Thr Asp Lys Cys Ile Pro Cys His
                325                 330                 335

Tyr Ser Val Asp Asp Leu Ser Gly Lys Ala Lys Cys Lys Gly Ala Leu
                340                 345                 350

Gln Lys Glu Leu Gly Leu Pro Ile Arg Pro Asp Val Pro Leu Ile Gly
            355                 360                 365

Phe Ile Gly Arg Leu Asp Tyr Gln Lys Gly Ile Asp Leu Ile Gln Leu
        370                 375                 380

Ile Ile Pro Asp Leu Met Arg Glu Asp Val Gln Phe Val Met Leu Gly
385                 390                 395                 400

Ser Gly Asp Pro Glu Leu Glu Asp Trp Met Arg Ser Thr Glu Ser Ile
                405                 410                 415

Phe Lys Asp Lys Phe Arg Gly Trp Val Gly Phe Ser Val Pro Val Ser
                420                 425                 430

His Arg Ile Thr Ala Gly Cys Asp Ile Leu Leu Met Pro Ser Arg Phe
            435                 440                 445

Glu Pro Cys Gly Leu Asn Gln Leu Tyr Ala Met Gln Tyr Gly Thr Val
        450                 455                 460

Pro Val Val His Ala Thr Gly Gly Leu Arg Asp Thr Val Glu Asn Phe
465                 470                 475                 480

Asn Pro Phe Gly Glu Asn Gly Glu Gln Gly Thr Gly Trp Ala Phe Ala
                485                 490                 495

Pro Leu Thr Thr Glu Asn Met Phe Val Asp Ile Ala Asn Cys Asn Ile
                500                 505                 510

Tyr Ile Gln Gly Thr Gln Val Leu Leu Gly Arg Ala Asn Glu Ala Arg
            515                 520                 525

His Val Lys Arg Leu His Val Gly Pro Cys Arg
530                 535                 540

(2) INFORMATION FOR SEQ ID NO: 22:

(i) SEQUENCE CHARACTERISTICS:
        (A) LENGTH: 30 base pairs
        (B) TYPE: nucleic acid
```

```
        (C) STRANDEDNESS: single
        (D) TOPOLOGY: linear (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO: 22:

GTGGATCCAT GGCGACGCCC TCGGCCGTGG                              30

(2) INFORMATION FOR SEQ ID NO: 23:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 23:

CTGAATTCCA TATGGGGCCC CTCCCTGCTC AGCTC                        35

(2) INFORMATION FOR SEQ ID NO: 24:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 24:

CTCTGAGCTC AAGCTTGCTA CTTTCTTTCC TTAATG                       36

(2) INFORMATION FOR SEQ ID NO: 25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide"

(xi) SEQUENCE DESCRIPTION: SEQ ID NO: 25:

GTCTCCGCGG TGGTGTCCTT GCTTCCTAG                               29

(2) INFORMATION FOR SEQ ID NO: 26:

(i) SEQUENCE CHARACTERISTICS:
        (A) LENGTH: 53 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (xi) SEQUENCE DESCRIPTION: SEQ ID NO: 26:

TGCGTCGCGG AGCTGAGCAG GGAGGTCTCC GCGGTGGTGT CCTTGCTTCC TAG    53

(2) INFORMATION FOR SEQ ID NO: 27:
```

```
    (i) SEQUENCE CHARACTERISTICS:
        (A) LENGTH: 8 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO: 27:

Cys Val Ala Glu Leu Ser Arg Glu
1               5

(2) INFORMATION FOR SEQ ID NO: 28:

(i) SEQUENCE CHARACTERISTICS:
        (A) LENGTH: 16 base pairs
        (B) TYPE: nucleic acid
        (C) STRANDEDNESS: double
        (D) TOPOLOGY: Not Relevant (ii) MOLECULE TYPE: cDNA to mRNA (xi) SEQUENCE DESCRIPTION: SEQ ID NO: 28:

AGAGAGAGAG AGAGAG                                                       16

(2) INFORMATION FOR SEQ ID NO: 29:

(i) SEQUENCE CHARACTERISTICS:
        (A) LENGTH: 36 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (xi) SEQUENCE DESCRIPTION: SEQ ID NO: 29:

AAGAAGAAGA AGAAGAAGAA GAAGAAGAAG AAGAAG                                 36

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: double
        (D) TOPOLOGY: Not Relevant (ii) MOLECULE TYPE: cDNA to mRNA (iii) HYPOTHETICAL: NO (xi) SEQUENCE DESCRIPTION: SEQ ID NO: 30:

AAAAAAAAAA AAAAAAAA                                                     18

(2) INFORMATION FOR SEQ ID NO: 31:

(i) SEQUENCE CHARACTERISTICS:
        (A) LENGTH: 11 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO: 31:
```

```
AGATAATGCA G                                                          11

(2) INFORMATION FOR SEQ ID NO: 32:

(i) SEQUENCE CHARACTERISTICS:
        (A) LENGTH: 10 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "Oligonucleotide"

(iii) HYPOTHETICAL: NO (xi) SEQUENCE DESCRIPTION: SEQ ID NO: 32:

AACAATGGCT                                                            10

(2) INFORMATION FOR SEQ ID NO: 33:

(i) SEQUENCE CHARACTERISTICS:
        (A) LENGTH: 56 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO: 33:

Met Ala Ser Ser Met Leu Ser Ser Ala Ala Val Ala Thr Arg Thr Asn
1               5                   10                  15

Pro Ala Gln Ala Ser Met Val Ala Pro Phe Thr Gly Leu Lys Ser Ala
            20                  25                  30

Ala Phe Pro Val Ser Arg Lys Gln Asn Leu Asp Ile Thr Ser Ile Ala
        35                  40                  45

Ser Asn Gly Gly Arg Val Gln Cys
    50                  55

(2) INFORMATION FOR SEQ ID NO: 34:

(i) SEQUENCE CHARACTERISTICS:
        (A) LENGTH: 58 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO: 34:

Met Ala Pro Thr Val Met Met Ala Ser Ser Ala Thr Ala Thr Arg Thr
1               5                   10                  15

Asn Pro Ala Gln Ala Ser Ala Val Ala Pro Phe Gln Gly Leu Lys Ser
            20                  25                  30

Thr Ala Ser Leu Pro Val Ala Arg Arg Ser Ser Arg Ser Leu Gly Asn
        35                  40                  45

Val Ala Ser Asn Gly Gly Arg Ile Arg Cys
    50                  55

(2) INFORMATION FOR SEQ ID NO: 35:

(i) SEQUENCE CHARACTERISTICS:
        (A) LENGTH: 58 amino acids
```

(B) TYPE: amino acid
            (C) STRANDEDNESS: single
            (D) TOPOLOGY: Not Relevant (ii) MOLECULE TYPE: peptide (iii) HYPOTHETICAL: NO (xi) SEQUENCE DESCRIPTION: SEQ ID NO: 35:

Met Ala Gln Ile Leu Ala Pro Ser Thr Gln Trp Gln Met Arg Ile Thr
1               5                   10                  15

Lys Thr Ser Pro Cys Ala Thr Pro Ile Thr Ser Lys Met Trp Ser Ser
            20                  25                  30

Leu Val Met Lys Gln Thr Lys Lys Val Ala His Ser Ala Lys Phe Arg
        35                  40                  45

Val Met Ala Val Asn Ser Glu Asn Gly Thr
    50                  55

(2) INFORMATION FOR SEQ ID NO: 36:

(i) SEQUENCE CHARACTERISTICS:
        (A) LENGTH: 74 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO: 36:

Met Ala Ala Leu Ala Thr Ser Gln Leu Val Ala Thr Arg Ala Gly His
1               5                   10                  15

Gly Val Pro Asp Ala Ser Thr Phe Arg Arg Gly Ala Ala Gln Gly Leu
            20                  25                  30

Arg Gly Ala Arg Ala Ser Ala Ala Ala Asp Thr Leu Ser Met Arg Thr
        35                  40                  45

Ser Ala Arg Ala Ala Pro Arg His Gln Gln Gln Ala Arg Arg Gly Gly
    50                  55                  60

Arg Phe Pro Phe Pro Ser Leu Val Val Cys
65                  70

(2) INFORMATION FOR SEQ ID NO: 37:

(i) SEQUENCE CHARACTERISTICS:
        (A) LENGTH: 39 amino acids
        (B) TYPE: amino acid
        (C) STRANDEDNESS: single
        (D) TOPOLOGY: Not Relevant (ii) MOLECULE TYPE: peptide (iii) HYPOTHETICAL: NO (xi) SEQUENCE DESCRIPTION: SEQ ID NO: 37:

Met Ala Thr Pro Ser Ala Val Gly Ala Ala Cys Leu Leu Leu Ala Arg
1               5                   10                  15

Xaa Ala Trp Pro Ala Ala Val Gly Asp Arg Ala Arg Pro Arg Arg Leu
            20                  25                  30

Gln Arg Val Leu Arg Arg Arg
        35

The invention claimed is:

1. A recombinant nucleic acid construct comprising:

a) a promoter adapted to target expression of a payload polypeptide in a starch-containing tissue of a plant during starch formation, and b) a nucleic acid sequence which is oriented 3' to said promoter encoding a hybrid polypeptide, said hybrid polypeptide comprising an N-terminal transit peptide having an amino acid sequence selected from the group consisting of SEQ ID NO: 33, SEQ ID NO: 34, SEQ ID NO: 35, SEQ ID NO: 35, SEQ ID NO: 36, and SEQ ID NO: 37; a starch-encapsulating region from maize starch synthase having an amino acid sequence 292–539 of SEQ ID NO: 21; and a payload polypeptide, wherein said payload polypeptide can be either N- or C-terminal to the starch encapsulating region.

2. The construct of claim 1, wherein the promoter and terminator are adapted for expression of the hybrid polypeptide within starch of a monocot plant.

3. The construct of claim 1, wherein the promoter and terminator are adapted for expression of the hybrid polypeptide within starch of a dicot plant.

4. An expression vector comprising the construct of claim 1.

5. A cell transformed to comprise the construct of claim 1, said cell being capable of expressing said construct.

6. The cell of claim 5 which is a plant cell.

* * * * *